(12) United States Patent  (10) Patent No.: US 10,839,514 B2
Accomazzi et al.  (45) Date of Patent: Nov. 17, 2020

(54) METHODS AND SYSTEMS FOR DYNAMICALLY TRAINING AND APPLYING NEURAL NETWORK ANALYSES TO MEDICAL IMAGES

(71) Applicant: International Medical Solutions, Inc., Mississauga (CA)

(72) Inventors: Vittorio Accomazzi, Toronto (CA); Vernon Colaco, Mission Viejo, CA (US)

(73) Assignee: International Medical Solutions, Inc., Mississauga (CA)

( * ) Notice: Subject to any disclaimer, the term of this patent is extended or adjusted under 35 U.S.C. 154(b) by 0 days.

(21) Appl. No.: 16/849,891

(22) Filed: Apr. 15, 2020

(65) Prior Publication Data

US 2020/0334810 A1  Oct. 22, 2020

Related U.S. Application Data

(60) Provisional application No. 62/969,828, filed on Feb. 4, 2020, provisional application No. 62/905,654, filed on Sep. 25, 2019, provisional application No. 62/857,954, filed on Jun. 6, 2019, provisional application No. 62/834,857, filed on Apr. 16, 2019.

(51) Int. Cl.
*G06T 7/00* (2017.01)
*G06T 11/00* (2006.01)
*G16H 30/40* (2018.01)
*G16H 50/20* (2018.01)
*G16H 30/20* (2018.01)

(Continued)

(52) U.S. Cl.
CPC ......... *G06T 7/0012* (2013.01); *G06N 3/0454* (2013.01); *G06N 3/08* (2013.01); *G06T 11/008* (2013.01); *G16H 30/20* (2018.01); *G16H 30/40* (2018.01); *G16H 50/20* (2018.01); *G06T 2200/16* (2013.01); *G06T 2207/10081* (2013.01); *G06T 2207/20081* (2013.01); *G06T 2207/20084* (2013.01); *G06T 2207/30168* (2013.01)

(58) Field of Classification Search
None
See application file for complete search history.

(56) References Cited

U.S. PATENT DOCUMENTS 8,774,560 B2  7/2014  Sugaya
9,298,730 B2  3/2016  Colaco
(Continued)

*Primary Examiner* — Anand P Bhatnagar
(74) *Attorney, Agent, or Firm* — Novel IP

(57) ABSTRACT

A method of training neural networks using digital images is disclosed. Each of the digital images is associated with an imaging modality, an anatomy of a person, a diagnosis of the person, an age of the person, a gender of the person, data indicative of contouring, an aggregated score, or a property of the anatomy of the person. In the method, a client side viewing application receives the digital images, receives a modification of one of the digital images, and transmits the modified digital image to a server. The server selects a neural network to train based on the digital image, trains the selected neural network, receives a request to apply one of the neural networks to another set of digital images, and selects a neural network to apply. The neural network is applied to the other set of digital images and generates a graphical, audio, alphanumeric text, or video result.

30 Claims, 27 Drawing Sheets

(51) Int. Cl.
*G06N 3/04* (2006.01)
*G06N 3/08* (2006.01)

(56) References Cited

U.S. PATENT DOCUMENTS

| | | | |
|---|---|---|---|
| 9,310,981 B2 | 4/2016 | Lynch | |
| 9,659,030 B2 | 5/2017 | Colaco | |
| 9,668,699 B2 * | 6/2017 | Georgescu | G06K 9/6255 |
| 9,769,599 B2 | 9/2017 | Coutinho | |
| 9,947,090 B2 * | 4/2018 | Agam | G06K 9/6256 |
| 9,953,136 B2 | 4/2018 | Dorn | |
| 10,127,662 B1 | 11/2018 | Reicher | |
| 10,169,534 B2 | 1/2019 | Day | |
| 10,380,735 B2 | 8/2019 | Wiemker | |
| 10,460,214 B2 * | 10/2019 | Lu | G06K 9/4671 |
| 10,579,363 B2 | 3/2020 | Kludy | |
| 10,579,877 B2 * | 3/2020 | Guttmann | G06K 9/00335 |
| 10,586,398 B2 | 3/2020 | Wenzel | |
| 2003/0025694 A1 | 2/2003 | Davis | |
| 2005/0021795 A1 | 1/2005 | Kuroshima | |
| 2005/0102315 A1 | 5/2005 | Krishnan | |
| 2010/0077358 A1 | 3/2010 | Sugaya | |
| 2011/0067022 A1 | 3/2011 | Williams | |
| 2014/0108967 A1 | 4/2014 | Markham | |
| 2014/0115020 A1 | 4/2014 | Colaco | |
| 2015/0379209 A1 | 12/2015 | Kusuma | |
| 2016/0071264 A1 * | 3/2016 | Agam | G06K 9/3241 |
| | | | 382/128 |
| 2016/0154941 A1 | 6/2016 | Laborde | |
| 2016/0239615 A1 | 8/2016 | Dorn | |
| 2016/0283085 A1 | 9/2016 | Beausoleil | |
| 2017/0147545 A1 * | 5/2017 | Amoli | G06Q 10/101 |
| 2017/0168692 A1 | 6/2017 | Chandra | |
| 2018/0082487 A1 | 3/2018 | Kiraly | |
| 2018/0349724 A1 | 12/2018 | Xiang | |
| 2019/0065763 A1 | 2/2019 | Berg | |
| 2019/0125298 A1 * | 5/2019 | Abolmaesumi | G06N 3/08 |
| 2019/0130576 A1 | 5/2019 | Wu | |
| 2019/0172581 A1 * | 6/2019 | Zlotnick | G06N 20/00 |
| 2019/0304590 A1 * | 10/2019 | Wilson | G16H 30/20 |
| 2019/0340752 A1 * | 11/2019 | Brestel | G06N 3/08 |
| 2019/0340753 A1 * | 11/2019 | Brestel | G16H 50/30 |
| 2019/0378341 A1 | 12/2019 | Xie | |
| 2019/0394276 A1 * | 12/2019 | Dachille | G06F 3/04842 |
| 2020/0167149 A1 | 5/2020 | Kludy | |

* cited by examiner

FIG. 3B

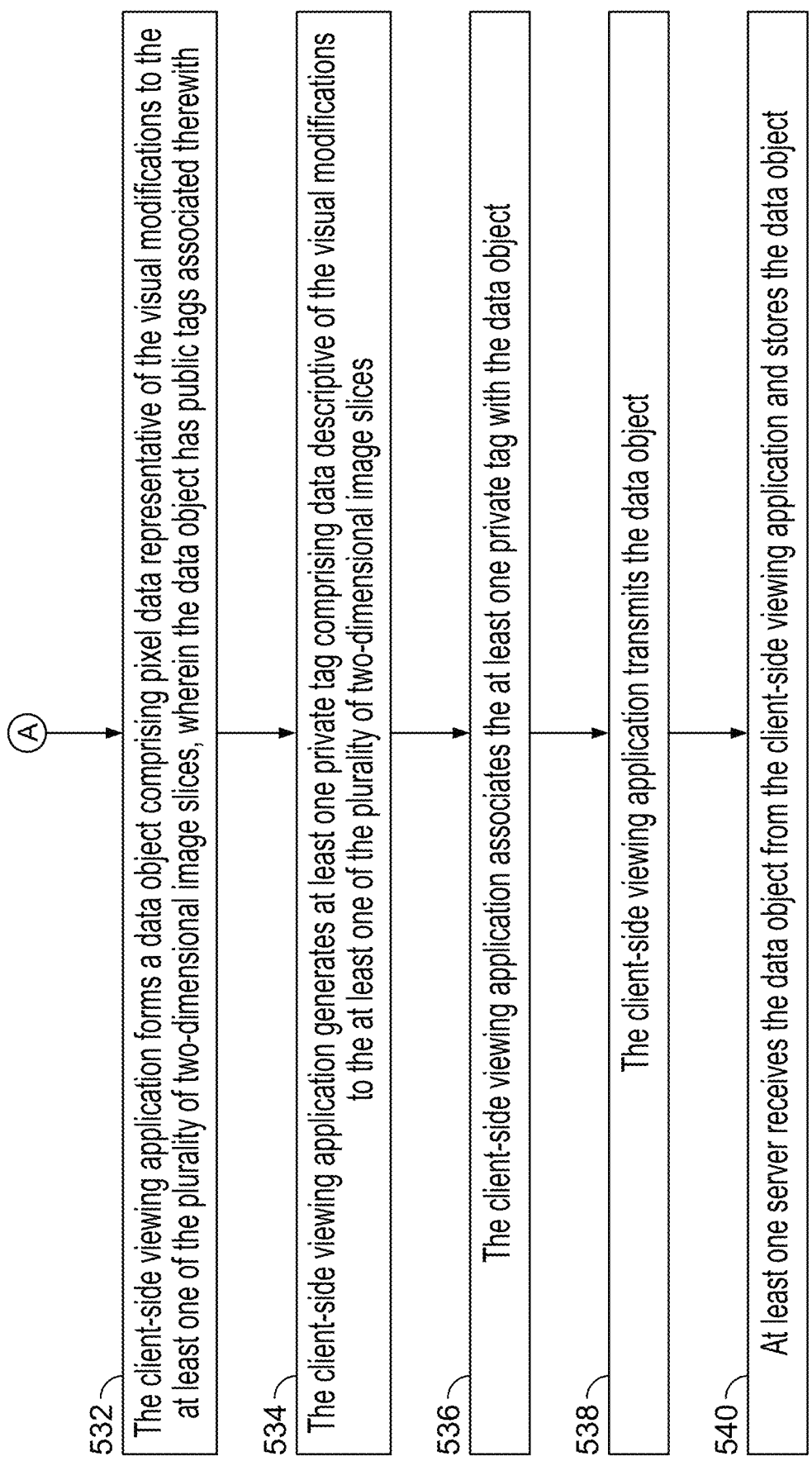
FIG. 5C (Contd.)

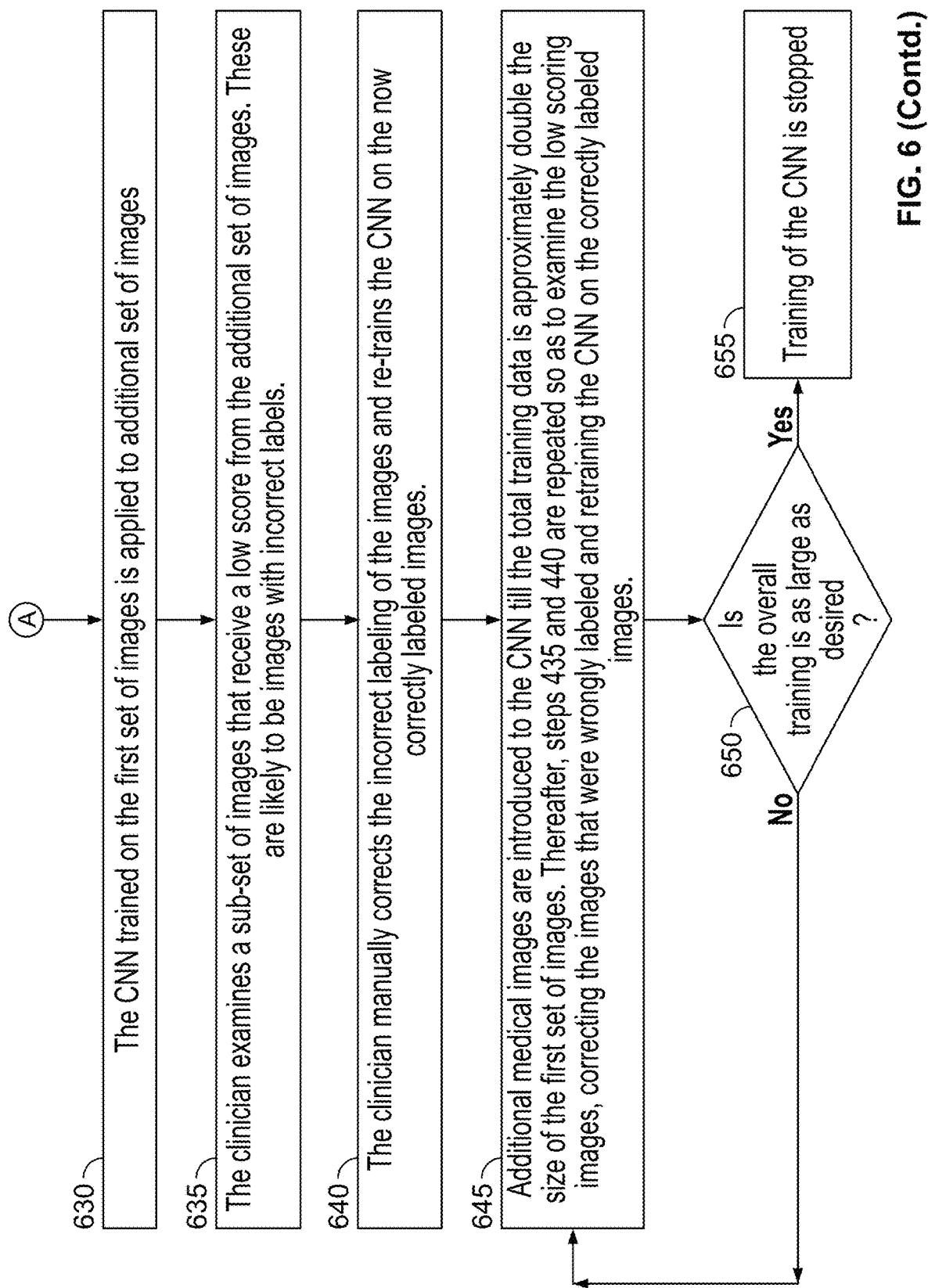
FIG. 6 (Contd.)

FIG. 10

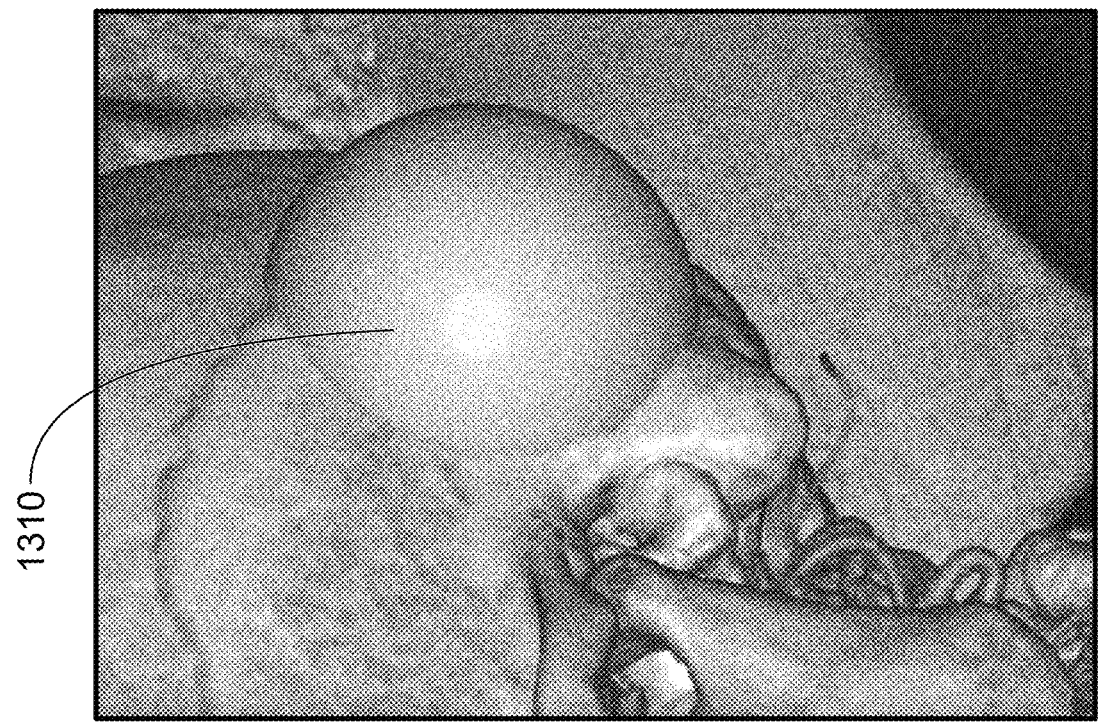
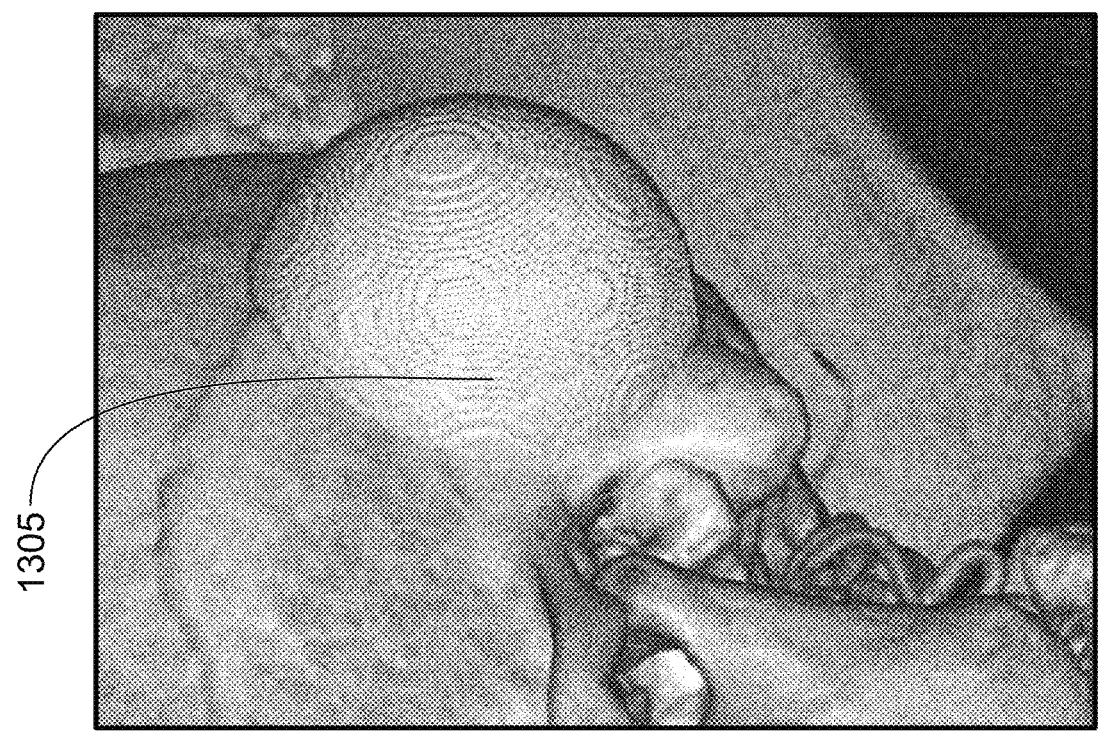
FIG. 13A

METHODS AND SYSTEMS FOR DYNAMICALLY TRAINING AND APPLYING NEURAL NETWORK ANALYSES TO MEDICAL IMAGES

CROSS-REFERENCE

The present application relied on the following applications, for priority, which are herein incorporated by reference in their entirety:

U.S. Patent Provisional No. 62/834,857, entitled "Methods and Systems for Viewing Medical Images", and filed on Apr. 16, 2019;

U.S. Patent Provisional No. 62/857,954, entitled "Systems and Methods for Storing, Processing and Accessing Medical Images in a Serverless Cloud Computing Environment", and filed on Jun. 6, 2019;

U.S. Patent Provisional No. 62/905,654, entitled "Methods and Systems for Viewing Medical Images", and filed on Sep. 25, 2019; and, U.S. Patent Provisional No. 62/969,828, entitled "Systems and Methods for Storing, Processing and Accessing Medical Images in a Serverless Cloud Computing Environment", and filed on Feb. 4, 2020.

FIELD

The present specification is related generally to the field of medical data. More specifically, the present specification is related to systems and methods for storing, processing, accessing and viewing medical image data by providing an end-to-end architecture that enables the rapid synchronization of images, efficient rendering of images on mobile devices, application of image processing functions in a cloud computing environment, training and application of neural network analyses on images, and maintenance and communication of state information for modified images, among other features.

BACKGROUND

Physicians rely on medical image data acquired using medical imaging devices, such as X-ray systems, MRI systems, ultrasound systems, or computed tomography (CT) systems, to make diagnoses or track the progression of a health state of the patient. Conventionally, a physician prescribes one or more of the aforementioned imaging modalities to a patient. Following the prescription, a patient is subjected to one or more of the aforementioned imaging modalities, a technician captures the requested images, and a physician or specialized technician analyses the captured images and generates an image interpretation report, assuming the image has sufficient quality to do so. The image interpretation report, accompanied by associated medical images, is then sent to the requesting physician.

This conventional imaging process has many shortcomings. First, conventionally, such processing or rendering functions are performed using computer workstations that are locally networked with an image storage system and/or the imaging modalities. However, there are several limitations to a workstation-based processing of medical images. For example, the hardware and software involved with these workstations are expensive and require complicated and time consuming installations and maintenance. Because the workstation can only reside in one location, physicians or technicians must physically go to the workstation, often in a hospital or clinic, to use the image processing software and tools, thereby hindering their ability to work remotely. Such limitations could be potentially life threatening in the case of viral pandemic.

Second, assuming this conventional imaging process is implemented using a client-server based architecture that does support the use of viewing applications executing on remote clients, such viewing applications tend to be "thin clients" where the images are rendered at the server and the rendered images are then transmitted and displayed on the viewing applications. This requires the allocation of more computational resources on the server, increases the cost and complexity of server maintenance, and limits the number of simultaneous users that can be accommodated.

As a corollary to the thin client issue, current systems have large latency issues because they attempt to transmit large volumes of medical data over constrained amounts of bandwidth. Image files often have large sizes and require high amounts of bandwidth for communication to a client viewing application. An existing solution to the bandwidth limitation is the application of data compression, such as lossy or lossless compression techniques. The compression of data by existing methods, however, reduces the accuracy, speed of compression, and speed of decompression of the data.

Third, physicians often wish to share a particular view of an image with the patient or another physician. For example, during her review, a physician may manipulate an image by zooming into a particular portion of the image, translating the image, rotating the image, or highlighting a portion of the image. The physician may then wish to share this particular state of the image with a patient. Storing and sharing a modified image, however, is difficult to do in current systems, which typically do not permit visual state information to be maintained after an image is closed in order to avoid complexities with image synchronization Fourth, medical institutions want to benefit from the technical and economic efficiencies of cloud computing but doing so often runs counter to the client-server architectures that have been conventionally implemented. Maintaining image synchronization, especially when multiple users have access to, and can potentially modify, the same images, is challenging, as discussed above. There is a potential for image data sets related to a single patient to be distributed across multiple different cloud computing platforms. Creating a single, cohesive view of such distributed image data sets is currently difficult to achieve, particularly where some cloud platforms recognize a particular image format while other cloud platforms do not recognize or store images in the same format.

Fifth, prior to the diagnostic interpretation or reading of the medical images and/or during the physician's interaction with the medical images, the medical images may be processed using a variety of processing or rendering functions. Advanced processing functions are often computationally intensive and, in a traditional client-server architecture, require dedicating a substantial amount of server resources, on a fixed-basis, to functions which may, or may not, be implemented at a given time. This often limits the medical institution's ability to flexibly apply various image processing functions if and when needed by a physician.

Sixth, existing medical image storage, distribution, and viewing systems do not permit the application of advanced services, such as neural network analyses and intelligent, tailored advertising, on a real-time, on demand basis. For example, conventional advertisement platforms are built on static content. The conventional advertisement platforms analyze the content of the web page ahead of time and they provide, on demand, advertisements based on the text found. Advertisement platforms based on static content have limitations with web viewers such as the one described above since such viewer's page would be considered "empty". The actual content is a study, such as a medical image, viewed by the user and loaded at run time, which would largely be invisible to a conventional advertisement platform in a medical context.

There is therefore a need for methods and systems that enable physicians to share medical images, in a predefined state, with patients without requiring the patient to have to duplicate all the actions required to change the image from its default state to the physician-modified state. There is a need for methods and systems that enable the rapid synchronization of images across multiple cloud services and that allow users to view very bandwidth intensive images with greater accuracy, and very little lag or latency. There is a need for methods and systems that allow a user to access images from multiple discrete cloud service platforms and view them in a consolidated manner. Finally, there is a need for methods and systems that allow for the application of advanced analytical services, based on the dynamic extraction of information viewed by the user in real time, to be applied to images to improve the speed and/or quality of medical diagnoses.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a system for delivering one or more studies, wherein each of the one or more studies comprises a first series of digital images and wherein the first series of digital images are associated with only one person and generated by only one imaging modality of a plurality of imaging modalities, the system comprising: a syncing application, wherein the syncing application is configured to execute within a local area network and wherein the syncing application is in data communication with at least one of the plurality of imaging modalities and/or at least one of a plurality of computing devices configured to display images generated by each of the plurality of imaging modalities; at least one server adapted to be external to the local area network and in data communication with the syncing application; and at least one client-side viewing application adapted to be installed on one or more of said plurality of computing devices external to the local area network, wherein the client-side viewing application is configured to: acquire at least one of the one or more studies, including therein unrendered data representative of the digital images of the first series, from the at least one server; locally render said unrendered data in the one or more of said plurality of computing devices; and enable a user to manipulate at least one of the digital images.

Optionally, the at least one client-side viewing application is configured to transmit the manipulated at least one digital image back to the at least one server and wherein the at least one server is configured to broadcast an availability of the manipulated at least one digital image to the syncing application.

Optionally, the at least one client-side viewing application is configured to transmit the manipulated at least one digital image back to the at least one server and wherein the syncing application is configured to automatically acquire the manipulated at least one digital image from the at least one server.

Optionally, the system further comprises at least one image storage system within the local area network, wherein the syncing application is configured to be a sole gateway to accessing the digital images, stored in the at least one image storage system, outside of the local area network. It should be appreciated that having the syncing application configured to be a sole gateway to accessing the digital images, stored in the at least one image storage system, outside of the local area network is optional. In another embodiment, the syncing application is configured to be one of several gateways to accessing the digital images, stored in the at least one image storage system, outside of the local area network.

Optionally, the one or more studies comprises a second series of digital images, wherein the digital images of the second series is only associated with said one person and generated by a second imaging modality of the plurality of imaging modalities, and wherein the second imaging modality is different than the one imaging modality. It should be appreciated that, in another embodiment, the first and second series of digital images are associated with the same person and are generated by the same imaging modalities, but at different times, including on different days.

Optionally, the one imaging modality of the first series is one of an X-ray scanning system, an ultrasound imaging system, a fluorescence-based imaging system, a mammography system, a positron emission tomography system, a molecular imaging system, a MM system, or a CT system and wherein the second imaging modality is a different one of the X-ray scanning system, the ultrasound imaging system, the fluorescence-based imaging system, the mammography system, the positron emission tomography system, the molecular imaging system, the MM system, or the CT system.

Optionally, each of the digital images in each of the first series and the second series is formatted in a DICOM format.

Optionally, the system further comprises at least one imaging storage system within the local area network, wherein the syncing application is configured to automatically acquire and transmit each of the digital images to the at least one server upon each of the digital images being stored in the at least one imaging system.

Optionally, the syncing application is configured to acquire and transmit each of the digital images to the at least one server upon each of the digital images being modified by a workstation configured within the local area network.

Optionally, the at least one server is configured to apply an image processing function to each of the digital images. Optionally, the image processing function is at least one of an orientation detection, a body part detection, a segmentation function, a decimation function, a point-snap function, an edge-snap function, a contour-sculpting function, a blur detection function, or a propagation function.

Optionally, the at least one server is configured to automatically apply an image processing function to each of the digital images upon receiving each of the digital images, wherein the image processing function is configured to determine a resolution of each of the digital images, wherein the image processing function is configured to generate a notification if the resolution indicates that the image is below a predefined quality level, and wherein the at least one server is configured to cause the notification to be transmitted to the one imaging modality responsible for generating the digital image to which the image processing function was applied.

Optionally, the at least one server comprises a plurality of processing cores and wherein each of the plurality of processing cores is adapted to concurrently host at least 10 separate users while each of the 10 separate users is executing at least one rendering operation using at least ten separate instances of the at least one client-side viewing application.

Optionally, the first series is a computed tomography series comprising the digital images and wherein the client-side viewing application is configured to enable the user to manipulate at least one of the digital images by selecting one of the digital images and applying a degree of zoom to the selected one of the digital images. Optionally, the client-side viewing application is configured to transmit the selected one of the digital images, after manipulation by the user, to the at least one server and wherein the at least one server is configured to automatically store the selected one of the digital images in a manipulated state as a separate file from the selected one of the digital images in a non-manipulated state. Optionally, the at least one server is configured to broadcast a virtual address of the stored selected one of the digital images in the manipulated state. Optionally, the syncing application is configured to query the at least one server for an existence of new digital images and wherein, in response, the at least one server is configured to transmit a virtual address of the stored selected one of the digital images in the manipulated state.

Optionally, the first series is a computed tomography series comprising the digital images and wherein the client-side viewing application is configured to enable the user to manipulate at least one of the digital images by selecting one of the digital images and associating an annotation to the selected one of the digital images. Optionally, the client-side viewing application is configured to transmit the selected one of the digital images, after annotation by the user, to the at least one server and wherein the at least one server is configured to automatically store the selected one of the digital images in an annotated state as a separate file from the selected one of the digital images without said annotation. Optionally, the at least one server is configured to broadcast a virtual address of the stored selected one of the digital images in the annotated state.

Optionally, the client-side viewing application is adapted to generate a graphical interface comprising a plurality of tabs and, when selected, a first of the plurality of tabs is configured to display a profile of the person and a second of the plurality of tabs is configured to display a list of the one or more studies specific to the person. Optionally, when selected, a third of the plurality of tabs is configured to display analyses of the first series of the one or more studies and wherein the analyses are generated by application of a neural network process or machine learning process to the digital images of the first series. Optionally, a first of the one or more studies specific to the person is stored in a first cloud-based network, wherein a second of the one or more studies specific to the person is stored in a second cloud-based network, wherein the first cloud-based network is programmatically separate and distinct from the second cloud-based network, and wherein the second of the plurality of tabs is configured to display the first of the one or more studies and the second of the one or more studies. Optionally, a first of the one or more studies specific to the person is stored in a first cloud-based network, wherein a second of the one or more studies specific to the person is stored in a second cloud-based network, wherein the first cloud-based network is configured to be accessed by a first application program interface, wherein the second cloud-based network is configured to be accessed by a second application program interface that is different from the first application program interface, and wherein at least one of the plurality of tabs is configured to display the second of the one or more studies.

Optionally, the at least one server is configured to apply an orientation image processing process to at least one of the digital images by accessing, through an application program interface having a predefined format, an orientation function executed by a separate server and causing said separate server apply the orientation function to the at least one of the digital images.

Optionally, the at least one server is configured to apply a blur detection image processing process to at least one of the digital images by accessing, through an application program interface having a predefined format, a blur detection function executed by one or more separate servers and causing said one or more separate servers to apply the blur detection function to the at least one of the digital images.

Optionally, the at least one server is configured to apply a neural network or machine learning process to at least one of the digital images by accessing, through an application program interface having a predefined format, a neural network or machine learning function executed by one or more separate servers and causing said one or more separate servers to apply the neural network or machine learning function to the at least one of the digital images.

Optionally, the at least one client-side viewing application is configured to apply an image processing function to each of the digital images wherein the image processing function is at least one of an orientation detection, a body part detection, a segmentation function, a decimation function, a point-snap function, an edge-snap function, a contour-sculpting function, a blur detection function, or a propagation function.

Optionally, the one imaging modality is an X-ray scanning system and the digital images of the first series are defined by a DICOM format, wherein the one or more studies further comprises a second series of digital images formatted in a DICOM format and generated by a CT system imaging modality.

Optionally, the at least one server is configured to automatically apply an image processing function to each of the digital images upon receiving each of the digital images from the syncing application, wherein the image processing function is at least one of an orientation detection, a body part detection, a segmentation function, a decimation function, a point-snap function, an edge-snap function, a contour-sculpting function, a blur detection function, or a propagation function.

Optionally, the system further comprises at least one image storage system in data communication with the local area network and configured to be in data communication with the syncing application via the local area network, wherein the syncing application is configured to be a sole gateway to accessing the digital images, stored in the at least one image storage system, outside of the local area network and through a firewall configured to protect the local area network. Again, as discussed above, the syncing application may also be one of several different gateways to the local network.

The present specification also discloses a method of training a plurality of neural networks using a first set of one or more digital images and providing access to the trained plurality of neural networks, wherein each of the first set of one or more digital images is associated with at least one of an imaging modality, an anatomy of a person, a diagnosis of the person, an age of the person, a gender of the person, data indicative of contouring, an aggregated score, or a property of the anatomy of the person, comprising: receiving, in at least one client-side viewing application, the first set of one or more digital images; receiving, in the at least one client-side viewing application, a modification of the first set of one or more digital images; transmitting the modified first set of one or more digital images to at least one server; selecting one of the plurality of neural networks to train based, at least in part, on the imaging modality, the anatomy of the person, the diagnosis of the person, the age of the person, the gender of the person, data indicative of contouring, the aggregated score, or the property of the anatomy of the person associated with the modified first set of one or more digital images; training the selected neural network based on the modified first set of one or more digital images using the at least one server; receiving, in the at least one client-side viewing application, a request to apply one of the plurality of neural networks to a second set of one or more digital images; in response to the request, selecting one of the plurality of neural networks to apply based, at least in part, on an imaging modality, an anatomy of a person, a diagnosis of the person, an age of the person, a gender of the person, data indicative of contouring, an aggregated score, or a property of the anatomy of the person associated with the second set of the one or more digital images; applying the selected one of the plurality of neural networks to the second set of one or more digital images to generate at least one of a graphical, audio, alphanumeric text, or video result; and displaying or playing the graphical, audio, alphanumeric text, or video result using the client-side viewing application.

Optionally, the imaging modality is at least one of an X-ray scanning system, an ultrasound imaging system, a fluorescence-based imaging system, a mammography system, a positron emission tomography system, a molecular imaging system, a MRI system, or a CT system.

Optionally, the method further comprises selecting a first of the plurality of neural networks to train based on a first imaging modality associated with the modified first set of one or more digital images and selecting a second of the plurality of neural networks to train based on a second imaging modality associated with the modified first set of one or more digital images, wherein the first imaging modality is different from the second imaging modality and wherein the first of the plurality of neural networks is different from the second of the plurality of neural networks.

Optionally, the first imaging modality and the second imaging modality is at least one of an X-ray scanning system, an ultrasound imaging system, a fluorescence-based imaging system, a mammography system, a positron emission tomography system, a molecular imaging system, a MRI system, or a CT system.

Optionally, the modification of the first set of one or more digital images is at least one of an annotation of the first set of one or more digital images, a labeling of the first set of one or more digital images with the imaging modality, a labeling of the first set of one or more digital images with the anatomy of the person, a labeling of the first set of one or more digital images with the diagnosis of the person, a labeling of the first set of one or more digital images with the gender of the person, a labeling of the first set of one or more digital images with the age of the person, a labeling of the first set of one or more digital images with data indicative of contouring, a labeling of the first set of one or more digital images with the aggregated score, a labeling of the first set of one or more digital images with the property of the anatomy of the person, an association of one or more visible features in the first set of one or more digital images with a disease state of the person, a visible highlighting of one or more visible features of the first set of one or more digital images with the disease state of the person, a measurement of visible features in the first set of one or more digital images, or a change in an orientation, color, zoom, rotation, brightness, or saturation in the first set of one or more digital images.

Optionally, the plurality of neural networks is at least one of a deep feed forward network, a perceptron network, a feed forward network, a radial basis network, a recurrent neural network, a long term memory network, a short term memory network, a gated recurrent unit network, an auto encoder network, a variational auto encoder network, a denoising auto encoder network, a sparse auto encoder network, a Markov chain network, a Hopfield network, a Boltzmann machine network, a restricted Boltzmann machine network, a deep belief network, a deep convolutional network, a deconvolutional network, a deep convolutional inverse graphics network, a generated adversarial network, a liquid state machine, an extreme learning machine, an echo state network, a deep residual network, a Kohonen network, a support vector machine network, a neural Turing machine network, or a convolutional neural network with transfer learning network.

Optionally, each of the first set of one or more digital images is in a DICOM format, wherein each of the first set of one or more digital images comprises one or more tags, and wherein the one or more tags of each of the first set of one or more digital images comprises data indicative of the imaging modality, the anatomy of a person, the diagnosis of the person, the age of the person, the gender of the person, data indicative of contouring, the aggregated score, or the property of the anatomy of the person.

Optionally, the selecting of one of the plurality neural networks to apply in response to the request is performed by the client-side viewing application and is based, at least in part, on the imaging modality associated with the second set of one or more digital images.

Optionally, the selecting of one of the plurality neural networks to apply in response to the request is performed by the at least one server and is based, at least in part, on the diagnosis of the person associated with the second set of one or more digital images.

Optionally, the selecting of one of the plurality neural networks to apply in response to the request is performed by the client-side viewing application and is based, at least in part, on the anatomy of the person associated with the second set of one or more digital images.

Optionally, the selecting of one of the plurality neural networks to apply in response to the request is performed by the at least one server and is based, at least in part, on data indicative of contouring associated with the second set of one or more digital images.

Optionally, after selecting one of the plurality of neural networks to train and before training the selected neural network, the at least one server applies a quality check function to the modified first set of one or more digital images.

Optionally, the at least one server selects one of the plurality of neural networks to train based, at least in part, on data in one or more DICOM tags associated with the modified first set of one or more digital images.

Optionally, the selection of the plurality of neural networks to apply to the second set of one or more digital images is based, at least in part, on data in one or more DICOM tags associated with the second set of one or more digital images.

Optionally, the training comprises modifying a topology of the selected neural network.

Optionally, the training comprises modifying a weight associated with one or more nodes of the selected neural network.

Optionally, the training comprises modifying a number or ordering of one or more layers of the selected neural network.

Optionally, the method further comprises selecting a first of the plurality of neural networks to train based on a first imaging modality associated with a first of the modified first set of one or more digital images and selecting a second of the plurality of neural networks to train based on a second imaging modality associated with a second of the modified first set of one or more digital images, wherein the first imaging modality and the second imaging modality are different from each other and are at least one of an X-ray scanning system, an ultrasound imaging system, a fluorescence-based imaging system, a mammography system, a positron emission tomography system, a molecular imaging system, a MRI system, or a CT system, and wherein a topology of the first of the plurality of neural networks is different from a topology of the second of the plurality of neural networks.

Optionally, each of the second set of one or more digital images represents a slice of a three-dimensional image and is associated with a computed tomography imaging modality.

Optionally, the at least one client-side viewing application, receives a modification of one slice of the three-dimensional image and wherein the selected one of the plurality of neural networks applied to the second set of one or more digital images is configured to propagate the modification to other slices in the three-dimensional image. Optionally, when the at least one client-side viewing application receives a modification of one slice of the three-dimensional image, analyzes gradients that represent a transition in a degree of pixel brightness, where the gradients or transitions must occur within a certain pixel distance around the received modification, identifies the gradient which represents an expected brightness transition, and then propagates that modification to the associated location of the identified gradient, such as by associating a visual line with that associated location. It should be appreciated that the expected brightness transition may be the steepest or strongest gradient which represents the biggest transition in brightness.

Optionally, the modification is a visual highlight of an edge of an anatomical feature in said slice and wherein the propagation of the modification to other slices in the three-dimensional image causes said visual highlight of the edge of the anatomical feature to appear in the other slices of the three-dimensional image without manual intervention.

Optionally, each of the second set of one or more digital images is associated with at least one series, wherein each of the at least one series is associated with at least one study, and wherein the at least one study is associated with only one person and with only one imaging modality. Optionally, the at least one client-side viewing application is configured to generate a graphical user interface comprising a listing of the at least one study and at least one of the graphical, audio, alphanumeric text, or video result. Optionally, the at least one client-side viewing application is configured to generate a graphical user interface comprising a listing of the at least one study and a link to the at least one of the graphical, audio, alphanumeric text, or video result.

Optionally, the at least one server selects one of the plurality of neural networks to train automatically upon receiving the modified first set of one or more digital images and determining data in at least one DICOM tag associated with the modified first set of one or more digital images.

Optionally, the at least one server is configured to receive the modified first set of one or more digital images from a first client-side viewing application controlled by a first user and is configured to receive a modified third set of one or more digital images from a second client-side viewing application controlled by a second user and wherein the first user is different from the second user. Optionally, the first client-side viewing application is configured to execute in a first local area network and wherein the second client-side viewing application is configured to execute in a second local area network and wherein the first local area network is separated from the second local area network by at least one firewall.

Optionally, each of the second set of one or more digital images represents a portion of a multi-image data set of one person acquired at a same time and using a same imaging modality. Optionally, the at least one client-side viewing application, receives a modification of one portion of the multi-image data set and wherein the selected one of the plurality of neural networks applied to the second set of one or more digital images is configured to propagate the modification to other portions in the multi-image data set. Optionally, the modification is a visual identification of an anatomical feature in said one portion and wherein the propagation of the modification to other portions in the multi-image image data set causes said visual identification of the anatomical feature to be associated with said anatomical feature in the other portions of the multi-image data set.

The present specification also discloses a system for electronically receiving, modifying and distributing a three-dimensional image, comprising: an image viewer application configured to execute on a computing device, wherein, when executed on the computing device, the image viewer application: receives data representative of the three-dimensional image in a first state; reconstructs the data representative of the three-dimensional image in the first state to form a plurality of two-dimensional image slices; displays the plurality of two-dimensional image slices; provides a user with a plurality of options to modify at least one of the plurality of two-dimensional image slices; receives input, responsive to the plurality of options, from the user to visually modify at least one of the plurality of two-dimensional image slices; visually modifies at least one of the plurality of two-dimensional image slices, in response to the received input, to form visual modifications to the at least one of the plurality of two-dimensional image slices; forms a data object referencing pixel data representative of the visual modifications to the at least one of the plurality of two-dimensional image slices, wherein the data object has public tags associated therewith; generates at least one private tag comprising data descriptive of the visual modifications to the at least one of the plurality of two-dimensional image slices; associates the at least one private tag with the data object; and transmits the data object; and, a server configured to receive said data object from the image viewer application and store said data object in an image storage system.

Optionally, the data object is a grayscale softcopy presentation state (GSPS) object.

Optionally, the public tags are readable by any viewer configured to read, render, or display the data object.

Optionally, the at least one private tag is only readable by a viewer configured to read, render, or display the data object and configured to have permission to access to the at least one private tag.

Optionally, the server is configured to publish a link to an address, wherein the address is indicative of a memory location of the data object.

Optionally, the server is configured to be responsive to a request for a link to an address, wherein the address is indicative of a memory location of the data object.

Optionally, when executed on the computing device, the image viewer application receives data representative of the three-dimensional image in an unrendered state.

Optionally, when executed on the computing device, the image viewer application displays the plurality of two-dimensional image slices by rendering the plurality of two-dimensional image slices.

Optionally, when executed on the computing device, the image viewer application reconstructs the data representative of the three-dimensional image using Multi-Planar Reformat and wherein a portion of the plurality of two-dimensional images are representative of at least a sagittal, coronal, or oblique view of the three-dimensional image.

Optionally, the server is configured to store the data object without overwriting the three-dimensional image in the first state.

Optionally, the plurality of options provided by the image viewer application comprises at least one of modifying a view direction of the plurality of two-dimensional image slices, modifying a cutting plane of the plurality of two-dimensional image slices, modifying values indicative of the opacity, transparency, or color of the plurality of two-dimensional image slices, modifying an orientation of one or more of the plurality of two-dimensional image slices, or modifying data indicative of a degree of pan or zoom of one or more of the plurality of two-dimensional image slices.

Optionally, the plurality of options provided by the image viewer application includes a contouring tool, wherein, when executed by the user, the contouring tool is configured to visually identify edges of an anatomical region of interest in at least one of the plurality of two-dimensional images.

Optionally, when executed, the image viewer application propagates the visual identification of the edges of the anatomical region of interest in the at least one of the plurality of two-dimensional images to a remaining portion of the plurality of two-dimensional images to thereby visually identify edges of the anatomical region of interest in the remaining portion of the plurality of two-dimensional images.

Optionally, when executed, the image viewer application automatically propagates said visual identification without further manual intervention upon a completed execution of the contouring tool.

Optionally, when executed, the image viewer application is configured to apply a virtual light source to a portion of the plurality of two-dimensional image slices to thereby cast a shadow on voxels in the portion of the plurality of two-dimensional image slices. It should be appreciated that this approach, namely configuring the image viewer application to apply a virtual light source to a portion of the plurality of two-dimensional image slices to thereby cast a shadow on voxels in the portion of the plurality of two-dimensional image slices may be performed without any of the aforementioned other limitations. More generally, the limitations disclosed herein may be independently deployed, relative to other limitations, unless otherwise indicated.

Optionally, when executed, the image viewer application is configured to generate a depth map indicative of a location, along a Z axis normal to a two dimensional plane defining the plurality of two-dimensional image slices, of each voxel in the plurality of two-dimensional image slices.

Optionally, when executed, the image viewer application is configured to determine which voxels in the plurality of two-dimensional image slices are encompassed by said shadow.

Optionally, when executed, the image viewer application is configured to assign an opacity value to at least a portion of the voxels based upon determining which voxels in the plurality of two-dimensional image slices are encompassed by said shadow.

Optionally, at least one of the image viewer application or the server is configured to generate an encrypted token comprising an identity of a location of the data object stored in the image storage system.

Optionally, at least one of the image viewer application or the server is configured to generate within the encrypted token additional data wherein the additional data comprises at least one of a password, an expiration date of a link to the location of the data object, or an identity of the user associated with the data object.

Optionally, the system further comprises a second image viewer application, wherein, when executed, the second image viewer application is configured to receive a virtual address to the data object.

Optionally, when executed, the second image viewer application is configured to retrieve the data object using the virtual address.

Optionally, when executed, the second image viewer application is configured to render the data object and access data in the at least one private tag.

Optionally, when executed, the second image viewer application is configured to apply data descriptive of the visual modifications, accessed from the at least one private tag, to the data object.

Optionally, the data object is a modified version of the three-dimensional image.

Optionally, when executed, the image viewer application is configured to modify values indicative of the opacity, transparency, or color of the at least one of the plurality of two-dimensional image slices in response to the received input to form visual modifications to the at least one of the plurality of two-dimensional image slices.

Optionally, when executed, the image viewer application is configured to modify values indicative of a degree of pan or zoom of the at least one of the plurality of two-dimensional image slices in response to the received input to form visual modifications to the at least one of the plurality of two-dimensional image slices.

Optionally, when executed, the image viewer application is configured to modify values indicative of an orientation of the at least one of the plurality of two-dimensional image slices in response to the received input to form visual modifications to the at least one of the plurality of two-dimensional image slices.

Optionally, when executed, the image viewer application is configured to modify values indicative of a view direction of the at least one of the plurality of two-dimensional image slices in response to the received input to form visual modifications to the at least one of the plurality of two-dimensional image slices.

Optionally, the data object references the pixel data by referencing a virtual address where the pixel data is located and wherein the data object does not comprise the pixel data.

The present specification also discloses a system for electronically modifying a three-dimensional image, comprising: an image viewer application configured to execute on a computing device, wherein, when executed on the computing device, the image viewer application: receives data representative of the three-dimensional image in a first state; reconstructs the data representative of the three-dimensional image in the first state to form a plurality of two-dimensional image slices; displays the plurality of two-dimensional image slices; provides a user with a plurality of options to modify at least one of the plurality of two-dimensional image slices, wherein the plurality of options provided by the image viewer application includes a contouring tool and wherein, when executed by the user, the contouring tool is configured to visually identify edges of an anatomical region of interest in at least one of the plurality of two-dimensional images; receives input, responsive to the plurality of options, from the user to visually modify at least one of the plurality of two-dimensional image slices, wherein said input is a visual identification of edges of the anatomical region of interest in at least one of the plurality of two-dimensional images; visually modifies at least one of the plurality of two-dimensional image slices, in response to the received input, to form visual modifications to the at least one of the plurality of two-dimensional image slices, wherein, when executed, the image viewer application propagates the visual identification of the edges of the anatomical region of interest in the at least one of the plurality of two-dimensional images to a remaining portion of the plurality of two-dimensional images to thereby visually identify edges of the anatomical region of interest in the remaining portion of the plurality of two-dimensional images; forms a data object comprising pixel data representative of the visual modifications to the at least one of the plurality of two-dimensional image slices, wherein the data object has public tags associated therewith; and transmits the data object; and, a server configured to receive said data object from the image viewer application and store said data object in an image storage system.

Optionally, when executed, the image viewer application automatically propagates said visual identification without further manual intervention upon a completed execution of the contouring tool.

Optionally, when executed on the computing device, the image viewer application receives data representative of the three-dimensional image in an unrendered state.

Optionally, when executed on the computing device, the image viewer application displays the plurality of two-dimensional image slices by rendering the plurality of two-dimensional image slices.

Optionally, when executed on the computing device, the image viewer application reconstructs the data representative of the three-dimensional image using Multi-Planar Reformat and wherein a portion of the plurality of two-dimensional images are representative of at least a sagittal, coronal, or oblique view of the three-dimensional image.

Optionally, the server is configured to store the data object without overwriting the three-dimensional image in the first state.

The present specification also discloses a system for electronically modifying a three-dimensional image, comprising: an image viewer application configured to execute on a computing device, wherein, when executed on the computing device, the image viewer application: receives data representative of the three-dimensional image in a first state; reconstructs the data representative of the three-dimensional image in the first state to form a plurality of two-dimensional image slices; displays the plurality of two-dimensional image slices; applies a virtual light source to a portion of the plurality of two-dimensional image slices to thereby cast a shadow on voxels in the portion of the plurality of two-dimensional image slices; generates a depth map indicative of a location, along a Z axis normal to a two dimensional plane defining the plurality of two-dimensional image slices, of each voxel in the plurality of two-dimensional image slices; determines which voxels in the plurality of two-dimensional image slices are encompassed by said shadow; and assigns at least one of a transparency or opacity value to at least a portion of the voxels based upon determining which voxels in the plurality of two-dimensional image slices are encompassed by said shadow.

The aforementioned and other embodiments of the present shall be described in greater depth in the drawings and detailed description provided below.

BRIEF DESCRIPTION OF THE DRAWINGS

These and other features and advantages of the present specification will be further appreciated, as they become better understood by reference to the following detailed description when considered in connection with the accompanying drawings:

FIG. 3B illustrates another exemplary screenshot of a federated view built by built by the caching and syncing application, in accordance with some embodiments of the present specification;

FIG. 10 illustrates a "patient jacket" GUI disclosing a neural network analysis of an acquired image, in accordance with some embodiments of the present specification

FIG. 13A shows first and second rendered appearances of a volume of interest (VOI), in accordance with some embodiments of the present specification;

DETAILED DESCRIPTION

Figure 1:
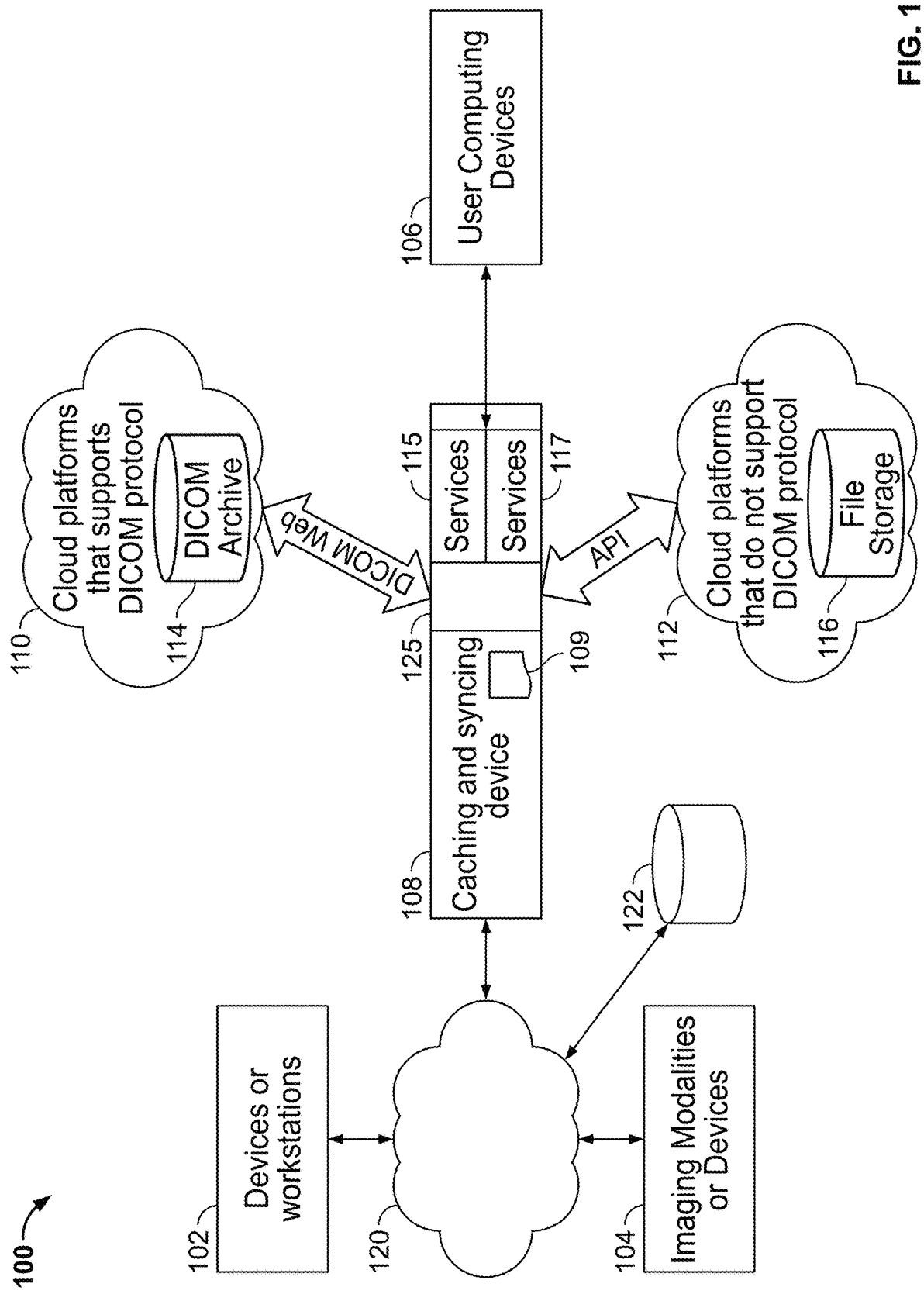
FIG. 1 illustrates an exemplary system environment for deploying methods and systems in accordance with some embodiments of the present specification.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

As used herein, the indefinite articles "a" and "an" mean "at least one" or "one or more" unless the context clearly dictates otherwise.

In various embodiments, a computing device includes an input/output controller, at least one communications interface; and a system memory. The system memory includes at least one random access memory (RAM) and at least one read-only memory (ROM). These elements are in communication with a central processing unit (CPU) to enable operation of the computing device. In various embodiments, the computing device may be a conventional standalone computer or alternatively, the functions of the computing device may be distributed across a network of multiple computer systems and architectures. In some embodiments, the computing device is a diagnostic workstation that a physician, radiologist or a caregiver may use to view and interact with a medical image. In some embodiments, the computing device is a technician workstation that an operator of a medical imaging device uses to capture relevant medical images.

In some embodiments, execution of a plurality of sequences of programmatic instructions or code enable or cause the CPU of the computing device to perform various functions and processes. In alternate embodiments, hardwired circuitry may be used in place of, or in combination with, software instructions for implementation of the processes of systems and methods described in this application. Thus, the systems and methods described are not limited to any specific combination of hardware and software.

The term "function" used in this disclosure may refer to computer logic utilized to provide a desired functionality, service, or operation by programming or controlling a general purpose processor. In various embodiments, a function can be implemented in hardware, firmware, software or any combination thereof. The function may be interchangeably used with unit, logic, logical block, component, or circuit, for example. The function may be the minimum unit, or part thereof, which performs one or more particular functions.

In the present disclosure, an image, or a digital image, is a visual data set composed of picture elements, known as pixels, each with finite, discrete quantities of numeric representation for its intensity or gray level that is an output from its two-dimensional functions fed as input by its spatial coordinates denoted with x, y on the x-axis and y-axis, respectively.

Digital Imaging and Communications in Medicine (DICOM) is the international standard for medical images and related information. It defines the formats for medical images that can be exchanged with the data and quality necessary for clinical use. DICOM is implemented in most radiology, cardiology imaging, and radiotherapy devices (X-ray, CT, MM, ultrasound, etc.), and increasingly in devices in other medical domains such as ophthalmology and dentistry. A DICOM data object comprises a number of attributes, including items such as patient name and ID, and also a special attribute containing the image pixel data. A single DICOM object has only one attribute containing pixel data. For many modalities, this corresponds to a single image. However, the attribute may contain multiple "frames", allowing storage of cine loops or other multi-frame data. In these cases, three- or four-dimensional data can be encapsulated in a single DICOM object. Pixel data can be compressed using a variety of standards, including JPEG, Lossless JPEG, JPEG 2000, and Run-length encoding (RLE).

To promote identical grayscale image display on different monitors and consistent hard-copy images from various printers, the DICOM offers a lookup table to display digitally assigned pixel values. To use the DICOM grayscale standard display function (GSDF), images must be viewed (or printed) on devices that have this lookup curve or on devices that have been calibrated to the GSDF curve. An application for primary processing and preservation of medical images in DICOM format, commonly known as DICOM viewer or just 'viewer', is required to view the DICOM images. Viewers are conventionally equipped with tools to manipulate DICOM images and typically have a user interface.

The DICOM standard provides some limited services, including a storage service to send images or other persistent objects (structured reports, etc.) to a picture archiving and communication system (PACS) or workstation. PACS is used to securely store and digitally transmit medical images. Medical documentation and images are typically housed in off-site servers and accessed using PACS workstations. PACS has four major components: hardware imaging machines, a secure network for the distribution and exchange of patient images, a workstation or mobile device for viewing, processing and interpreting images, and electronic archives for storing and retrieving images and related documentation and reports.

The DICOM format includes a plurality of different tags which can be used to associate specific diagnostic, anatomical, or patient information with the image. For example, patient identifiers may be used as DICOM names, i.e. a file of a chest X-ray image may contain a patient identifier (ID) within the file, so that the image can never be separated from this information by mistake.

The term "series" refers to an organized combination of digital images. For example, a CT scan is defined by a series, which is a set of related digital images. Similarly, a PET scan is defined by a series, which is a set of related digital images. Various series may be combined into a "study" related to a patient. Typically, a physician may contemporaneously order various tests that may yield different series (PET scan is one series, CT scan is another series, for example) and those series may be organized into a study specific to the patient for whom the orders were made. The term "priors" refers to previous studies that were performed for that patient. It should be appreciated that a series is typically defined by a single imaging modality (such as a CT system, X-ray system, ultrasound system, MRI system) in relation to a single patient. A series may also be further defined by anatomy. For example, all axial images acquisitions of the chest may be grouped in one series, while all brain image acquisitions may be grouped into a second series. Furthermore, other criteria may be used to group images into series, for example acquisitions with and without contrast agents may be grouped into different series. In all cases, however, a series comprises images generated by a single imaging modality in relation to a single patient and a study comprises images related to a single patient.

Overview

FIG. 1 illustrates an exemplary system environment 100 for deploying methods and systems in accordance with some embodiments of the present specification. Referring to FIG. 1, in some embodiments, client-side systems may include one or more computing devices 102, one or more medical imaging devices or modalities 104, and one or more user computing devices 106. Devices 102 may include legacy systems, hospital information systems (HIS), computing devices used by clinicians, legacy PACS systems, or any other systems that may be used to upload and/or view medical information such as medical images by medical professionals.

The one or more imaging devices or modalities 104 comprise one of an X-ray scanning system, an ultrasound imaging system, a fluorescence-based imaging system, a mammography system, a positron emission tomography system, a molecular imaging system, a MRI system, a CT system, radiological information systems (RIS), or other acquisition systems that generate medical images and related information.

User computing devices 106 may include computing devices such as desktops, laptops, personal digital assistants (PDAs), mobile phones, or any other wired or wireless computing device that enables users such as patients, doctors, and related personnel to view DICOM information, view Electronic Medical Records (EMRs), and specifically in accordance with the various embodiments of the present specification, view aggregated DICOM information generated from multiple sources including multiple devices 102, medical imaging devices 104, which may be a computed tomography (CT) scanner or X-ray scanner for example, and from multiple cloud platforms such as, for example, first and second cloud computing platforms or systems 110, 112.

The user computing devices 106 may also include functionalities to display a list of images to the user operating a device 106 and allow selection (user input) of the images to display. Devices 106 are also configured to retrieve the data requested, which may include images, user preferences and possibly other information available, and perform manipulation of the images displayed as requested by the user. The manipulation of images may involve, for example, panning, zooming, adjusting the contrast, annotating, or any other type of image manipulation.

Accordingly, in some embodiments, some or all of the user computing devices 106 have a client-side viewing application installed that is configured to generate one or more GUIs (Graphical User Interfaces) that render, and enable a user to view and manipulate, DICOM data (such as images and EMRs, for example) on a display associated with each of the user computing devices 106. In some embodiments, the client-side viewing application uses a web browser employing HTML to display the DICOM images. In some embodiments, some or all of the user computing devices 106 may have a legacy browser application, such as, for example, Internet Explorer or Google Chrome, to enable a user to view DICOM data. However, unlike the novel client-side viewing applications disclosed herein, these legacy browser applications do not have the functionalities to enable the user to render and then manipulate the locally rendered DICOM data. Thus, the present specification recognizes a scenario where some of the user computing devices 106 may implement the client-side viewing applications configured to locally render the DICOM data while some of the other user computing devices 106 may implement the legacy browser applications which require server-side rendering to function.

It should be appreciated that the images or digital images, that may be retrieved and rendered for display using a client-side viewing application or a legacy browser on a device 106, may be associated with at least one 'series' wherein a plurality of series may be part of a 'study' related to a patient.

In accordance with some aspects of the present specification, the one or more computing devices 102, medical imaging devices 104 along with a caching and syncing device 108 and at least one image storage system 122 are in data communication with each other over a local area network (LAN) 120. In embodiments, the device 108 has a caching and syncing application 109 installed that is configured to execute within the local area network 120 thereby placing the caching and syncing application 109 in data communication with the one or more computing devices 102, medical imaging devices 104 and the at least one image storage system 122. In some embodiments, the at least one image storage system 122 is DICOM compliant. In some embodiments, the LAN 120 implements a network security system or firewall. In various embodiments, the LAN 120 may be associated with a care-giving facility such as a hospital, a patient scanning facility or any other medical care center as would be evident to persons of ordinary skill in the art.

In accordance with another aspect of the present specification, the caching and syncing device 108 is in data communication with at least one server 125 that is adapted to be external to the LAN 120. Similarly, the one or more user computing devices 106 are also in data communication with the at least one server 125. In various embodiments, the caching and syncing device 108 and the one or more user computing devices 106 are in data communication with the at least one server 125 over a private or public network (such as the Internet). In some embodiments, the at least one server 125 is in data communication with the first and second cloud computing platforms or systems 110, 112.

In embodiments, the caching and syncing device 108 is configured as a sole gateway to enable operators and/or users of the one or more computing devices 102 and medical imaging devices 104 to communicate (access/retrieve and/or upload/store) DICOM information with the first and second cloud computing platforms or systems 110, 112 through the at least one server 125. It should be appreciated, however, that in some embodiments, the at least one server 125 is implemented within the cloud platforms 110, 112 (such as the first layer 205 of the cloud computing system 200 of FIG. 2A). Alternatively, in some embodiments, the at least one server 125 may be a dedicated standalone server (that is not in data communication with a cloud platform).

In some embodiments, the at least one server 125 comprises a plurality of processing cores and wherein each of the plurality of processing cores is adapted to concurrently host at least 10 separate users while each of the 10 separate users is executing at least one rendering operation using at least ten separate instances of at least one client-side viewing application.

In embodiments, the first cloud computing platform or system 110 provides a plurality of programmatic services that support the DICOM protocol while the second cloud computing platform or system 112 provides a plurality of programmatic services that do not support DICOM protocol. Platforms that support the DICOM protocol are configured to execute DICOMWeb, which is the DICOM standard for web-based medical imaging. DICOMWeb can be implemented directly or as a proxy to DICOM message service element (DEVISE) services to offer web-based access to DICOM-enabled systems. Examples of cloud platforms 110 include Google Cloud Platform (GCP) and Microsoft Azure. In situations where a cloud platform does not offer or implement a DICOM protocol, the cloud platform may, instead, offer an application program interface that may be tailored and used by the at least one server 125. Examples of cloud platforms 112 that do not implement a DICOM protocol include, for example, Amazon Web Services (AWS). In implementations, therefore, the caching and syncing application 109 may interface with the at least one server 125 that in turn may interface with the first cloud computing platform 110 such as Google Cloud Platform (GCP), Microsoft Azure and/or with the second cloud computing platform 112 such as Amazon Simple Storage Service (S3) API for storage, in accordance with the various embodiments of the present specification. In another embodiment, the caching and syncing device 108 comprises the server 125 that is responsible for communicating with one or more servers configured to use a DICOM Web application programming interface and with one or more servers configured to use an application programming interface that is not DICOM Web or DICOM Web compatible. Furthermore, the caching and syncing device 108 comprises the server 125 that is responsible for converting data between a) one or more servers configured to use a DICOM Web application programming interface and b) one or more servers configured to use an application programming interface that is not DICOM Web or DICOM Web compatible. It should be appreciated that the server 125 may be an application in the caching and syncing device 109, a part of the caching and syncing application 109, or a separate, standalone physical server or network of servers.

The first cloud computing platform or system 110 may include a DICOM archive 114. The DICOM archive 114 is configured to store instances of DICOM data in the cloud. The archive 114 is configured to consolidate disparate or fragmented imaging systems into one repository, increase data integrity and enable and simplify access to patient medical data and images by devices 106. Different types of archive solutions may be available for DICOM data on different cloud platforms 110 and 112. It should be noted that embodiments of the present specification may be applicable to other types of images other than DICOM images; thus, DICOM images are referred to herein by example only. Similar to DICOM archive 114, cloud platforms 112 include file storage 116 to store DICOM data through, and in accordance with, their APIs.

The first and second cloud platforms 110, 112 interface with services such as services 115 and 117, respectively, which generate data representative of HTML pages for display within the client-side viewing applications or legacy browsers of user computing devices 106, as well as providing discrete functionalities such as storing/retrieving user preferences, enforcing security, and supporting machine learning (ML) services. Once meta information is parsed from the DICOM images and saved into objects that may be presented to, and within, a client-side viewing application or legacy browser, in order to provide the user with a version of the DICOM image that is viewable within the client-side viewing application or legacy browser at user device 106, pixel data from the DICOM image is converted into a web digestible format by services 115 and 117.

In various embodiments, the services 115 may be implemented in the at least one server 125 or its functionalities are added to the cloud platform 110 using serverless technologies. The programmatic instructions comprising services 115 may be configured to perform user validation, security and storing/retrieval of user preferences. The programmatic instructions comprising services 115 may be further configured to perform data conversion from DICOM Web, such as for example to generate image thumbnails, and caching of the data, to index files in storage 114 such that users of devices 106 can retrieve the images in a short amount of time, to convert data for the images in file storage 114 such that the content can be displayed by the client-side viewing application or legacy browser in device 106, and/or to perform caching of the data converted to improve performances.

Similarly, services 117 may be implemented by in the at least one server 125 or its functionalities are added to the cloud platform 112 using serverless technologies. The programmatic instructions comprising services 117 may be configured to perform user validation, security and storing/retrieval of user preferences. The programmatic instructions comprising services 117 may be further configured to perform data manipulations, such as for example generating image thumbnails or caching of the data, to index files in storage 116 such that users of devices 106 can retrieve the images in a short amount of time, to convert data for the images in file storage 116 such that the content can be displayed by the client-side viewing application or legacy browser in device 106, and/or to perform caching of the data converted to improve performances.

Figure 2A:
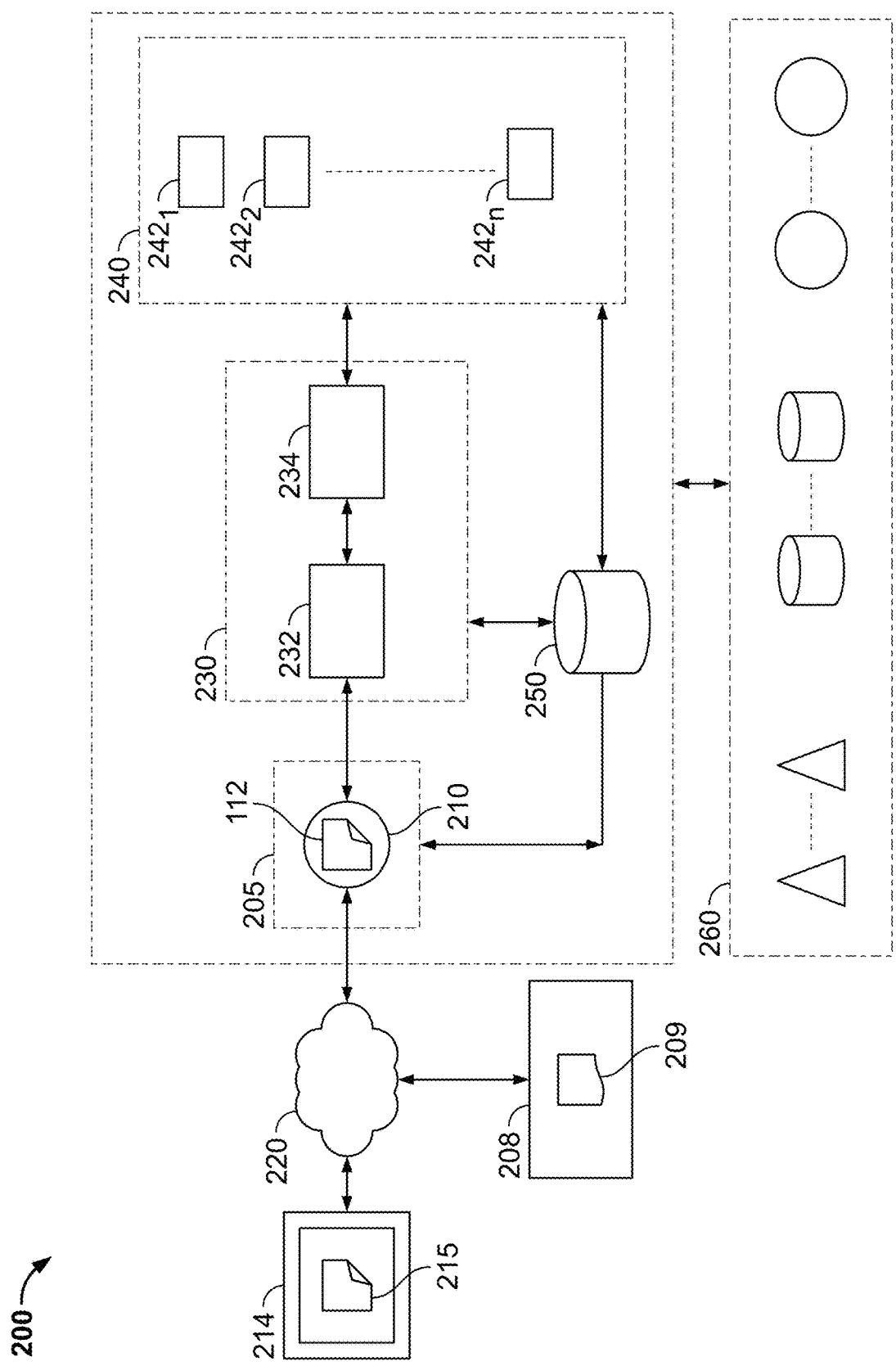
FIG. 2A is a block diagram illustration of a serverless cloud computing environment to provide storage, access and processing services, in accordance with some embodiments of the present specification.
Figure 2B:
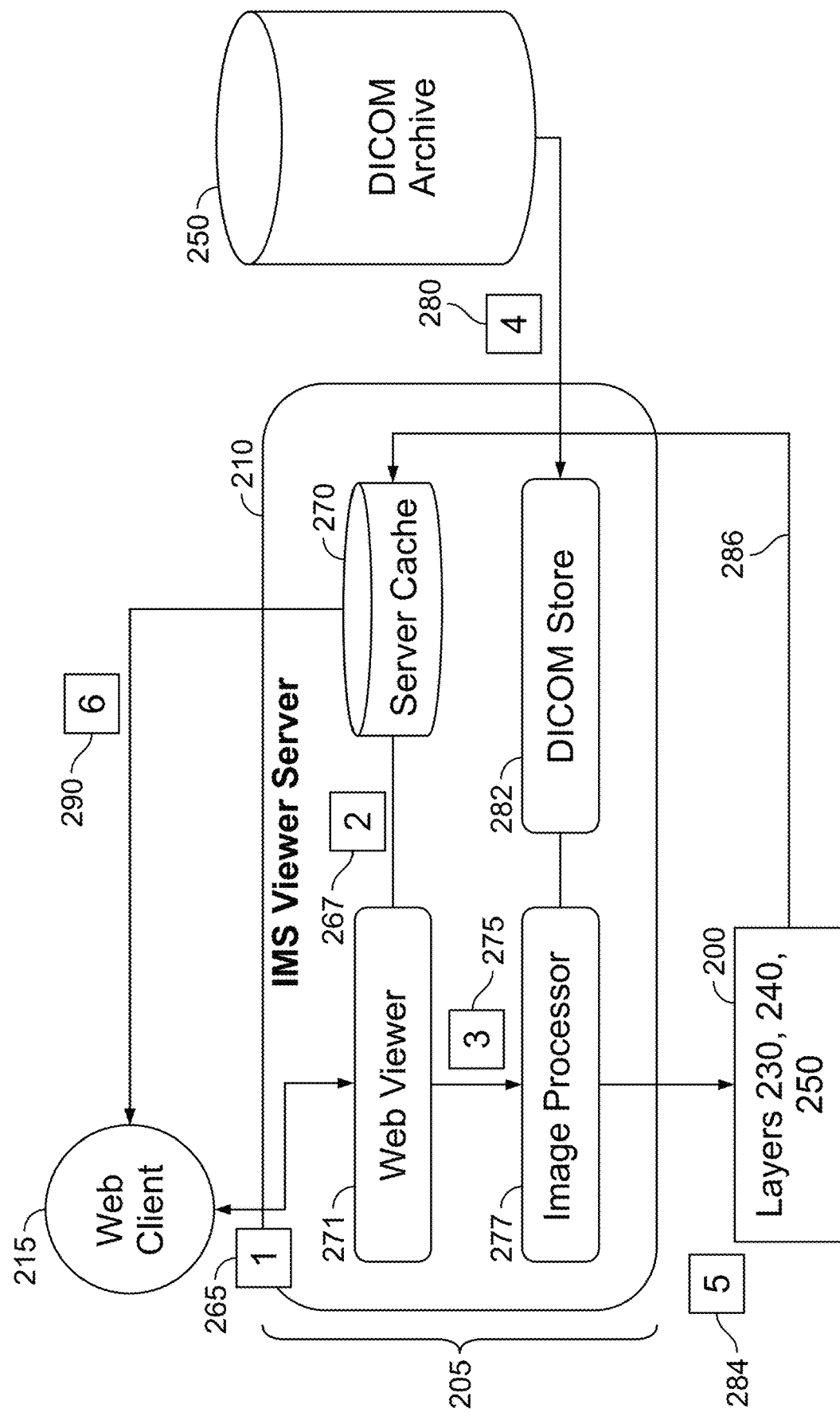
FIG. 2B is a block diagram illustration of a workflow in the front-end first layer with reference to the rest of the layers of the serverless cloud computing system of FIG. 2A, in accordance with some embodiments of the present specification.

In various embodiments, upon receiving a request for a study from a device 106, using serverless technologies, the service 115 performs the following actions:

a) validates if the requesting user at the device 106 has a permission to access the study requested;

b) writes in an access log that the user at the device 106 is accessing the study. The access log itself can be implemented using serverless technologies, in some embodiments, for instance:

i) Using serverless databases such as DynamoDB in AWS or Firebase in GCP ii) Using log services from the cloud provider such as CloudWatch in AWS or Stackdriver Logging in GCP c) obtain the study requested by the device 106 from the cloud archive 114 using DicomWeb protocol;

d) post-process the images received, including:

i) Separating DICOM Tags from pixel data ii) Generating a thumbnail representation of the DICOM image iii) Generating a JPEG representation of the DICOM image iv) Compressing the DICOM pixel data e) store the information generate in step d in a location which can be accessed by a client-side viewing application (such as in the Web Cache 270 of FIG. 2B).

f) provide to the client-side viewing application the credential to access the data stored.

In embodiments, the service 117 performs similar steps however at step (c) instead of using DicomWeb will access the data on the file storage 116, for instance using the identifier of the study requested. Both services 115 and 117 check the presence of the study in Web Cache prior to processing the image data from the archives. They also monitor usage of the Web Cache, for instance evicting studies which have not been used for a while. It should be appreciated that the services 115, 117 can be implemented in a number of serverless technologies, for instance using Lambda Function in AWS and Cloud Function in GCP.

Thus, in some embodiments, services 115 and 117 are implemented within cloud platforms 110 and 112, respectively, as serverless technologies. Alternatively, services 115 and 117 are implemented on separate and discrete servers, such as on at least one server 125, that access the cloud services on platforms 110 and 112, via DICOMWeb and APIs. If implemented as a serverless technology, the programmatic instructions comprising services 115, 117 are organized as a series of discrete function calls that, when a request is received from a user device 106, a function call is configured to determine the nature of the received request and to call upon, or instantiate, a plurality of programmatic instructions, organized as modules or functions, from the cloud platforms 110, 112 based upon the nature of the received request. This stands in contrast with a separate and discrete server, such as the at least one server 125, which is configured to execute an application to address the received request and not distribute that computational process to the cloud platform.

Serverless Cloud Computing

FIG. 2A is a block diagram illustration of a serverless cloud computing environment or system 200 operating as a FaaS (function-as-a-service) platform to provide image storage, access and processing services, in accordance with some embodiments of the present specification. In embodiments, the serverless cloud computing system 200 is configured to activate, implement or execute a plurality of instructions or programmatic code in units of functions in response to at least one event such as, for example, a user's command/request.

In some embodiments, the system 200 comprises a front-end first layer 205, a task scheduling second layer 230, an execution third layer 240, a back-end database or archiving fourth layer 250 and an infrastructure fifth layer 260.

The front-end first layer 205 comprises a web server 210 that, in some embodiments, may host a medical image archiving and viewing website 212 for access by at least one user computing device 214 running a client-side viewing application 215 and by a caching and syncing device 208 running a caching and syncing application 209. It should be appreciated that while in some embodiments the web server 210 is implemented within the cloud computing environment 200 (as the first layer 205), in alternate embodiments, the web server 210 is implemented on at least one separate and discrete server (such as, the at least one server 125 of FIG. 1) that interfaces with the cloud computing environment 200.

In some embodiments, the client-side viewing application 215 generates and provides at least one GUI to enable a user to transfer medical images for storage/archiving and access medical images stored/archived in the back-end database or archiving fourth layer 250 for rendering in the at least one GUI. Similarly, the caching and syncing application 209 enables transmission of medical images for storage/archiving and accessing medical images stored/archived in the back-end database or archiving fourth layer 250.

In embodiments, medical images are either processed in the execution third layer 240 before being transferred to the at least one user computing device 214 and/or are processed in the at least one user computing device 214 before being rendered in the at least one GUI generated by the client-side viewing application 215. It should be appreciated that the medical images, that may be retrieved and rendered for display using a client-side viewing application 215 on the at least one user computing device 214, may be associated with at least one 'series' wherein a plurality of series may be part of a 'study' related to a patient.

In embodiments, the at least one user computing device 214 and the caching and syncing device 208 are in data communication with the web server 210 through a wired and/or wireless network 220 that may be private or public such as the Internet. User request (generated from the at least one computing device 214 and/or from the caching and syncing device 208), for storing, accessing and executing at least one function for processing medical images, is received at the web server 210.

In some embodiments, the task scheduling second layer 230 comprises a controller 232 and a load balancer 234. The web server 210 communicates the user request, such as, for example, for executing at least one function, to the controller 232 and receives a result, such as, for example, of execution of the at least one function, from the controller 232 for communicating to the at least one computing device 214 and/or to the caching and syncing device 208. The user request is communicated by the controller 232 to the load balancer 234 that allocates a job or task associated with the user request to an execution environment 242 in the third layer 240.

The third layer 240 comprises a plurality of execution environments $242_1$-$242_n$ that are stateless virtual computing instances or virtual compute units such as, for example, virtual machines or containers in which functions (associated with user requests) are executed or run. A function may be launched in an execution environment that is already running or, if no compatible execution environment is running, an execution environment may be launched to run the function. In embodiments, the execution environment 242 may access a plurality of instructions or programmatic code and/or data associated with the function (allocated by the load balancer 234) from the at least one database system 250. The execution environment 242 may execute the accessed code and/or use the accessed data (from the least one database system 250) to perform the function corresponding to the user request.

Persons of ordinary skill in the art would appreciate that the load balancer 234, in some embodiments, is a software program responsible for the distribution of tasks, jobs or workloads, corresponding to user requests, across the plurality of existing and/or newly launched execution environments $242_1$-$242_n$ that in turn are virtual computing instances of a plurality of hardware resources in the infrastructure fifth layer 260.

In embodiments, the infrastructure fifth layer 260 comprises hardware resources such as, but not limited to, a plurality of computing resources (such as, for example, one or more host servers), a plurality of storage resources (such as, for example, one or more storage array systems, such as SAN), and a plurality of networking resources. The hardware resources are configured to enable functionalities corresponding to the layers 205, 230, 240 and 250. In various embodiments, the plurality of computing resources may be constructed on server grade hardware platforms that each include conventional components of a computing device, such as one or more processors, system memory, a network interface, storage system, and other Input/Output devices such as, for example, a mouse and keyboard. In some embodiments, the hardware resources of the fifth layer 260 may be distributed across multiple data centers in various geographical locations.

FIG. 2B is a block diagram illustration of a workflow in the front-end first layer 205 with reference to the rest of the layers of the serverless cloud computing system 200, in accordance with some embodiments of the present specification. Referring to FIGS. 2A and 2B, the web server 210 receives a user request at step 265, from a client-side viewing application 215 (and/or from the caching and syncing application 209), which triggers a process, function or operation to load medical information such as a medical image, series or study. At step 267, the web server 210 first checks to see if the medical information requested is already loaded in the web server cache 270 and if the information is the same as the one in the storage 250 (that is, the web server 210 verifies that the data cached is consistent with the content of the storage 250). If not, then the web server 210 generates a request to process the medical information.

At step 275, the generated request to process the medical information is received by an image processor 277 for subsequent processing (if it is not already processing). At step 280, the image processor 277 causes files, related to the medical information, to be moved from the storage 250 to a DICOM store process 282 running on the web server 210.

As image information files are received in the DICOM store process 282 the image processor 277 ingests the files, processes them (for example, to re-orient or generate thumbnails) and transfers them to the layers 230, 240 and 250 of the serverless computing system 200 for further processing, at step 284. At step 286, medical information files after having been processed at layers 230, 240 and 250 are transferred to the server cache 270. Finally, at step 290, the files from the server cache 270 are communicated back to the client-side viewing application 215 for viewing and/or to the caching and syncing application 209, although it should be appreciated that, preferably the caching and syncing application only uses original DICOM files and not the modified content. Server 210 supports the client-side viewing application 215 using the web viewer module 271.

In accordance with various aspects of the present specification, leveraging of the serverless cloud computing system 200 for image storage, access and processing of medical images reduces costs and increases scalability. For example, a serverless computing service, such as AWS® Lambda, can execute code in response to events in a massively parallel way, while at the same time reducing liability since patient health information (PHI) such as, but not limited to, the medical images is stored in the system 200 that may be managed by a third party FaaS operator/provider separate from the entity engaged in acquiring, storing, processing and accessing medical images.

In various embodiments, the entity effectively breaks-down its processing functions into units and has each unit executed in execution environments instantiated on the system 200. Cost reduction is achieved since the entity is required to pay only for the resources, on the system 200, that are actually used and not for idle servers. Also, the entity is freed up from patching and managing servers. Applications or functions dealing with personal data and healthcare data such as, for example, the medical images need to comply with the Health Insurance Portability and Accountability Act (HIPAA) that increases the costs for the entity to maintain its own servers. With the use of FaaS provisioned on the serverless cloud computing system 200, the entity is no longer required to store medical images on its own servers thereby reducing the HIPAA requirement liabilities by leveraging the HIPAA compliance of a third party operator/provider of the system 100.

Thus, serverless computing or FaaS enables computing of applications, methods or functions in short-lived, stateless execution environments $242_1$-$242_n$ with highly flexible scaling and typically a pay-for-what-you-use price structure. In contrast to physical servers, the entity using serverless computing services no longer needs to provision and manage physical servers, and can instead build applications as a set of functions that run in the serverless computing environment. Resource provisioning and scaling are then handled by a third-party cloud provider of the serverless computing environment. A description of the specific functions deployed in the serverless computing environment is provided below under Medical Imaging Processing Functions.

Caching and Syncing Application

Referring back to FIG. 1, the one or more computing devices 102 and medical imaging devices 104 communicate with the at least one server 125 and the cloud platforms 110, 112 through the caching and syncing device 108 that implements the caching and syncing application 109. It should be evident to persons of ordinary skill in the art that the caching, syncing and other functionalities of the device 108, being discussed below, are enabled by the caching and syncing application 109. As discussed earlier in the specification, that while FIG. 1 illustrates the at least one server 125 as a separate and discrete server in data communication with the one or more cloud platforms 110 and 112, in alternate embodiments the at least one server 125 may be implemented within the one or more cloud platforms 110 and 112.

In some embodiments, the caching and syncing device 108 is a DICOM device which implements part of the DICOM standard relative to image communication. In embodiments, the caching and syncing device 108 uploads and stores DICOM files in one or more cloud platforms 110 and 112. Moreover, data from DICOM archive 114 and file storage 116 is federated by caching and syncing application 109 implanted at caching and syncing device 108. The caching and syncing device 108 also provides a DICOM protocol to its clients. Further, the caching and syncing application 109 performs a pre-fetch function in order to make certain images readily available to users on demand. The pre-fetch function is described in U.S. Pat. No. 9,659,030 and is incorporated herein by reference.

The caching and syncing application 109 is configured to automatically download images added to cloud storages 114 and 116 by other devices. The caching and syncing application 109 is also configured to automatically download older images of a patient for whom recent images were added to cloud storages 114 and 116 by other devices and prior images of the patient which have been received from local devices or imaging modalities. The older images are generally termed as 'priors'. In embodiments, the caching and syncing device 108 operates on the Least Recently Used (LRU) principle, so as to optimize usage of the limited amount of storage available therein. Accordingly, the least recently used images or data is discarded first to free up storage space in the caching and syncing device 108.

The caching and syncing device 108 communicates with the DICOM archive 114 using the DICOM protocol. In some embodiments, a web extension of the DICOM protocol, known as DICOMWeb, is used to enable communication between the caching and syncing device 108 and the DICOM archive 114. DICOM archive 114 in cloud platform 110 services the caching and syncing device 108 by indexing the images that are uploaded to archive 114, thereby enabling the caching and syncing device 108 to query all the medical data pertaining a patient, or data within a specific time period, or data sorted by any other parameter that may be indexed. For example, DICOM archive 114 keeps in a database a list of images, for each image, an identifier linking the image with a specific patient and the date when each image was acquired. Therefore, when the caching and syncing device 108 requires the list of images for a patient, DICOM archive 114 is able to provide that list quickly, by querying the database.

In some exemplary embodiments, data is indexed by patient name, patient ID, patient birth date, accession number (to identify the physician request), modality, the portion of the patient's anatomy that was studied, and study date. In this example, the caching and syncing device 108 may query for all the medical images of a patient corresponding to a name, ID, and date. In addition, DICOM archive 114 services the caching and syncing device 108 by converting formats of images and representing them in the format requested by the caching and syncing device 108.

In some embodiments, the caching and syncing application 109 speeds up image delivery to devices 102 by maintaining a list of the series or studies it has in cache and determines what is available in external cloud platforms 110, 112. The caching and syncing application 109 then can broadcast what is available (a unified list) to workstations on the LAN 120. In some embodiments, the client-side viewing applications installed on devices 106 also enable speeding up image delivery, at devices 106, by maintaining a list of the series or studies it has in cache and determining what is available in external cloud platforms 110, 112.

In some embodiments, the caching and syncing application 109 is configured to keep a) the most recent images (oldest images are removed) and b) images (even if old) associated with a patient who has recent images. With respect to (b), the caching and syncing application 109 is configured to automatically search for "priors", namely studies, series, or other images that correspond to the same patient but were taken at an earlier date or pursuant to a different physician prescription, the moment it detects a patient name from one or more tags of a DICOM image.

In other embodiments, the client-side viewing applications is also configured to keep a) the most recent images (oldest images are removed) and b) images (even if old) associated with a patient who has recent images. With respect to (b), the client side viewing application is configured to automatically search for "priors", namely studies, series, or other images that correspond to the same patient but were taken at an earlier date or pursuant to a different physician prescription, the moment it detects a patient name from one or more tags of a DICOM image.

In some embodiments, the system 100 also includes a control module that may be used to program a plurality of business rules to be followed by the caching and syncing application 109 and the client-side viewing applications. In some embodiments, the business rules can define the basis for pre-fetching data (such as getting "priors", keeping the most recent, getting an old scan with a new annotation) and basically anything that could warrant propagating data to their cache. In some embodiments, a plurality of instructions or programmatic code associated with the control module are stored and executed in the cloud platforms 110, 112 and/or in the caching and syncing application 109 and the client-side viewing applications.

In some embodiments, as discussed above, server 125 and services such as services 115 and 117 are implemented within and by the caching and syncing device 108 to enable sending and receiving images to and from DICOM devices and to upload these images to or download images from the archive 114. In an example, an image requested by the caching and syncing device 108 may be requested with a different compression or even a JPEG representation of the image, rather than as a conventional, uncompressed DICOM file. Such a conversion is provided by the cloud platform 110 for the data in DICOM archive 114 and communicated to the caching and syncing device 108.

The caching and syncing device 108 communicates, through the at least one server 125, with file storage 116 within cloud platform 112 using an API provided by the specific cloud platform 112. In an example, cloud platform 110 provided by AWS provides an API for accessing their Simple Storage Service known as S3. Using S3, the caching and syncing device 108 may delete in, upload to, and download files from, storage 116 of AWS. In embodiments of the given example, the caching and syncing device 108 may request for either immediate access through S3 standard storage class to access long-lived but less frequently accessed data, or for gradual access through S3 Glacier for long-term archives. In embodiments, a date stamp of the images is used to determine the type of access provided to the images. Images that were acquired long ago, may be archived in a low-cost high latency storage, such as S3 Glacier. It is assumed that these images will likely not be needed, and if they are it will be on exception based. Therefore, recent images instead are cached on the standard S3 storage which provides immediate access. Data may be retrieved from S3 Glacier using pre-fetch and without having the user waiting for it. In case of retrieval of older images, the user may be indicated that the data is 'offline' and so some time should be expected for the images to be available.

In some embodiments, cloud platform 112 may provide online and offline storage for images, for immediate and gradual access, respectively. In some embodiments, the caching and syncing device 108 is configured to store a portion of files in an online storage and another portion in an offline storage, so as to distribute the costs of storage that may be offered by the servicing cloud platform 112. In some embodiments, the date stamp of the images is used to determine which files are stored online or offline. In some embodiments, the older files are stored in the offline storage, and recent files that are more likely to be accessed are stored in the online storage. In some embodiments, the caching and syncing device 108 migrates images and files from one type of storage to another type of storage, in order to manage costs. In some embodiments, cloud platform 112 is able to migrate the images and files automatically.

In order to store DICOM images in file storage 116 and provide a DICOM communication protocol to its clients, the caching and syncing device 108 is configured to index images stored in file storage 116. For each image that is stored, the caching and syncing device 108 associates the image with relevant information that may be used to locate/retrieve the image. Examples of the types of associations made may include patient name, patient identity, modality, or any other types of tags that enable retrieving the relevant image. Further, the caching and syncing device 108 is configured to associate each image with the location of the image in storage 116, and the storage class where applicable. Once the caching and syncing device 108 receives a request to provide a particular set of images, it may identify the indices for each image in the set of images, based on the associated data provided with the request. The indices are used to locate the files in storage 116. The caching and syncing device 108 may also convert the images to a suitable format or representation, as may be stated in the received request, and send the requested set of images using DICOM protocol to the requesting client device. Methods and systems for converting formats of image representations are discussed in greater detail in U.S. Pat. No. 9,298,730, incorporated herein by reference.

In embodiments, the caching and syncing device 108 is configured as a node on the LAN 120 which may be a network of an institution, such as a medical institution, supporting an HIS (Hospital Information System) or an RIS (Radiology Information System). In some embodiments, the caching and syncing device 108 may be a server or any other type of computing system with a guided user interface. In embodiments, a third party license may be used to provide and configure the caching and syncing application 109 on the caching and syncing device 108 within the network 120. The caching and syncing device 108 is connected to multiple devices and facilitates communication with cloud platforms such as 110 and 112.

The caching and syncing device 108 also provides backward compatibility to legacy applications on devices 102. For example, in one embodiment, the caching and syncing device 108 provides backward compatibility to the legacy application eFilm. The caching and syncing device 108 is controlled by an administrator through the cloud. An administrator may effect multiple changes in the setting, configuration, and operation of the caching and syncing device 108. The administrator may be a technical person of the institution in which the caching and syncing device 108 is deployed. The administrator's functions may include, but are not limited to, a) granting the caching and syncing device 108 access to archive storage 114 or 116, b) monitoring disk space used by the caching and syncing device 108 and modify it accordingly, c) configuring pre-fetch settings, d) monitoring usage and performance statistics (for instance cache bits and cache misses), e) listing DICOM devices to allow for the querying and requesting of data, and f) configuring a mode of uploading data received in the stores 114 and 116. In some embodiments, the administrator uses one of the user computing devices 106 that is configured to use services 115 or 117 to administrate the caching and syncing device 108. In embodiments, the administrator administrates multiple caching and syncing device 108 installations, each of which are monitored through a dashboard or any other type of interface through the administrator's device 106.

In some exemplary embodiments, the administrator may configure the caching and syncing device 108 with a name or an identifier, an Application Entity (AE) title, a port, a DICOM store, whether pre-fetch functionality shall be available, amount of disk-space to be used, among other parameters. Any DICOM service is a transaction between two applications: an SCU (Service Class User) that initiates the request and an SCP (Service Class Provider) that responds. Each application is identified by the IP address of its host, the TCP port number used for the connection, and a DICOM AE title that is a string that names the application. In some embodiments, the caching and syncing device 108 enables configuring multiple AE titles, where each title connects it to a different end point (DICOM Store).

In one exemplary scenario, the imaging devices 104 acquire a set of images and transmit them to the at least one image storage system 122 from where the set of images may be immediately cached in the caching and syncing device 108 by the caching and syncing application 109. In other words, the caching and syncing application 109 keeps the set of images in cache as well as in the at least one image storage system 122. Alternatively, in some embodiments, the imaging devices 104 acquire a set of images and upload them directly to the caching and syncing device 108 from where the set of images may be immediately synced and stored in the at least one image storage system 122. Thus, the set of images are available at the caching and syncing device 108, and are therefore readily available to a user who wishes to access the set of images through a device 102 that may be a legacy system, provided the device 102 is communicating with the caching and syncing device 108 within the same network 120.

The caching and syncing application 109 also ensures that data in its local memory/cache, the at least one image storage system 122 and the one or more cloud platforms 110, 112 remain in-sync. Thus, in embodiments, the caching and syncing device 108 uploads the set of images to one or more cloud platforms 110 and 112 in real-time or at a later time. The location of cloud platforms 110 and 112 to upload the images may be configured by the administrator. In various embodiments, the time for upload is implemented in several ways, and is based on the institutional settings. According to one method, the caching and syncing device 108 uploads or syncs the images to cloud platforms 110 and 112 in real time to ensure that the data is backed up properly. The caching and syncing application 109 initiates a sync in real-time when it automatically and instantaneously initiates a transmission of the data to be synchronized upon an occurrence of one of a plurality of predefined triggers. In some embodiments, the predefined triggers comprise at least one of a) the application 109 determining that sufficient computing resources (such as bandwidth, memory, or processing power) are available, b) the application 109 determining that data to be synced has been in local memory, without being synced, for a predefined amount of time (exceeding a threshold), c) the application 109 determining that an amount of data exceeding a threshold amount is in local memory, without being synced, and d) the application 109 determining that data associated with a priority level (example, for an urgent case and based on a DICOM tag) exceeding a threshold amount is in local memory, without being synced.

In another method, the caching and syncing application 109 uploads images when it is idle. In this case, it is not known when the data will be fully uploaded, however users' request are fulfilled as fast as possible. In another method, the caching and syncing application 109 uploads the data at a specified time of the day or the week.

Further, in some embodiments, in order for device 102 to request images from the caching and syncing device 108, the caching and syncing application 109 is configured to retrieve the images from its local cache, an image storage system 122 or the one or more cloud platforms 110, 112 and send the images to the device 102. The caching and syncing device 108 may be configured to send requested images to device 102 by the administrator using the dashboard on device 106. As an example, a physician may want to edit tags associated with one or more images of a series that have been accessed from the caching and syncing device 108 by the physician using a computing device 102. In one embodiment, changes in the metadata, such as tags, of one or more images of the series (using the client-side viewing application of the computing device 102) are communicated by the caching and syncing application 109 to the cloud platforms 110 and/or 112 that may be in data communication with the caching and syncing device 108. The caching and syncing application 109 may also apply these changes to meta data stored to the at least one image storage system 122. In another example, the physician may want to manipulate at least one of the retrieved original images such as, for example, by making an annotation or mark up on an image, panning, zooming, adjusting the contrast, annotating, or any other type of image manipulation. In some embodiments, the caching and syncing application 109 creates a new DICOM file or artifact comprising the manipulated image while ensuring that the retrieved original image file is not changed. The caching and syncing application 109 transmits the new DICOM file to the cloud platforms 110 and/or 112 for storage in archives 114 and/or 116. There is no specific trigger to create the new DICOM file or artifact at the caching and syncing application 109 as this happens instantly and automatically as a consequence of manipulation of the original image. The caching and syncing application 109 may also transmit the new DICOM file to update the at least one image storage system 122.

In another exemplary scenario, the files uploaded through the caching and syncing application 109 to cloud platforms 110 and/or 112 are available to multiple users through multiple devices 102 and devices 106. These users on devices 102 and 106 may simultaneously access the images and collaborate if required.

In yet another exemplary scenario, a user computing device 106 may use its client-side viewing application to access and retrieve images from cloud platforms 110 and/or 112 and thereafter enable manipulation of at least one of the retrieved images and/or meta data (such as, for example, tags) associated with the images. For example, a physician may want to edit tags associated with one or more images of a series that have been accessed from cloud platforms 110 and/or 112 by the physician using a user computing device 106. In one embodiment, changes in the metadata, such as tags, of one or more images of the series (using the client-side viewing application of the user computing device 106) are communicated by the client-side viewing application to the cloud platforms 110 and/or 112 that in turn propagate the changes to every caching and syncing device 108 (that is associated with the study or series within which the image tags changed) in data communication with the cloud platforms 110 and/or 112.

In another example, the physician may want to manipulate at least one of the retrieved original images such as, for example, by making an annotation or mark up on an image, panning, zooming, adjusting the contrast, annotating, or any other type of image manipulation. In some embodiments, the caching and syncing application 109 creates a new DICOM file or artifact comprising the manipulated image while ensuring that the retrieved original image file is not changed. The caching and syncing application 109 transmits the new DICOM file to the cloud platforms 110 and/or 112 for storage in archives 114 and/or 116. Alternatively, the at least one server 125 creates the new DICOM file or artifact, for storage in cloud platforms 110 and/or 112, while ensuring that the retrieved original image file is not changed.

In one embodiment, there is no specific trigger to create the new DICOM file or artifact at the caching and syncing application 109 as this happens instantly and automatically as a consequence of manipulating the retrieved original image. In another embodiment, the new DICOM file or artifact is created at the caching and syncing application 109 only when a user attempts to store the state of the image.

In some embodiments, the cloud platforms 110 and/or 112 then notify every caching and syncing device 108 (that is associated with the study or series related to the image that was manipulated) in data communication with the cloud platforms 110 and/or 112 that a new image file has been added to the archives. In one embodiment, the archives 114 and/or 116 invoke a URL (of the new DICOM file) and broadcast it to every caching and syncing device 108 (push model). The caching and syncing devices 108 then invoke the broadcast URL, follow it to the where the new DICOM file is, and gets the new data.

In some embodiments, a caching and syncing application 109 of a caching and syncing device 108, in data communication with the cloud platforms 110 and/or 112, is configured to request or query (pull model) the cloud platforms 110 and/or 112 for changes to metadata associated with the images stored in the archives 114 and/or 116 and addition of one or more new images in the archives 114 and/or 116. In embodiments, the query may be performed on any periodic time basis. In case of changes, the caching and syncing application 109 downloads and applies these changes to meta data stored in its local cache/memory and to the at least one image storage system 122 thereby synchronizing the meta data across its local cache, image storage system 122 and the cloud platforms 110 and/or 112. Similarly, in case of new images, the caching and syncing application 109 downloads the new images to its local cache/memory and updates the at least one image storage system 122 thereby synchronizing the new images across its local cache, image storage system 122 and the cloud platforms 110 and/or 112. In embodiments, the caching and syncing application 109 queries the cloud platforms 110 and/or 112 on a predefined periodic time basis.

In embodiments, caching and syncing device 108 is configured as a DICOM node and communicates using DICOM protocol. It may receive as input all DICOM composite operations including and not limited to C-STORE, C-FIND, C-MOVE, C-ECHO. caching and syncing device 108 may use DICOM protocol to upload to and download images from cloud platforms 110. A single instance of caching and syncing device 108 may not be used to upload images to cloud platforms 110, therefore caching and syncing device 108 queries platforms 110 for each C-FIND operation. In some embodiments, caching and syncing device 108 supports end-points that are read-only. Cloud platform 110 maintains multiple DICOMWeb archives, each of which is an 'end point' for the caching and syncing device 108. The end point indicates the URL used by the application to communicate, and so to retrieve and store data. An example of a read-only end point is the NIH dataset. In its configuration to support read-only end points, caching and syncing device 108 may reject the C-STORE operation.

In some embodiments, the caching and syncing device 108 enables setting up of an end point for each AE title, wherein each AE Title defines a single end point. In a specific but not limiting example, the caching and syncing device 108 may define an AE title AE GOOGLE to point to a DICOMWeb storage 114, and an AE title AE AWS to point to storage 116. Device 102 when sending data to or requesting data from the caching and syncing device 108, indicates the AE title to execute the task of sending or retrieving. Devices 102, 104 trigger C-STORE each time they upload an image. The users at devices 102 and 104 may be enabled to upload received images to all mapped end points. The users at devices 102 and 104 may also be enabled to upload images to end points using a round-robin scheduling approach. The users may also be enabled to upload images to end points based on the AE title that is sending the images.

A patient may be associated with one or more medical examinations and procedures, collectively referred to as studies. Different patient studies may be commonly identified by patient metadata or an identifier, such as and not limited to the patient's ID. In embodiments, the caching and syncing device 108 provides a unified view of studies, using the common identifier, for each patient available on a cloud platform 110 and/or 112, and the studies that are available locally such as at its local cache/memory and/or at the at least one image storage system 122. That is, the caching and syncing application 109 at the device 108 generates, constructs or compiles studies associated with each patient. In some embodiments, an enterprise master patient index (MPI) is used to consolidate patient data for a single patient, where the data is archived across different databases. In some embodiments, locally available studies may include the studies that have been received by the caching and syncing device 108 and have not yet been uploaded by the caching and syncing device 108 on cloud platforms 110 and/or 112. This functionality enables the caching and syncing device 108 to also operate offline. During its offline operation, the caching and syncing device 108 may receive one or more images such as from devices 102 and 104, and may also have one or more images downloaded from it by devices 102 and 104.

DICOM files contain metadata, including tags, that provide information about the image data, such as the size, dimensions, bit depth, modality used to create the data, and equipment settings used to capture the image, among other information. In embodiments, the caching and syncing application 109 is configured to edit DICOM metadata and synchronize the edited metadata with the data on cloud platforms 110 and 112 through updates. The edits to metadata may entail correcting mistakes, filling blank information, or any other type of metadata-related edits. In embodiments, the DICOM protocol may not support edits to metadata. Therefore, the caching and syncing device 108 may communicate with DICOM archive 114 using API as well as DicomWeb protocols, so as to support editing of metadata. As a result, editing of metadata may be performed by means of a user interface generated by the caching and syncing application 109, which allows a user at one of devices 102, 104, 106 to perform the editing. Alternatively, the user interface generated by the caching and syncing application 109 may be used by the administrator of the caching and syncing device 108 through a device 102 or 106.

In embodiments, the caching and syncing device 108 is optimized to receive studies and upload them to archive 114 or storage 116 at the first instance without slowing the speed of receiving the studies. Optimizing the caching and syncing device 108 may involve the caching and syncing application 109 being configured to devote resources first in receiving/sending studies to devices 102 or 104 and afterwards, when no requests are received, to upload the data to cloud 114 and/or 116. This type of optimization can be implemented in a variety of ways, including threads priority and job queue.

In embodiments, the caching and syncing application 109 downloads studies from archive 114 and/or storage 116 when requested to move studies that are not local. Local studies may include the studies for which the caching and syncing device 108 has a copy. The local studies may have been downloaded by the caching and syncing device 108 from archives 114 and/or 116 sometime in the past or may have been received from devices 102 or 104 and later uploaded to archives 114 and or 116.

In embodiments, the LRU principle is used to manage and optimize the storage space available at the caching and syncing device 108.

In some embodiments, the caching and syncing application 109 is configured to anonymize received data. Anonymization enables maintaining relationship between studies and previous studies or priors, while removing patient information from the images. The relationship across the studies, maintained by anonymization, is important in cases where the anonymized data is used for clinical studies and/or subjected to neural network analyses. The relationship across the studies indicates the outcome of the treatment, and so is valuable. Here, priors include all the previous studies that were acquired on the same patient before. Priors allow physicians and patients to monitor the disease progression. Priors include common identifying information or patient metadata such as the patient's information, including patient name, patient ID, birth date, and other patient-specific information. Using this common information, the priors are automatically retrieved. In this embodiment, personal information associated with the received data is hashed. As long as the anonymization consistently hashes the patient's information in the same way, it will produce anonymized studies without losing the priors for that patient. Hashing involves transforming a string of characters comprising personal information into a shorter fixed-length value or key that represents the original string. In embodiments, the hash operation is configured to be implemented consistently over time such that hash for patient information received multiple times by a device is the same. In embodiments, the hash operation is configured to be implemented consistently over multiple instances, such that if the same patient is received by multiple devices connected to the same end point, it is hashed in the same manner. In embodiments, the hash operation is configured to be implemented consistently such that date in the study is modified consistently subtracting (or adding) a value which depends on the patient's hash. Therefore, a study acquisition date is also anonymized, specifically when it is clinically relevant to keep the same interval across the studies dates. In some embodiments, for purposes of security, the number of days to subtract (or add) varies among patients. In some embodiments, anonymization performed by the caching and syncing application 109 is identified by services provided by cloud platforms 110 and 112.

Figure 3A:
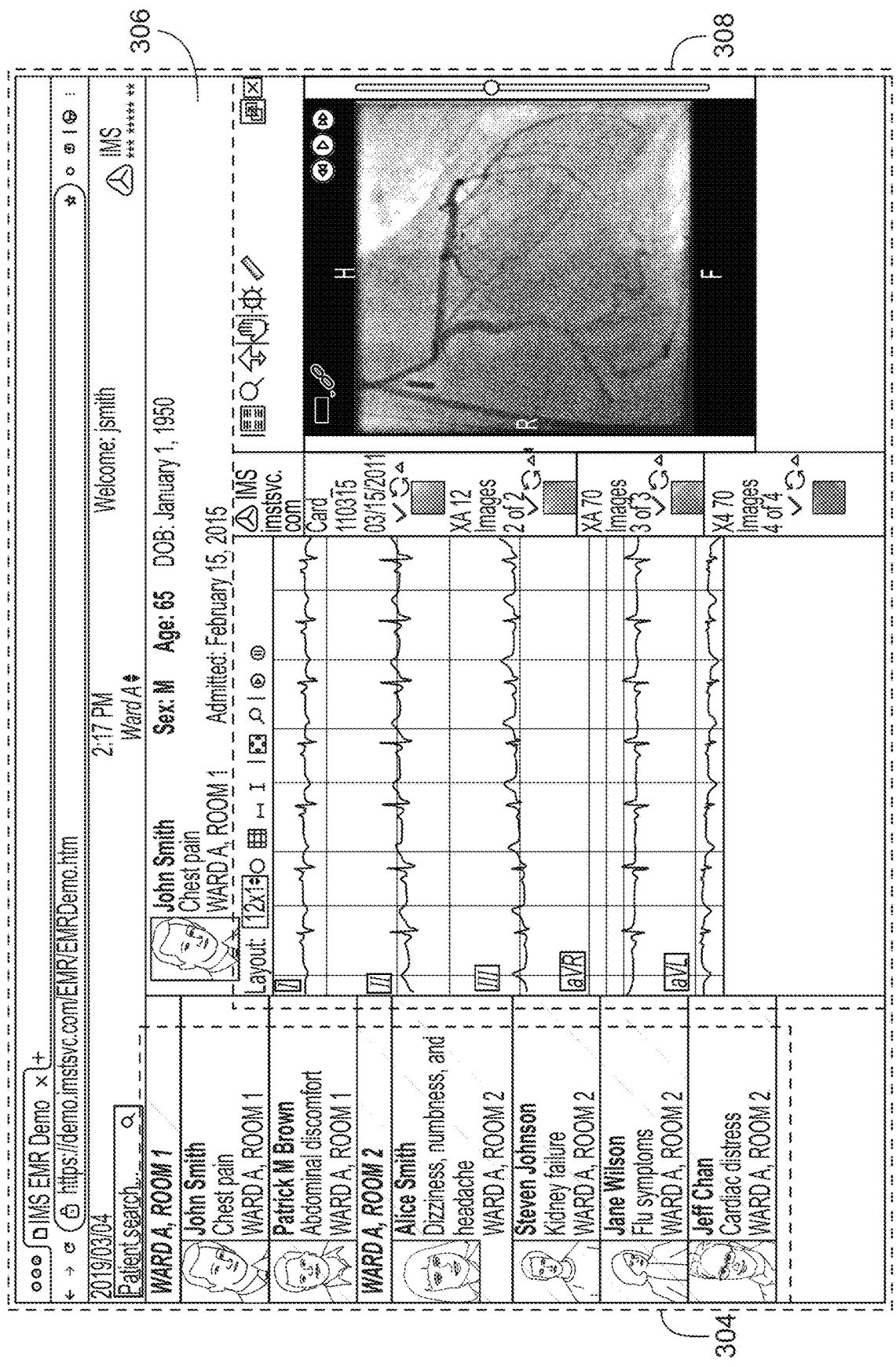
FIG. 3A illustrates an exemplary screenshot of a federated view built by built by a caching and syncing application, in accordance with some embodiments of the present specification.
Figure 3B:
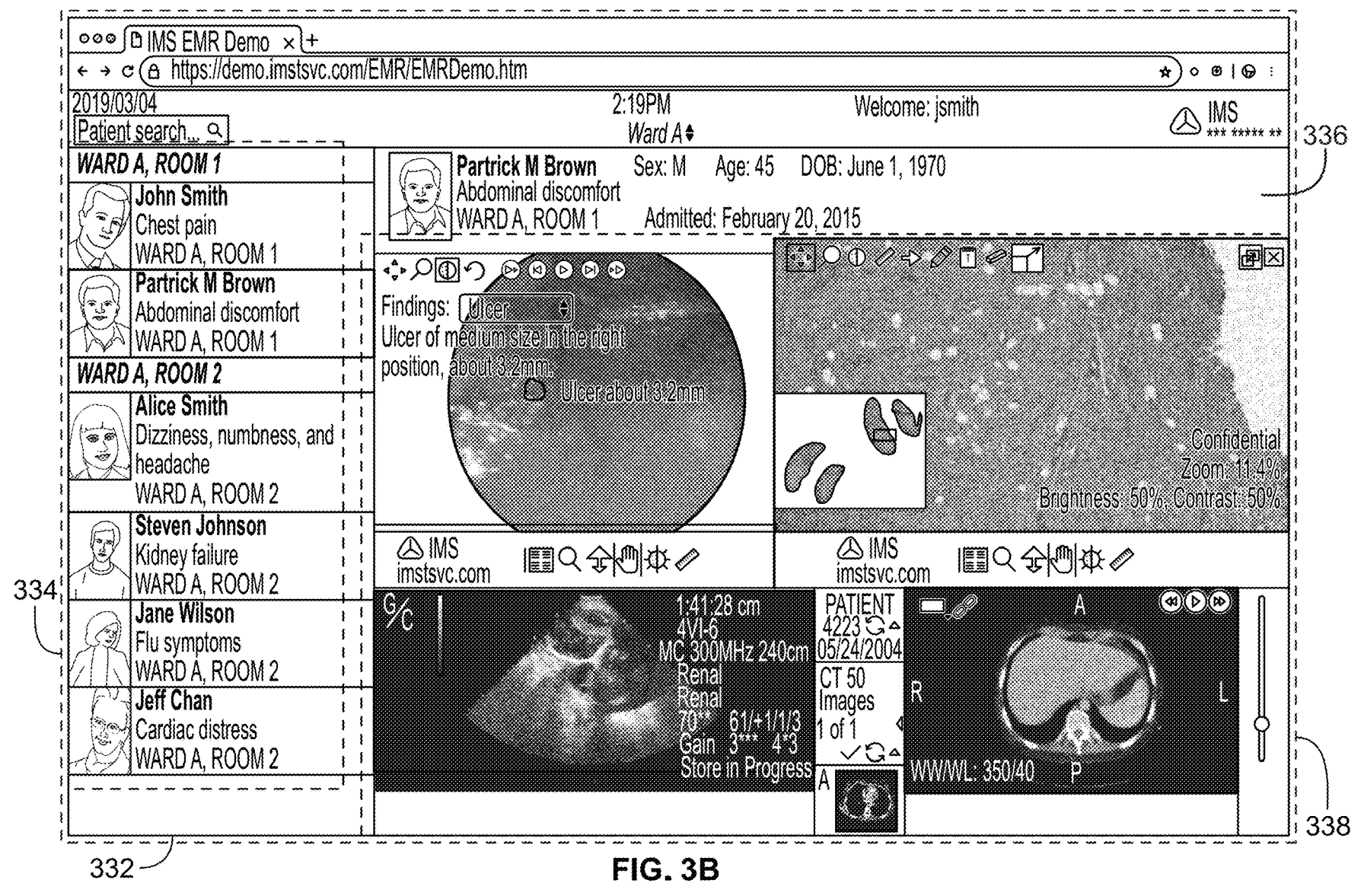

FIG. 3A illustrates an exemplary screenshot of a federated view that shows medical information stored in multiple cloud platforms 110 and 112, and the caching and syncing device 108, in combination, built by the caching and syncing application 109 in accordance with an embodiment of the present specification. FIG. 3B illustrates another exemplary screenshot of a federated view that shows medical information stored in multiple cloud platforms 110 and 112, and the caching and syncing device 108, in combination, built by the caching and syncing application 109 in accordance with one more embodiment of the present specification.

When the federation is done by the caching and syncing application 109, then device 102 might display federated DICOM data from multiple cloud platforms such as 110 and 112. In some embodiments, the federation is done by services 115 or 117 (that may be implemented within the at least one server 125 separate and discrete from or within the cloud platforms such as 110, 112), in which case devices 106 may display federated data from different repositories that include DICOM archives 114 and other file storages 116. In some embodiments, the federation of data is performed by device 102, which can then display data from DICOM archives 114 and other file storages 116, from multiple cloud providers. In some embodiments, services 115 and 117 that may be implemented within the at least one server 125 separate and discrete from or within the cloud platforms such as 110, 112) which connect to both archives 114 and file storages 116 are also connected to device 106, thereby enabling devices 106 to federate the data.

Referring simultaneously to FIGS. 3A and 3B, in some embodiments, the caching and syncing device 108 provides a unified view of studies for each patient available on a cloud platform 110 or 112, and the studies that are available locally. A display 302/332 is able to show images and related information to a user irrespective of where the data is stored. The user sees all the available data together, without any distinction as to the location of storage of the data. Display 302/332 show a list of patients in a menu 304/334 on the left side, and medical information corresponding to a patient selected from the list in menu 304/334 is shown on the right side. Menu 304/334 lists the patient according to demographics, and may include a picture of the patient as well. Medical information includes patient identity 306/336 and medical records 308/338 that could encompass DICOM images, ECGs, medical reports, or any other information such as machine learning or neural network-based analyses of the DICOM images.

Figure 10:
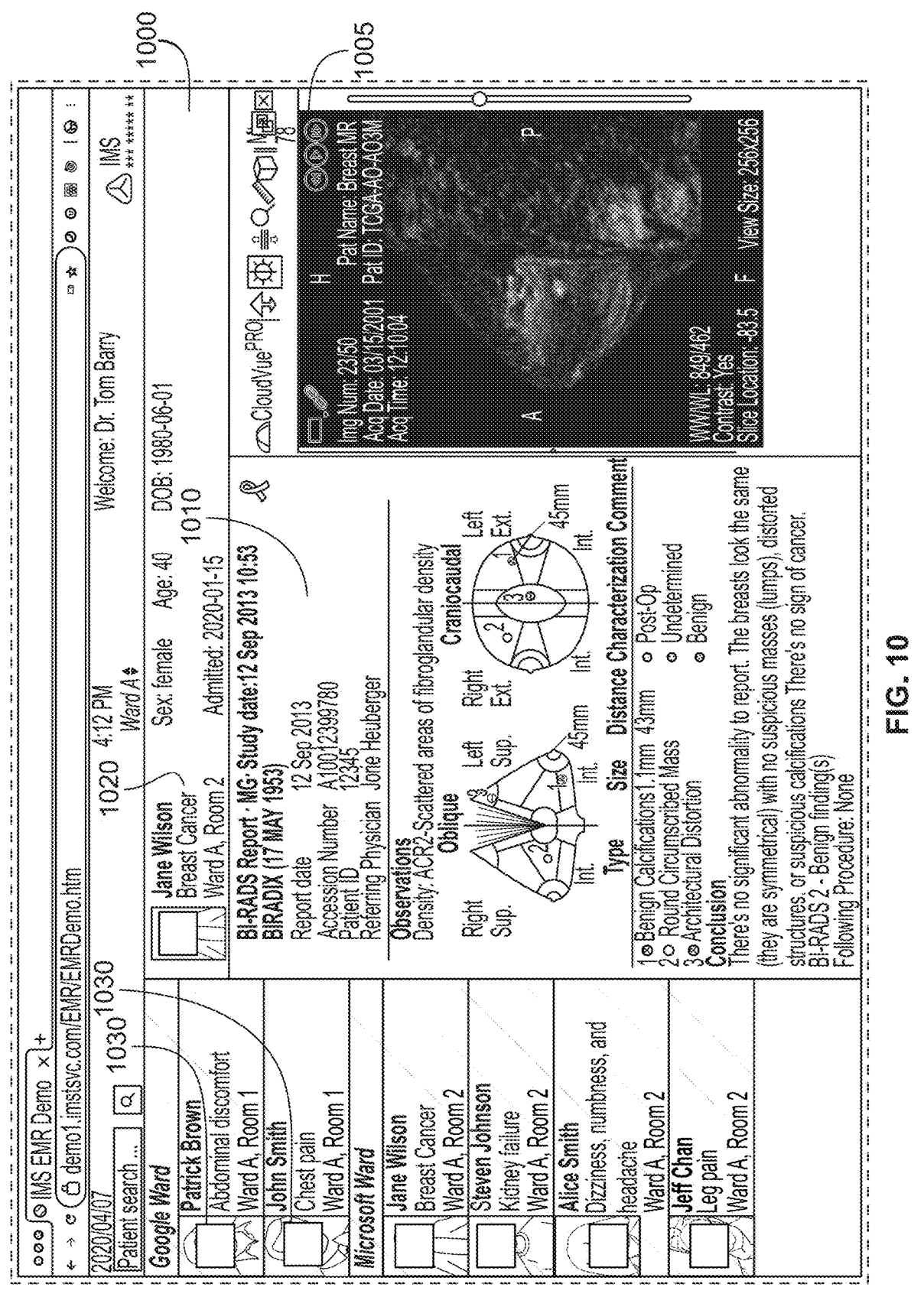

Referring to FIG. 10, neural network-based analyses of the DICOM images are presented in an exemplary graphical user interface (GUI) 1000. The interface 1000 comprises a GUI region for the DICOM image 1005, a GUI region for the neural network-based analysis applied to the DICOM image 1010, a GUI region for identifying the patient with a name, photo, location in the clinic or hospital, admission date to the clinic or hospital, gender, age, and/or date of birth 1020, and/or a GUI region listing all the patients available for the client-viewing application user to select 1030.

FIG. 3A illustrates an ECG and a DICOM image 308. FIG. 3B illustrates a DICOM image, an endoscopy, and a pathology slide 338. In some embodiments, the displays 302/332 are rendered within a client-side viewing application that runs on devices 102, 106. Alternatively, in some embodiments, the displays 302/332 are rendered within a legacy browser that runs on devices 102, 106. The legacy browser could be any type of browser, including and not limited to Internet Explorer, Mozilla, and Firefox.

In embodiments, the caching and syncing device 108 is configured as a DICOM node in order to manage, process, and transfer DICOM images. Other workstations, such as devices 102 and 104, in the facility can also see the federated view built by the caching and syncing device 108. While displays 302 and 332 are available to users at devices 102 and 104 where they can select a patient from menu 304/334 comprising a list of patients in their facility, users at devices 106 are able to see only their image data stored in multiple cloud platforms 110/112. In some embodiments, DICOM data from the cloud platforms 110 and 112 and locally acquired by the caching and syncing device 108 is federated to create the displays in exemplary illustrations of FIGS. 3A and 3B, at devices 102 and 104. In some embodiments, devices 106 are enabled to federate DICOM data from the cloud as well as non-DICOM data.

In various embodiments of the present specification, the client-side viewing application (installed on devices 102, 106) overcomes several limitations of the current applications, including those related to accuracy of data, and speed of compression and decompression. In an embodiment, the client-side viewing application of the present specification, including services 115 and 117, implement a compression scheme that is tuned for web application based on lossless JPEG (JPEG-LS) standard. JPEG-LS is based on a low-complexity algorithm, and is aimed at better compression of medical images. The present specification, in its embodiments, improves upon the JPEG-LS standard by splitting the images into separate data packages, or chunks, instead of being compressed as a single one.

Further, in embodiments, the methods and systems of the present specification provide several levels of data caching. Data is cached at the caching and syncing device 108 and is available for downloading by devices 102, 104 also when the caching and syncing device 108 is not communicating with cloud platforms 110 and 112. At another level, data is cached by a web server, also termed as Web Viewer Cache, and is described in detail in U.S. Pat. No. 9,659,030, titled "Web server for storing large files" and U.S. Pat. No. 9,298,730, titled "System and method for viewing medical images", and incorporated herein by reference in their entirety. The web viewer cache is managed by services 115 and 117. At another level, data is cached to the client-side viewing application or the legacy browser of the user at devices 106 ahead of time. At yet another level, data is cached also in the client-side viewing application, while the users at devices 106 look at other images.

Client-Side Viewing Application

A client-side viewing application is configured to access/retrieve medical images and render the medical images for display in one or more GUIs generated to enable a user to view and manipulate the digital images. In some embodiments, the client-side viewing application generates and provides at least one GUI to enable the user to transfer medical images for storage/archiving and access medical images stored/archived in one or more cloud platforms for rendering in the at least one GUI.

In some embodiments, the client-side viewing application running on devices 102, 106 is configured to display or render data corresponding to a 'patient jacket' that comprises a plurality of GUI tabs to render or display an integrated or federated view of a patient's medical information comprising studies, associated metadata, machine learning or neural network based analyses associated with one or more images in the studies and targeted advertising. In some embodiments, the 'patient jacket' is tailored or customized to the type of images in the studies or the type of user.

Figure 9:
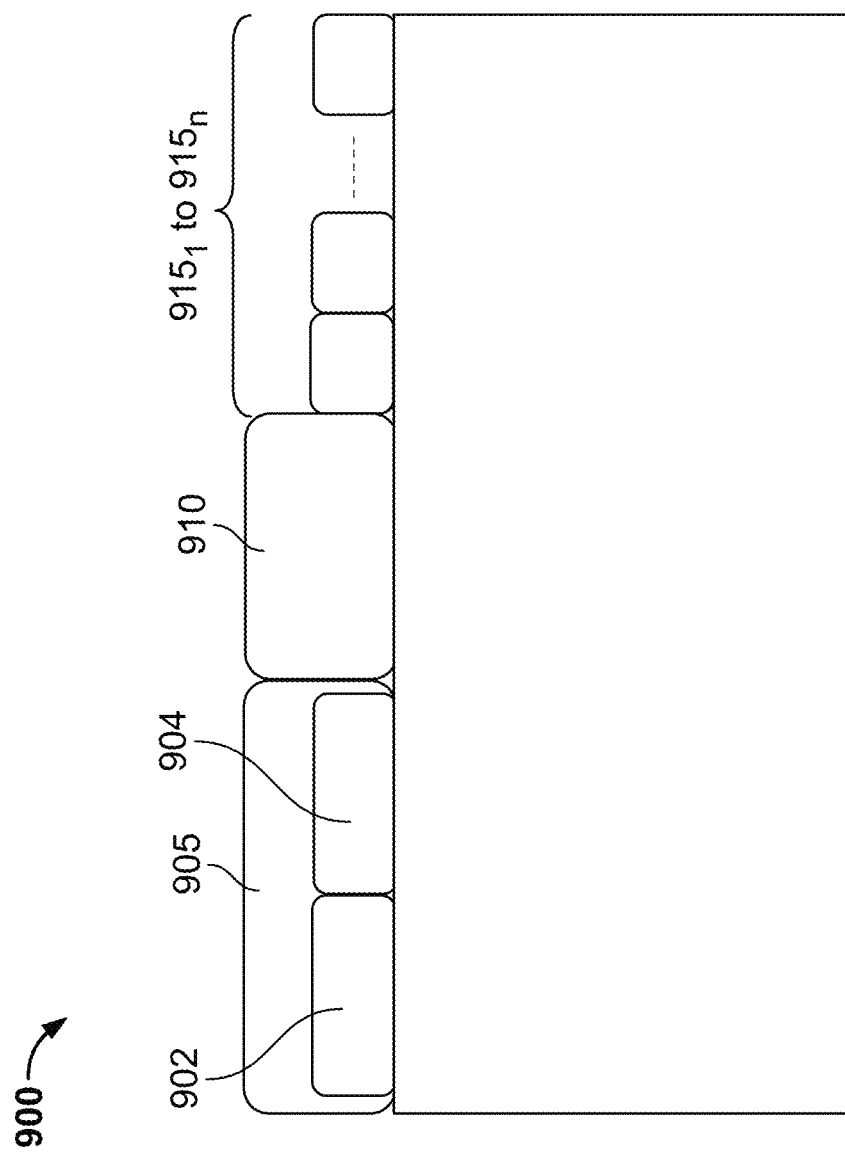
FIG. 9 illustrates a "patient jacket" GUI, in accordance with some embodiments of the present specification.

As a non-limiting example of tailoring or customization of the 'patient jacket', the client-side viewing application is configured to add, or remove, one or more tabs based on the kind of data available in a given study, in a given series, and/or associated with the metadata of the images. In one embodiment, where a study comprises more than one series, a tab dedicated to each series is generated and displayed within the client-side viewing application. Therefore, as shown in FIG. 9, where a study 905 comprises two series, the client-side viewing application 900 generates two separate tabs 902, 904 labeled with names of each of the two series. In another embodiment, where more than one study is associated with the patient, a tab dedicated to each study is generated and displayed within the client-side viewing application. Therefore, where the patient has two studies 905, 910 associated with him or herself, the client-side viewing application 900 generates two separate tabs 905, 910 labeled with names of each of the two studies. In another embodiment, where an image has multiple meta-data types associated therewith, such as an aggregated score, diagnosis, anatomy, or other data, a tab dedicated to each data type $915_1$ to $915_n$ is generated and displayed within the client-side viewing application 900.

In some embodiments, data corresponding to the 'patient jacket' is constructed, collated or compiled by the client-side viewing application reaching out to multiple cloud platforms 110, 112 as well as the caching and syncing device 108 and pulling down studies, associated metadata and machine learning based analyses corresponding to the patient metadata such as, for example, patient ID. In some embodiments, data corresponding to the 'patient jacket' is constructed, collated or compiled by the at least one server 125 (configured separate from or within the cloud platforms 110, 112) by accessing multiple cloud platforms 110, 112 as well as the caching and syncing device 108 and pulling down studies, associated metadata and machine learning based analyses corresponding to the patient metadata. The data corresponding to the 'patient' jacket', constructed or generated by the at least one server 125, is then available for download and rendering by the client-side viewing applications at devices 102, 106. In some embodiments, data corresponding to the 'patient jacket' is constructed, collated or compiled by the caching and syncing device 108 reaching out to multiple cloud platforms 110, 112 and pulling down studies, associated metadata and machine learning based analyses corresponding to the patient metadata. It should be appreciated that the DICOM standard does not have protocols, templates, or other format structures configured to generate the aforementioned patient jacket and that the client-viewing application would have to integrate a proprietary application to form such a patient jacket with DICOM data access.

In embodiments, the machine learning or neural network based analyses, associated with one or more images in the studies, are generated by executing one or more processing functions in one or more execution environments such as, for example, containers or virtual machines in the execution layer (such as the third layer 240 of the cloud computing system 200 of FIG. 2A) of one or more of the cloud platforms 110, 112.

Figure 14:
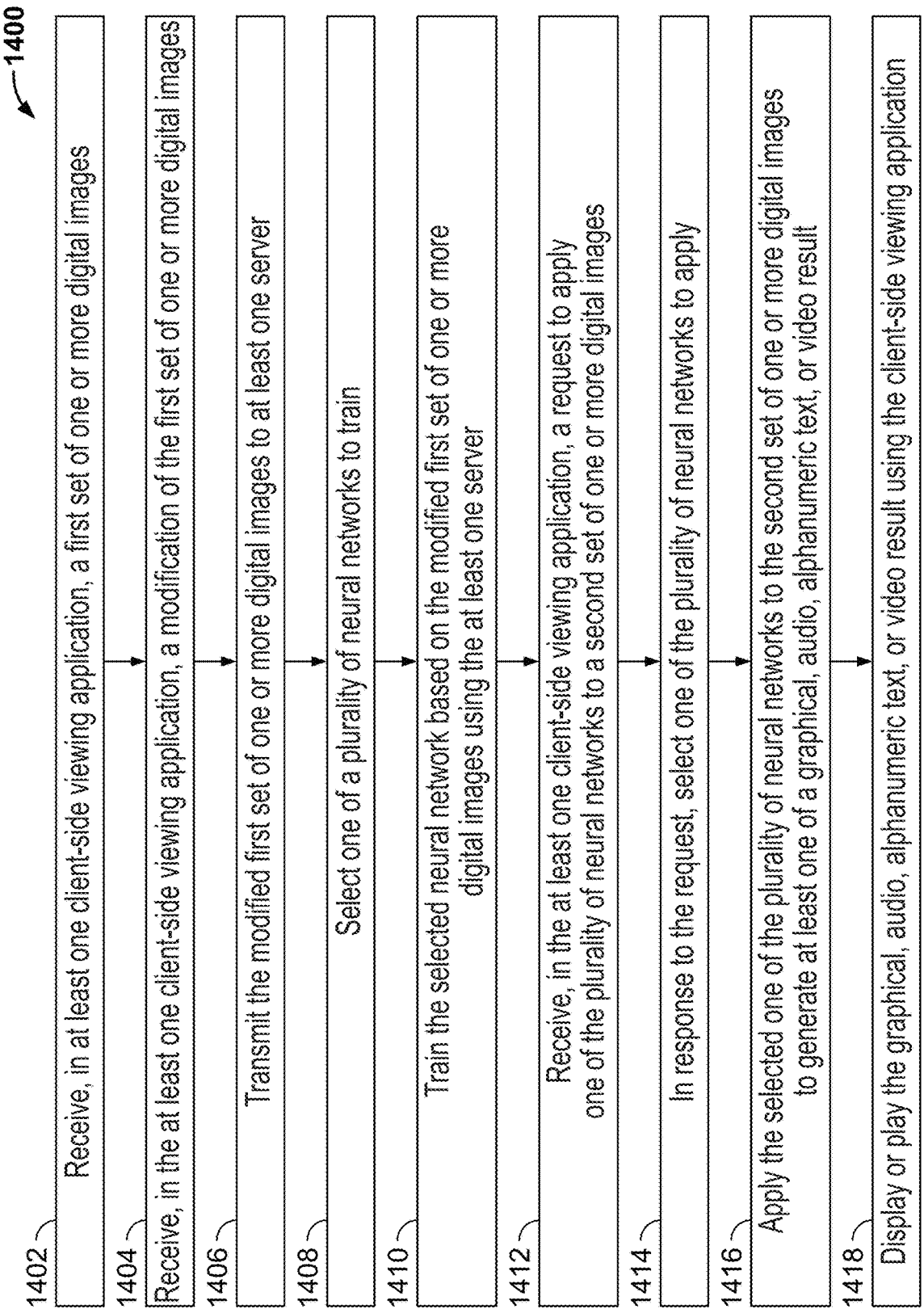
FIG. 14 is a flowchart of a plurality of exemplary steps of a method of training a plurality of neural networks and providing access to the trained plurality of neural networks for processing one or more digital images, in accordance with some embodiments of the present specification.

In some embodiments, the data corresponding to the 'patient' jacket' is displayed or rendered by the client-side viewing applications at devices 102, 106 though a plurality of GUIs comprising, for example, a first tab configured to display a profile of a patient, a second tab configured to display a list of the one or more studies specific to the patient, and a third tab configured to display analyses of one or more series of the one or more studies wherein the analyses are generated by application of a neural network process or machine learning process (an exemplary process of training and application of neural networks is described with reference to FIG. 14) to the digital images of the one or more series.

In some embodiments, the 'patient jacket' enables providing the user with one or more targeted advertisements, as described in detail under the section titled 'Dynamic Advertising'.

Reconstrucing Images and Maintaining State Information when Sharing Images

In embodiments, viewing applications, such as the client-side viewing applications in devices 102, 106, are configured to process DICOM images and reconstruct them and display as three-dimensional (3D) objects. DICOM images are reconstructed using Multi Planar Reformat (MPR) which results in the generation of two-dimensional image cross-sections. Such images may be generated from, for example, Computed Tomography (CT) or Magnetic Resonance Imaging (MRI) systems, resulting in sagittal, coronal, and oblique views from axial sections. The DICOM images may also be reconstructed using volume rendering and results in generation of 3D realistic images. Use of volume rendering creates two-dimensional (2D) projections of a 3D data set. As such, in one embodiment, a 3D data set may include a group of 2D slice images. In one embodiment, an intersection of cross-section planes in the MPR images is marked in a volume rendering of the images. This markup functionality is provided as a function through the client-side viewing application at device 106. In one embodiment, the intersection of cross-section planes in the MPR images is set in the volume rendering of the images by clicking on the image generated by volume rendering. In some embodiments, clicking on the volume rendering identifies a 3D point.

Figure 4A:
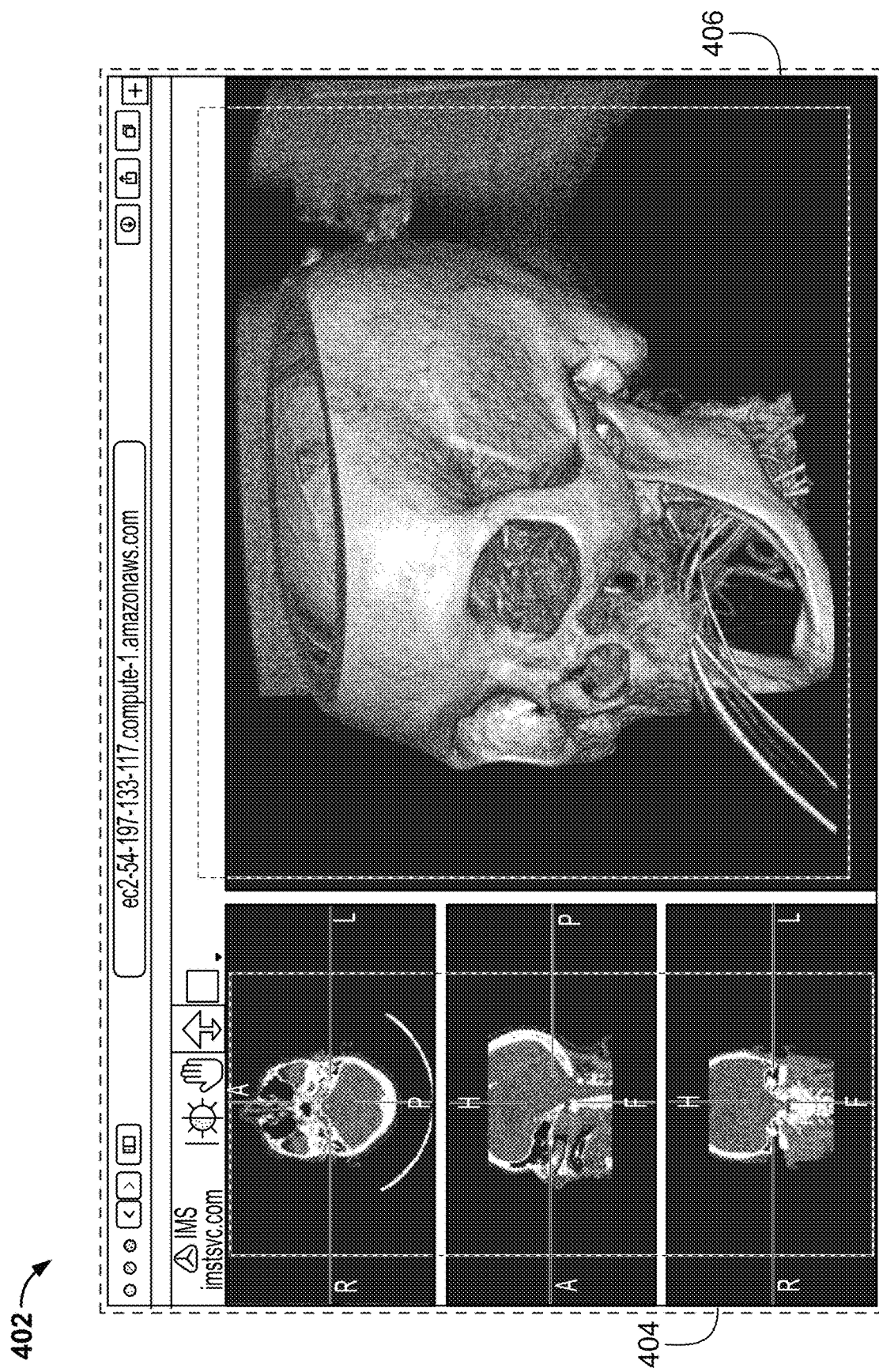
FIG. 4A illustrates an exemplary screenshot comprising 3D images of a skull, in accordance with some embodiments of the present specification.

FIG. 4A illustrates an exemplary screenshot 402 comprising 3D images of a skull, in accordance with an embodiment of the present specification. MPR images 404 are seen on left side and a 3D image generated by volume rendering 406 is seen on the right side of the screenshot 402. In the exemplary illustration, MPR images 404 are generated from a CT study with multiple images.

In embodiments, a user at device 106, through functionality available with the client-side viewing application on device 106, is able to click on a part of the volume rendering 406 to identify a 3D point. An MPR image 404 corresponding to the identified 3D point is then displayed or highlighted along with the volume rendering 406. In some embodiments, users at devices 106 are able to manage the MPR images 404 and volume rendering of images generated by the client-side viewing application at device 106. In one embodiment, a user is enabled to clip an image generated by volume rendering, within a box, where the boundaries are manipulated in the MPR views.

In one embodiment, the user at device 106, through the client-side viewing application, is enabled to change view, position, color, transparency of the box used for clipping the image. The information formed by user's changes to the images is herein termed as "3D State Information".

User may use tools such as polyline, freehand, or magnetic line to modify one of the 2D images (MPR images) in the 3D data set. With the polyline, the user is able to click points on the image, and these points automatically connect once the user is finished clicking the points. With freehand, the user is able to drag and draw an area over the image. Magnetic lines may enable users to create lines that automatically snap to annotations or certain body parts seen in an image. To use magnetic lines, the user may click at a point to start and then as the user moves the pointer, the magnetic line snaps to the closest edge of the image or other lines drawn into the image. The closest edge may be analyzed to be the one that can pass before reaching a current location of the pointer, in a snapshot of the image.

More specifically, in one embodiment, the client viewing application comprises programmatic logic that, when executed, propagates a visual marker, made by a user onto an image, to one or more adjacent images by first prompting the user to select a type of anatomical body, such as a lesion, being visually identified. The type of anatomical body may be defined in a plurality of different ways by one or more pixel parameters but is preferably defined by referring to a brightness level. Accordingly, in one embodiment, the user is prompted to identify whether he is selecting a bright structure or a dark structure, wherein a bright structure is defined by a pixel brightness greater than a predefined threshold value and a dark structure is defined by a pixel brightness less than a predefined threshold value. The programmatic logic further performs a processing of the image to insure each of the images being viewed by the user is defined by a same zoom and/or window level, the image is filtered with a predefined filter, such as a Gaussian filter, and a mask is applied to the images, such as a Canny Edge mask.

With the type of anatomical structure defined (bright or dark) and the image pre-processed, the programmatic logic identifies an initial location of a visual marking by the user and follows the visual marking across a plurality of points on the image. The programmatic logic applies a path finding process to determine a proper path between the two points which, when executed, "snaps" the path to the edge of the volume of interest. In one embodiment, it does so by using the mask, such as the Canny Edge mask, as a cost function where costs are assigned to different brightness points and the path with a minimum cost is determined. Similarly, in one embodiment the path finding process determines a proper path between two points by identifying steepest or largest brightness gradients, which are indicative of a transition between a desired brightness of a volume of interest and a volume of darkness.

Preferably, the programmatic logic presumes a specific movement direction of the user, such as clockwise or counter-clockwise, to make sure the evaluated brightness or darkness level is on the proper side. This automatic adherence of a visual marker, or line, to an edge defining the anatomical or volume of interest, referred to as edge snap or snapping, makes the image modification and manipulation process far more efficient for a physician and eliminates the need for the physician to maintain accuracy while visually marking an entire volume of interest.

In one embodiment, a visual marker that has been inputted by a user and then forced to snap or adhere to edges, as described above, is then propagated by programmatic logic in the client-side viewing application such that the visual marker is replicated across other two-dimensional images which are not marked but display the same volume of interest. In some embodiments, the client-side viewing application, using a volume of interest library, propagates the generated visual marker to a stack of corresponding or associated image slices, thereby enabling an automated process of outlining a 3D lesion in a stack of images. The client-side viewing application is configured to do so by algorithmically projecting points on an initial visual marking, or contour, radially inwards and outwards until the projections contact an anatomical edge in a new image. These projected points can then be joined, as explained above, since anatomical edges correspond to intensity gradients above a predefined threshold. Therefore, the projected or repositioned points may be joined by line segments that follow the edges between them to produce a new lesion boundary. In sum, the client viewing application is configured to identify points on a visual marking in a first image of a plurality of related two-dimensional images, or slices, corresponding to a three dimensional image, project those points toward images adjacent to the first image, identify corresponding points (with comparable pixel characteristics such as brightness or color) in those images adjacent to the first image, and, in any given image with identified corresponding points, join the points using the edge snapping processes described herein and/or the decimation processes described herein.

Figure 13B:
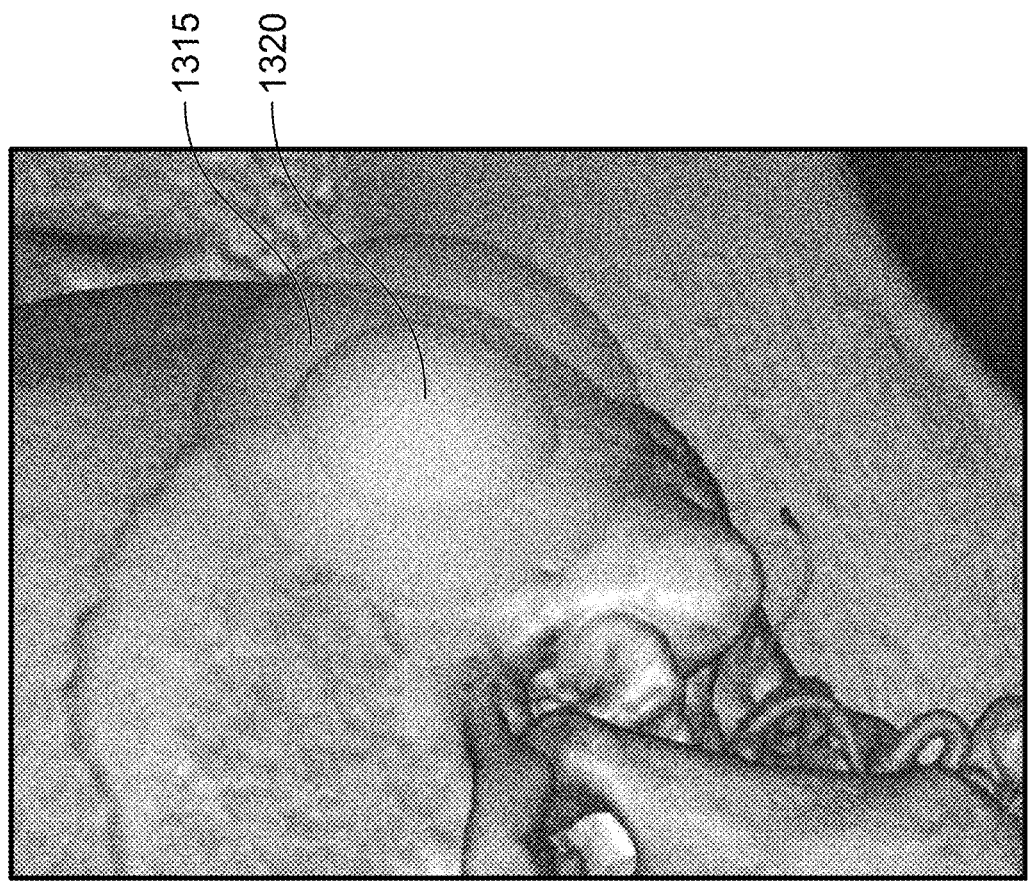
FIG. 13B shows a semi-transparent VOI surrounding a solid VOI, in accordance with some embodiments of the present specification.

With volumes of interest identified, structures may be effectively rendered, as described herein with respect to FIGS. 13A and 13B, measurements of those structures may be made by translating the locations of the pixels delineating the volume of interest into spatial coordinates and using the spatial coordinates to determine length, width, volume, mass (assuming a density of the material in the volume of interest), or other dimensional characteristics, and a dilation of the contoured or demarcated region may be performed to visually highlight or differentiate portions of the volume of interest.

Those skilled in the art may appreciate that several types of tools may be provided to users that allow them to select portions of an image, or otherwise change the image.

The dataset comprising a set of DICOM images is used to generate the MPR and volume rendering and therefore to create a "3D view" which is included in 3D state information. The 3D state information may include several data about the 3D image(s), such as and not limited to at least one of: a) a 3D view direction, b) a definition of 3D cutting planes, c) values indicative of the opacity, transparency and/or colors of the 3D image(s), d) data indicative of the orientation for each of the MPR image(s), or e) data indicative of the degree of 2D pan and/or zoom of each of the MPR and/or 3D images.

In another embodiment, the plurality of options provided by the image viewer application to modify the three dimensional image comprises at least one of modifying a view direction of the plurality of two-dimensional image slices, modifying a cutting plane of the plurality of two-dimensional image slices, modifying values indicative of the opacity, transparency, or color of the plurality of two-dimensional image slices, modifying an orientation of one or more of the plurality of two-dimensional image slices, modifying an orientation of one or more of the plurality of two-dimensional image slices, or modifying data indicative of a degree of pan or zoom of one or more of the plurality of two-dimensional image slices. As the user interacts with the image(s) through the client-side viewing application to understand the patient anatomy, the state of the image(s) may be changed based on the above-stated parameters.

The changed state then can be saved and stored in a specifically defined or formatted data object. In one embodiment, the specifically defined or formatted data is a Grayscale Softcopy Presentation State (GSPS) object that specifies the information used to present (display) images. For example, it may include specifications for the output grayscale space, grayscale contrast transformations, mask subtraction for multi-frame images, selection of the area of the image to display, selection of whether to rotate or flip the image or a selection of the image, and annotations. It may further include specific fields, also referred to as labels, tags, data structures, or modules, associated therewith, such as patient identifiers, study definitions, series definitions, equipment definitions, presentation state identification, presentation state shutter, mask, display shutter, bitmap display shutter, overlay planes, overlay activation, displayed area, graphic annotation, spatial transformation, graphic layer, graphic group, modality, and/or volume of interest. The 3D GSPS object and stored in the archives, such as cloud archives 114/116, for later review.

Preferably, data indicative of the 3D state information of an image, including at least one of: a) a 3D view direction, b) a definition of 3D cutting planes, c) values indicative of the opacity, transparency and/or colors of the 3D image(s), d) data indicative of the orientation for each of the MPR image(s), or e) data indicative of the degree of 2D pan and/or zoom of each of the MPR and/or 3D images, that is defined by a physician is serialized into a private tag, which is inserted into the GSPS object, and the GSPS object in turn is inserted in the study being viewed. In some embodiments, a new DICOM file is generated with the private DICOM tag and the file is inserted in the study. The private tag, which may abide by or conform to the DICOM format, ensures that the private state data is shared with the user through the caching and syncing device 108 and/or through cloud platforms 110/112 but that only the client-side viewing applications supported by devices 102, 106 are able to interpret the private 3D state information. Accordingly, the private DICOM tag is a field associated with the image data object that is specific to, and only readable by, a viewing application with specific authorization or permission to view such a field. In some embodiments, however, the data indicative of the 3D state information of an image is serialized into public tags, wherein the public tags are readable by any client-side viewing application configured to read, render, or display the data object.

In some embodiments, the user may share the saved state of the 3D view through a virtual address, URL or link in an email or a message. The recipient, by clicking the link is redirected to the cloud whereby the recipient is able to view the same saved 3D view.

Further, embodiments of the present specification enable the user to save a selected combination or all of the views generated in MPR mode. The user may save any of the MPR views as a new group of views in DICOM format, such that the recipient can reload them in the same manner. In some embodiments, 3D views are generated by putting a stack of parallel, or associated, 2D images into a 'volume' and then generate three a plurality of views (stacks), such as sagittal, oblique or coronal, from the volume. Therefore, the 3D views show three 2D images, each of which may be saved independently. The three 2D views may be in any orientation relative to the 3D volume view.

For a smoother presentation, embodiments of the present specification render one image in each of a plurality of orientations to display to the user. Once the user finds a region of interest, such as by using one or more of the tools stated above, the regions of interest are marked using range lines in all the three views. When the user chooses to save the image in the region of interest, the regions of interest marked using range lines are generated within the 'volume' one by one, and then saved to a memory such as at a device 102 or 106. The stack saved in the memory can be shared by the user at a device 106 by first sending it to the DICOM archives 114 and/or file storages 116 through the at least one server 125. Similarly, the stack saved in the memory can be shared by the user at a device 102 by first sending it to the caching and syncing device 108 which then syncs the stack with the DICOM archives 114 and/or file storages 116 through the at least one server 125. The images in the stack are sent one by one to archives 114 or file storages 116. Once archives 114 or file storages 116 receive all the images inside the stack then each image is converted to DICOM format and sent one by one to an image archive.

Figures 5A, 5B:
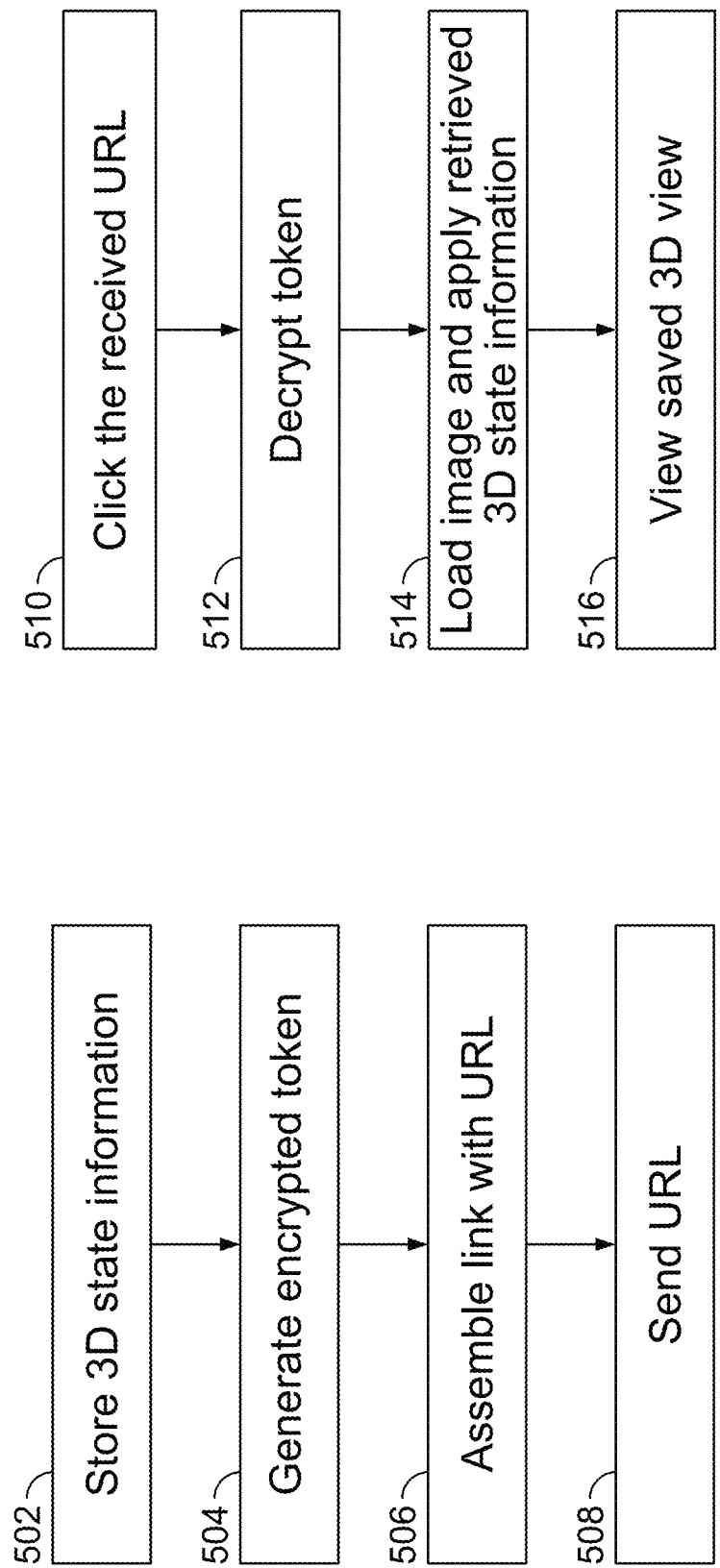
FIG. 5A is a flow chart illustrating an exemplary method for generating a link to view and share a saved 3D image reconstructed by a client-side viewing application, in accordance with some embodiments of the present specification.
FIG. 5B illustrates an exemplary process of accessing the information sent through the virtual address, link or URL through the method of FIG. 5A, in accordance with some embodiments of the present specification.

FIG. 5A is a flow chart illustrating an exemplary method for generating a link to view and share a saved 3D image reconstructed by a client-side viewing application and displayed to a user. For this purpose, the user may choose to execute a function (in the client-side viewing application) to create a link, from the user interface available through the client-side viewing application. At step 502, the client-side viewing application at devices 102, 106, interfacing with the user, is enabled to store the 3D state information of the image being displayed, in to a file or database record. At step 504, an encrypted token is generated. The token may include one or more of, a password, an expiry date of the link or the day of generation of the link, identity (name or number) of the file or database record where the 3D state information is stored, and identity of the user who is creating the link. In some embodiments, the token may include all or none of this information, and includes some other types of information that enables generating the link to the saved 3D image. At step 506, the link is assembled with a virtual address, link or URL that points to a server (such as the at least one server 125 of FIG. 1 that may be separate from or implemented within a cloud platform) that is able to interpret the token generated at step 504. At step 508, the URL is sent to another user (recipient).

FIG. 5B illustrates an exemplary process of accessing the information sent through the virtual address, link or URL through the steps of FIG. 5A, in accordance with some embodiments of the present specification. At step 510, the recipient clicks on the received link. At step 512, the server decrypts the token. In some embodiments, the token is decrypted by services 115 or 117 implemented in the server. Based on the information contained in the token, the recipient is prompted for one or more of a password and the token is checked for its expiry date. Once all the criteria are met, at step 514, image data is loaded and the 3D state information is retrieved and applied to the data. Therefore, at step 516, the recipient is presented with the 3D view in the same state as the user generated in step 502 of FIG. 5A. In this way, an image may be customized, where one of a plurality of different functions are applied to the image, to thereby create an image in a first state and may be shared such that a user who clicks on a shared link will be presented with the image in the first state, thereby obviating the need for the user to apply those plurality of different functions to the image to reconstruct the first state.

Similarly, the embodiments of the present specification are applied to generate 2D state information and share a link to a saved 2D view. In some embodiments, however, 2D state information may not be stored in a file or a database, and may be included as a part of the token or embedded in the virtual address, such as by describing it in a universal resource locator (URL).

Cinematic Rendering

Figure 4B:
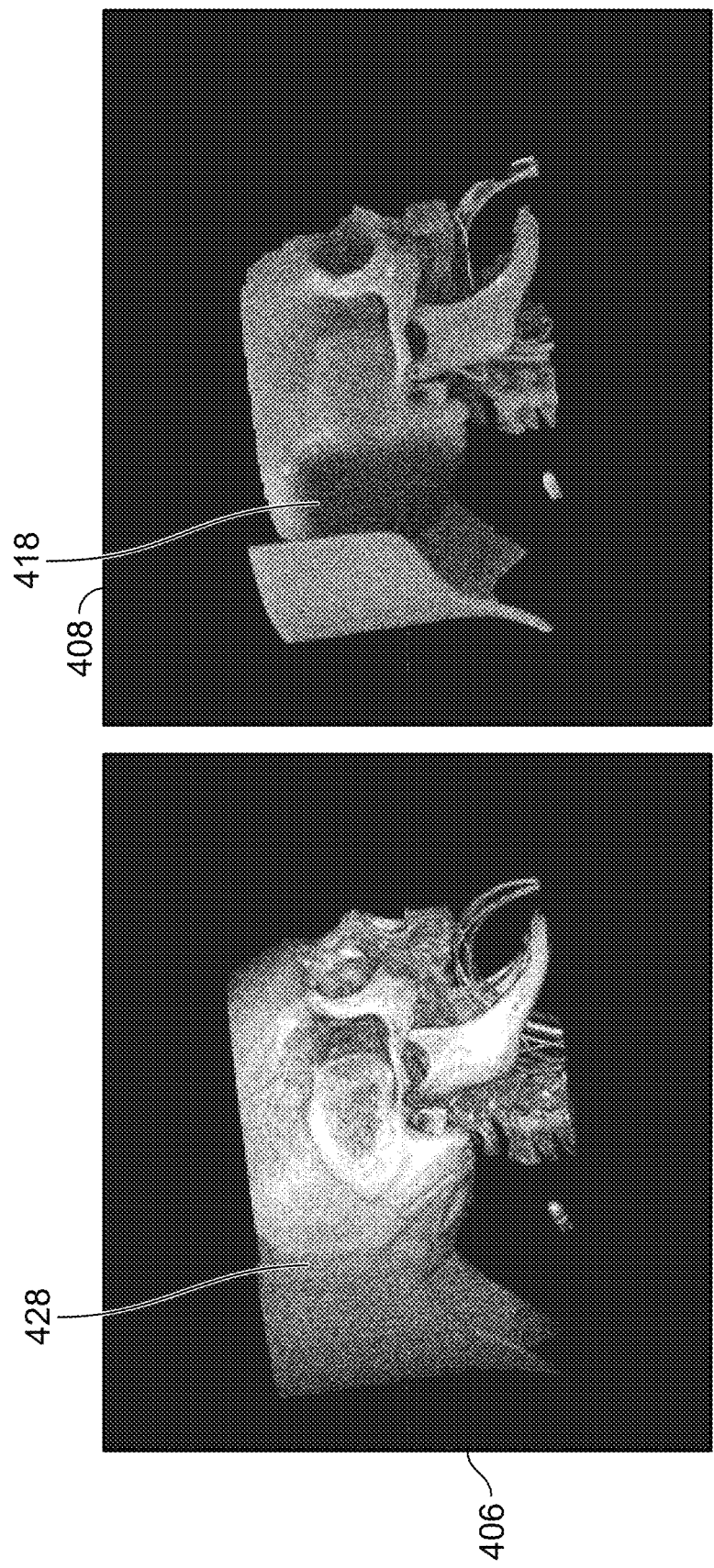
FIG. 4B shows a 3D image reconstructed using prior art volume rendering techniques and another 3D image reconstructed using cinematic rendering process of the present specification.

In some embodiments, the client-side viewing application is configured to process the DICOM images and reconstruct them using cinematic rendering that results in generation of more realistic 3D images compared to those generated using prior art volume rendering techniques. In some embodiments, cinematic rendering comprises a process or method of applying shadow casting to 3D images. As an exemplary illustration, FIG. 4B shows the 3D image 406 reconstructed using prior art volume rendering techniques and 3D image 408 reconstructed using cinematic rendering process of the present specification. Note that in the 3D image 408 reconstructed using cinematic rendering process of the present specification a well-defined shadow is presented 418 while in the prior art image 406, a well-defined shadow does not exist in the corresponding region 428. Casted shadows are computed as follows: a) from each virtual light source which casts a shadow, a depth map is generated, and b) for pixel rendering, its location in the depth map is considered. If the pixel is behind the depth map it will be in shadow, otherwise it will not be in shadow.

It should be appreciated that the key for volume rendering is the definition of the depth map. However, in volume rendering an object is not described by polygons, but by voxels. The voxels are generated by stacking the 2D images acquired by medical imaging devices such as the CT and MR scanners. Furthermore, voxels have associated therewith a color and an opacity which measure the amount of virtual light absorbed by the voxel. So voxels with opacity 1 are fully opaque, while voxels with opacity 0 are fully transparent. Voxels with opacity 0.5 are semi-transparent.

Persons of ordinary skill in the art would appreciate that an adaptation of a casted shadow algorithm to volume rendering is not straightforward, because the definition of the depth map is based on the polygons and it is defined as the z location of the first surface (viewed from the virtual light). The z location is a location along a Z axis normal to a two dimensional plane defining the 2D images. In volume rendering there are no surfaces, but a set of voxels with different levels of opacity. In accordance with aspects of the present specification, the client-side viewing application (at devices 102, 106) implements a method of cinematic rendering that involves 'voxel picking' in order to calculate the depth map. The process of 'voxel picking' is configured to select a voxel with the largest contribution in opacity. The depth map therefore associates, to each part of the volume to render, an opacity and a z location. The opacity measures the 'darkness' of the casted shadow and the z location identifies a location beyond which the shadow is casted.

Figure 5C:
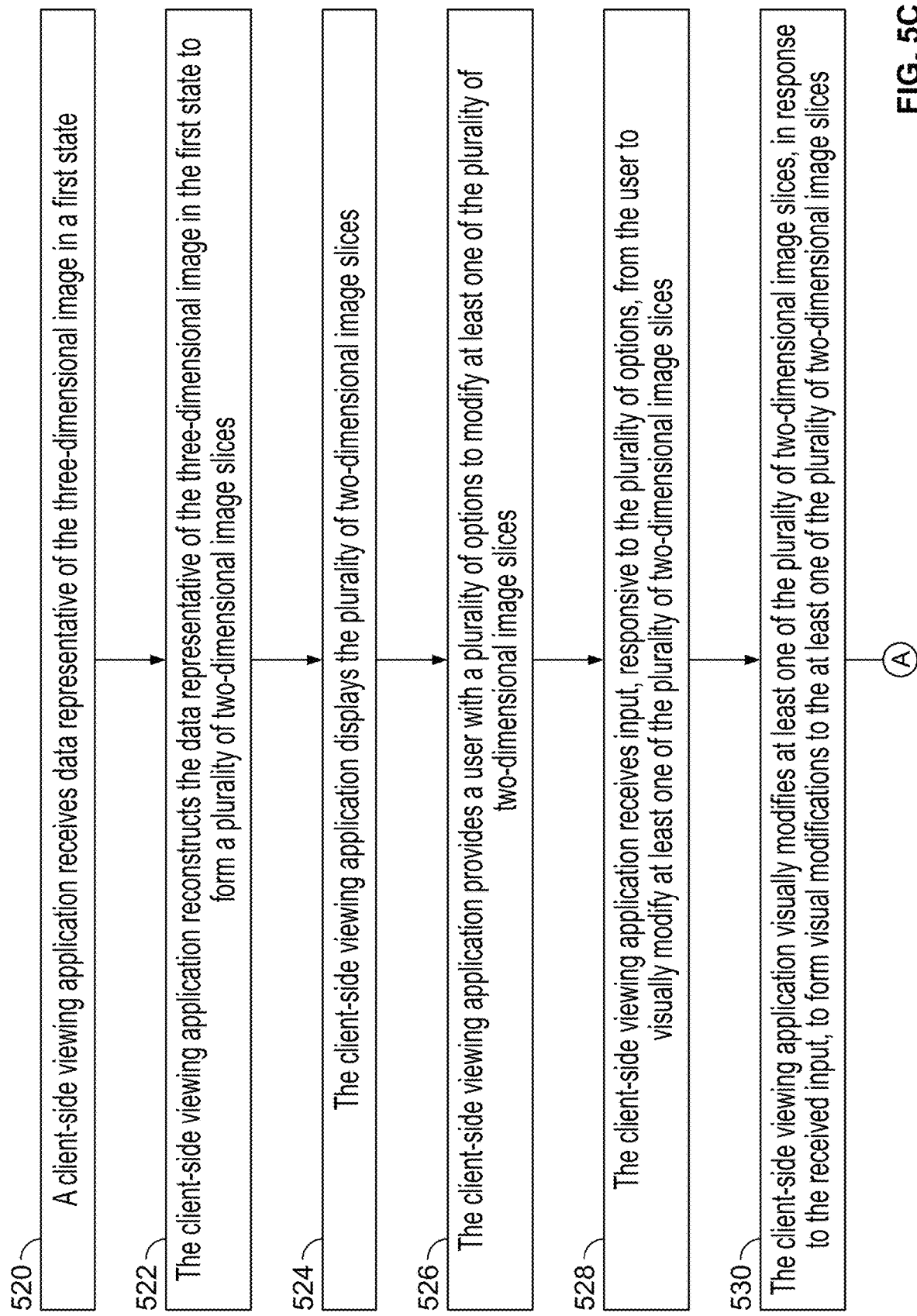
FIG. 5C is a flowchart of a plurality of exemplary steps of a method of receiving, modifying and distributing a three-dimensional image, in accordance with some embodiments of the present specification.

FIG. 5C is a flowchart of a plurality of exemplary steps of a method of receiving, modifying and distributing a three-dimensional image, in accordance with some embodiments of the present specification. In embodiments, the method, being described henceforth, is implemented in the system 100 of FIG. 1. In embodiments, the method is implemented by a client-side viewing application configured to be executed on a device 102/106.

Referring now to FIGS. 1 and 5C, at step 520, the client-side viewing application receives data representative of the three-dimensional image in a first state. In some embodiments, the client-side viewing application receives data representative of the three-dimensional image in an unrendered state.

At step 522, the client-side viewing application reconstructs the data representative of the three-dimensional image in the first state to form a plurality of two-dimensional image slices. In some embodiments, the client-side viewing application reconstructs the data representative of the three-dimensional image using Multi-Planar Reformat. In some embodiments, a portion of the plurality of two-dimensional images is representative of at least a sagittal, coronal, or oblique view of the three-dimensional image.

In some embodiments, the client-side viewing application is configured to apply a virtual light source to a portion of the plurality of two-dimensional image slices to thereby cast a shadow on voxels in the portion of the plurality of two-dimensional image slices. In some embodiments, the client-side viewing application is configured to generate a depth map indicative of a location, along a Z axis normal to a two dimensional plane defining the plurality of two-dimensional image slices, of each voxel in the plurality of two-dimensional image slices. The client-side viewing application is configured to determine which voxels in the plurality of two-dimensional image slices are encompassed by said shadow and to assign an opacity value to at least a portion of the voxels based upon determining which voxels in the plurality of two-dimensional image slices are encompassed by said shadow.

At step 524, the client-side viewing application displays the plurality of two-dimensional image slices. In some embodiments, the client-side viewing application displays the plurality of two-dimensional image slices by rendering the plurality of two-dimensional image slices.

At step 526, the client-side viewing application provides a user with a plurality of options to modify at least one of the plurality of two-dimensional image slices. In some embodiments, the plurality of options comprises at least one of modifying a view direction of the plurality of two-dimensional image slices, modifying a cutting plane of the plurality of two-dimensional image slices, modifying values indicative of the opacity, transparency, or color of the plurality of two-dimensional image slices, modifying an orientation of one or more of the plurality of two-dimensional image slices, or modifying data indicative of a degree of pan or zoom of one or more of the plurality of two-dimensional image slices. In other embodiments, the plurality of options does not comprise modifying values indicative of the opacity, transparency, or color of the plurality of two-dimensional image slices because those values are associated with the recorded intensities of the image, which vary throughout the image, and are not subject to a universal value.

In some embodiments, the plurality of options includes a contouring tool, wherein, when executed by the user, the contouring tool is configured to visually identify edges of an anatomical region of interest in at least one of the plurality of two-dimensional images. In some embodiments, the client-side viewing application propagates the visual identification of the edges of the anatomical region of interest in the at least one of the plurality of two-dimensional images to a remaining portion of the plurality of two-dimensional images to thereby visually identify edges of the anatomical region of interest in the remaining portion of the plurality of two-dimensional images. In embodiments, the client-side viewing application automatically propagates said visual identification without further manual intervention upon a completed execution of the contouring tool.

At step 528, the client-side viewing application receives input, responsive to the plurality of options, from the user to visually modify at least one of the plurality of two-dimensional image slices. In various embodiments, in response to the received input to form visual modifications to the at least one of the plurality of two-dimensional image slices, the client-side viewing application is configured to modify at least one of values indicative of a view direction of at least one of the plurality of two-dimensional image slices, a cutting plane of at least one of the plurality of two-dimensional image slices, values indicative of the opacity, transparency, or color of at least one of the plurality of two-dimensional image slices, values indicative of an orientation of at least one of the plurality of two-dimensional image slices, or values indicative of a degree of pan or zoom of at least one of the plurality of two-dimensional image slices.

At step 530, the client-side viewing application visually modifies at least one of the plurality of two-dimensional image slices, in response to the received input, to form visual modifications to the at least one of the plurality of two-dimensional image slices.

At step 532, the client-side viewing application forms a data object comprising pixel data representative of the visual modifications to the at least one of the plurality of two-dimensional image slices, wherein the data object has public tags associated therewith. In some embodiments, the data object is a grayscale softcopy presentation state (GSPS) object. In some embodiments, the data object is a modified version of the three-dimensional image. In embodiments, the public tags are readable by any viewer configured to read, render, or display the data object. It should be appreciated that the formed data object may not actually include the pixel data representative of the visual modifications to the at least one of the plurality of two-dimensional image slices, wherein the data object has public tags associated therewith, but, rather, a reference to a virtual location comprising that pixel data.

At step 534, the client-side viewing application generates at least one private tag comprising data descriptive of the visual modifications to the at least one of the plurality of two-dimensional image slices. At step 536, the client-side viewing application associates the at least one private tag with the data object. In embodiments, the at least one private tag is only readable by a viewer configured to read, render, or display the data object and configured to have permission to access the at least one private tag.

At step 538, the client-side viewing application transmits the data object. At step 540, the at least one server 125 receives the data object from the client-side viewing application and stores the data object in at least one archive 114, 116 of at least one cloud platform 110, 112. In some embodiments, the at least one server 125 is configured to publish a link to an address (or virtual address) and be responsive to a request for a link to the address, wherein the address is indicative of a memory location of the data object. In embodiments, the at least one server 125 is configured to store the data object without overwriting the three-dimensional image in the first state.

In some embodiments, at least one of the client-side viewing application or the at least one server 125 is configured to generate an encrypted token comprising an identity of a location of the data object stored in the image storage system. At least one of the client-side viewing application or the at least one server 125 is configured to generate within the encrypted token additional data wherein the additional data comprises at least one of a password, an expiration date of a link to the location of the data object, or an identity of the user associated with the data object.

Subsequently, in some embodiments, a second client-side viewing application may receive a virtual address to the data object, retrieve the data object using the virtual address, render the data object and access data in the at least one private tag, and thereafter apply data descriptive of the visual modifications, accessed from the at least one private tag, to the data object.

Medical Imaging Processing Functions

Referring back to FIG. 1, in some embodiments, the archives 114, 116 (that may implement one or more database systems) of the cloud platforms 110, 112 store instructions or programmatic code corresponding to a plurality of medical image processing functions. In some embodiments, as shown in FIG. 1, the at least one server 125 selectively calls on one or more of the plurality of image processing functions which are invoked and executed in an execution environment of the cloud platforms 110, 112 (such as the execution environment 242 of the system 200). In some embodiments, the at least one server 125 is implemented within the cloud platforms 110, 112 (such as the first layer 205 of the cloud computing system 200 of FIG. 2A). Alternatively, in some embodiments, the at least one server 125 may be a dedicated standalone server and the plurality of image processing functions may be stored in at least one database system associated with the at least one server 125 such that the at least one server 125 may execute one or more of the plurality of image processing functions itself. (The aforementioned embodiments are also referred to as 'server-side' implementation of the plurality of medical image processing functions).

In still alternate embodiments, the plurality of instructions or programmatic code corresponding to the plurality of medical image processing function are integrated into a client-side viewing application of computing devices such as devices 102, 106 and one or more of the plurality of medical image processing functions are called upon or invoked in response to a user accessing, interacting with or manipulating a medical image using the client-side viewing application on his user computing device (also referred to as 'client-side' implementation of the plurality of medical image processing functions).

The at least one server 125 in data communication with the cloud platforms 110, 112 or when implemented within the cloud platforms 110, 112 (such as the first layer 205 of the cloud platform 200 of FIG. 2A) enables a) packaging of the medical image processing functions/methods of the present specification as stateless functions that are executed in small short-lived execution environments or compute units (such as, for example, containers) and b) dynamically scale functions based on user-provided events.

In some embodiments, the plurality of instructions or programmatic code corresponding to each of the processing methods of the present specification is deployed, created or stored on the cloud platforms 110, 112 before executing it. Thus, the system cloud platforms 110, 112 have all the necessary programmatic code to execute the functions, corresponding to the processing methods, when required.

In accordance with further aspects of the present specification, processing in the cloud platforms 110, 112 is based on event driven computing. Thus, when an event occurs a function is invoked in an execution environment which provides the context and execution framework for the job, task or work. If the container is not available, it is instantiated and the function is invoked. After the function finishes the container is stopped. In some embodiments, the execution environment is allowed to remain for some amount of time in case there are more calls to the function invoked. If the function or workload is called infrequently the execution environment may run only a small fraction of the time.

In embodiments, execution of a function can be invoked manually by the user via a command, or it may be triggered by an event that is configured to activate the function in response to events such as, for example, uploading of a medical image study or series, accessing of the medical image study or series and/or user interaction with the medical image study or series on devices 102, 106.

Orientation, Body Part and View Position Detection Function

In some embodiments, a first medical image processing function when invoked and executed enables detection of the orientation, body part and view position of a medical image. View position refers to an angle at which the medical image was taken or acquired relative to a subject's anatomy. For example, the view position could be lateral (LL) or anterior—posterior (AP), for example.

In some embodiments, when an event corresponding to a user sending a request to the at least one server 125 for accessing a medical image occurs, the first medical image processing function is invoked which enables detection of the orientation, body part and view position of the medical image. In other embodiments, this first medical image processing function, which enables detection of the orientation, body part and view position of the medical image, is invoked, performed, or otherwise executed by the server, remote from the client-side viewing application, when a data archive in data communication with the server first receives the image and without requiring an express action by a user, such as requesting the image or requesting a modification of the image. In other embodiments, this first medical image processing function, which enables detection of the orientation, body part and view position of the medical image, is invoked, performed, or otherwise executed by the client-side viewing application.

In some embodiments, detection of the orientation of the medical image enables the medical image to be displayed in a client-side viewing application running on a computing device 102 or 106 of a user in a standard way that the user (such as, for example, a radiologist or a physician) expects, thereby speeding up the diagnoses. In some embodiments, detection of the body part and view position enables determination of how the medical image should be initially displayed and interacted with in the client-side viewing application on the computing device 102 or 106. In some embodiments, data corresponding to the body part and view position are used as search terms for querying the system 100 of FIG. 1.

In some embodiments, information corresponding to the orientation, body part and view position is manually entered or tagged by a clinician or technician when the medical image is acquired at a medical imaging device 104. The information is tagged or associated with the medical image and stored in the system 100. However, being a manual process, it is subject to human error or omission. Empirically, the error or omission rate for the manual entering or tagging is about 10% to 20%. Thus, the first medical image processing function enables automatic detection of information corresponding to the orientation, body part and view position of the medical image at an error rate that is significantly lower than the manual tagging process.

In accordance with some aspects of the present specification the first medical image processing function invokes one of a plurality of trained machine learning models or artificial neural networks that receives the medical image data as input, processes the medical image data and outputs information corresponding to the detection of orientation, body part and view position of the medical image data. In some embodiments, the medical image data provided as input to the machine learning is normalized by, for example, using window level setting in a DICOM image and/or using an entire dynamic range.

In various embodiments, the plurality of trained machine learning models or artificial neural networks comprise at least one of a deep feed forward network, a perceptron network, a feed forward network, a radial basis network, a recurrent neural network, a long term memory network, a short term memory network, a gated recurrent unit network, an auto encoder network, a variational auto encoder network, a denoising auto encoder network, a sparse auto encoder network, a Markov chain network, a Hopfield network, a Boltzmann machine network, a restricted Boltzmann machine network, a deep belief network, a deep convolutional network, a deconvolutional network, a deep convolutional inverse graphics network, a generated adversarial network, a liquid state machine, an extreme learning machine, an echo state network, a deep residual network, a Kohonen network, a support vector machine network, a neural Turing machine network, or a convolutional neural network with transfer learning network.

In some embodiments, the machine learning model is a deep learning feed-forward network such as a multilayer convolutional neural network (CNN). Persons of ordinary skill in the art would understand that each layer of the multilayer CNN has a weight matrix associated therewith that is determined during learning, also referred to as a training stage. In accordance with some embodiments, the CNN is trained using supervised training methodology that involves use of human-labeled set of training data comprising a sufficiently large set of medical images.

In one embodiment, the training data comprises approximately 500,000 thumbnail X-ray DICOM medical images from one or more PACS (Picture Archiving and Communication System) systems. A list is also generated comprising important body parts and view positions that had to be identified by the CNN. For example, body parts included skull, cervical spine, thoracic/lumbar spine, thorax, abdomen, pelvis and extremity while the view positions included lateral, anterior-posterior and oblique. Sample DICOM images for each kind of aforementioned body parts and view positions are also obtained.

Figure 6:
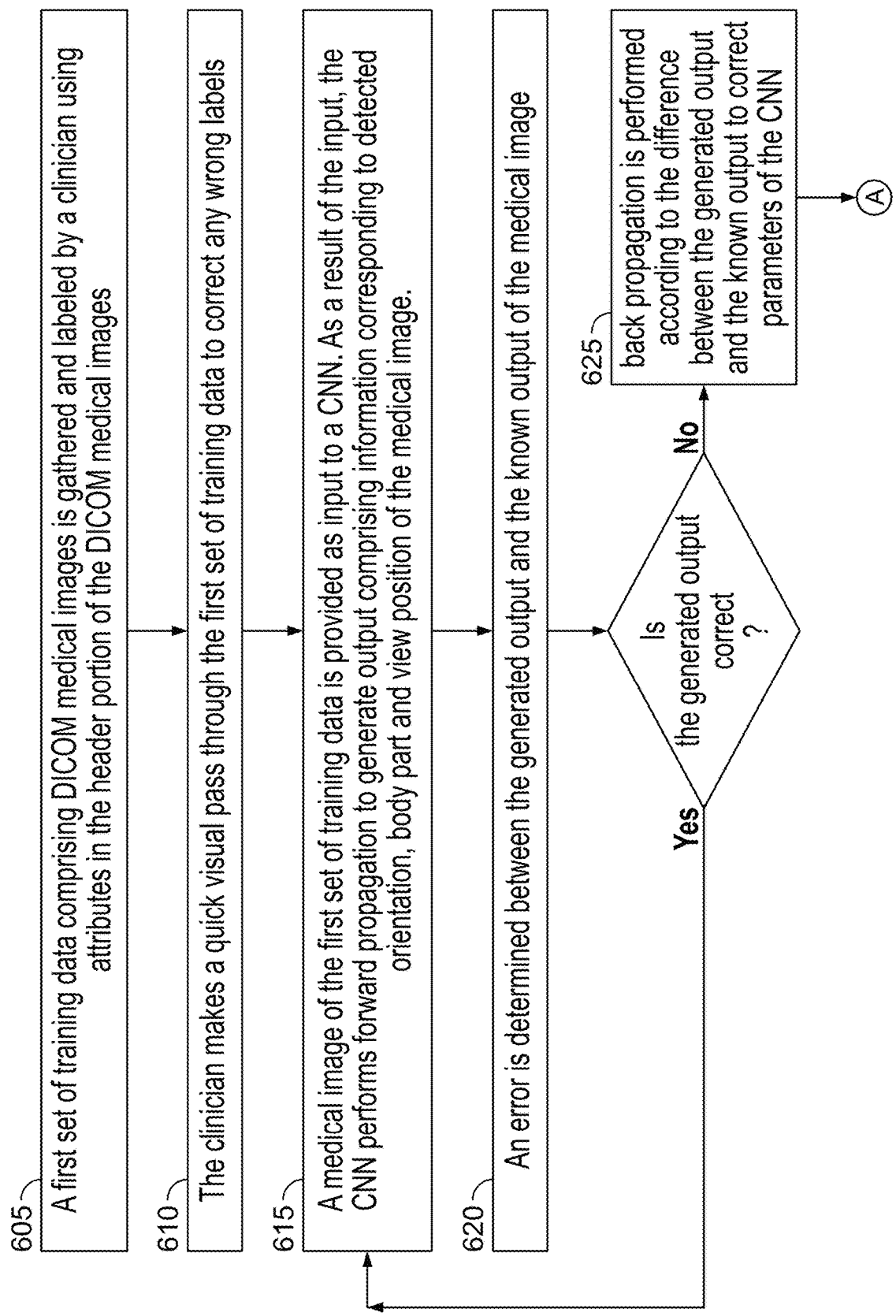
FIG. 6 is a flowchart of a plurality of exemplary steps of a method of training a CNN to detect orientation, body part and/or view position of a DICOM medical image, in accordance with some embodiments of the present specification.

FIG. 6 is a flowchart of a plurality of exemplary steps of a method of training a CNN to detect orientation, body part and/or view position of a DICOM medical image, in accordance with some embodiments of the present specification. At step 605, a first set of training data comprising DICOM medical images is gathered and labeled by a clinician using attributes in the header portion of the DICOM medical images. In some embodiments, the first set is a sub-set of a universe of training data comprising approximately 500,000 thumbnail X-ray DICOM medical images. In some embodiments, the first set of training data comprises approximately 105,000 DICOM images.

At step 610, the clinician makes a quick visual pass through the first set of training data to correct any wrong labels. It should be appreciated that at the end of the visual review the first set may still contain some incorrect labels owing to the quick or cursory nature of the review. It should be appreciated that the visual review is done at a fairly quick pace in order to accomplish labeling the first set of images in a reasonable amount of time.

At step 615, a medical image of the first set of training data is provided as input to the CNN. As a result of the input, the CNN performs forward propagation to generate output comprising information corresponding to the detected orientation, body part and view position of the medical image. At step 620, an error is determined between the generated output and the known output of the medical image (since the medical image is human-labeled for supervised training). In some embodiments, the error is determined and quantified by assigning a score on a scale of, say, 1 to 5 wherein a low score of 1 and 2 is indicative of high error and a high score of 4 and 5 is indicative of low or zero error. If the output is incorrect then, at step 625, in accordance with a learning algorithm—back propagation is performed according to the difference between the generated output and the known output to correct parameters (such as, for example, the coefficients or weight matrices) of the CNN. However, if the output is correct, then the flow moves back to step 615 to continue inputting subsequent medical images to the CNN for processing.

In some embodiments, the learning algorithm is stochastic gradient descent that calculates the error and updates the parameters of the CNN for each sample medical image in the first set of training data. In some embodiments, the learning algorithm is batch gradient descent that calculates the error for each sample medical image in the first set of training data, but only updates the parameters of the CNN after all training examples have been evaluated. In some embodiments, the learning algorithm is mini-batch gradient descent that splits the first set of training data into small batches that are used to calculate the error and update the CNN parameters.

At step 630, the CNN trained on the first set of images is applied to additional set of images. At step 635, the clinician examines a sub-set of images that receive a low score from the additional set of images. These are likely to be images with incorrect labels. At step 640, the clinician manually corrects the incorrect labeling of the images and re-trains the CNN on the now correctly labeled images.

At step 645, additional medical images are introduced to the CNN till the total training data is approximately double the size of the first set of images. Thereafter, steps 635 and 640 are repeated so as to examine the low scoring images, correcting the images that were wrongly labeled and retraining the CNN on the correctly labeled images.

At step 650, it is checked if the overall size of the training data is as large as desired. If yes, the training is terminated at step 655. If no, step 645 is repeated.

As known to persons of ordinary skill in the art, training a CNN necessarily involves trial and error to find the parameters that maximize the accuracy of detection and classification of orientation, body part and view position of medical images. Following are some of the variations of CNN and training thereof that were investigated in some embodiments:

Changing the base network—a best practice for building CNNs for image classification and detection involves starting with a standard, pre-trained network that is known to work well on standard test data, and then modifying the final few layers of the CNN to adapt the network to one's particular problem. Accordingly, in some embodiments, a plurality of open source base networks was tried before training the base network on the training set of medical images in accordance with the method of FIG. 4. The base networks included ResNet50, VGG16, VGG19, DenseNet and InceptionV3. In some embodiments, VGG16 comprised the base pre-trained network.

Using a first alternative wherein a single CNN classifier that predicts a score for all possible combinations of orientation, body part and view position compared to a second alternative of using multiple CNN classifiers—one for orientation, another for body parts and still another for view position detection and classification. Tests on small medical image datasets showed no strong difference between these alternatives. Accordingly, in some embodiments, the first alternative was chosen due to its simplicity and speed of processing.

Combinations of learning parameters—In embodiments, the training method (FIG. 6) of the present specification is executed a plurality of times with various values of the learning rate, batch size, number of epochs and optimizer-type in order to find the combination that gave the highest accuracy rate. It should be appreciated that this is essentially a trial and error process because there are no known rules for determining the best parameter values in advance.

Grouping all of the not relevant body parts images into a single category compared to separating them into many categories based on anatomy type and body part—In some embodiments, both of these alternatives were tried and it was found that there was no significant difference in the accuracy rate for both alternatives. In some embodiments, the not relevant body parts images were divided into sub-categories in various ways but again there was no significant improvement in the results.

Training on all possible image orientations versus training on only the correct image orientation—In the latter case there are fewer training images so training proceeds faster but at detection time all orientations of a given image needs to be input to the CNN and allow it to pick the best one. This is significantly slower and it was found that it was less accurate therefore, in some embodiments, the training method of FIG. 6 was executed on all possible orientations of each image.

Similarity deep ranking—this variation was tried on the standard base network approach and involves training on triplets of images, known as query, positive and negative images, and it returns images that are similar to a given query image. However, it was found that the accuracy of this method of training was poor on small test datasets, so this method was not scaled up to the full size of the training set of images.

In one embodiment, the trained CNN of the present specification produced the following results on images in an exemplary test set containing 1000 images:

TABLE A

|  | Before Application of a trained CNN | After Application of a trained CNN |
|---|---|---|
| Wrong orientations | 106 | 11 |
| Wrong or missing body part tags | 149 | 9 |
| Wrong or missing view position tags | 161 | 5 |

As can be observed from Table A, the number of wrong and missing attributes was reduced by roughly a factor of ten.

Motion Blur Detection Function

In some embodiments, a second medical image processing function comprises a plurality of instructions or programmatic code which when invoked and executed enables automatic motion-blur detection in a medical image acquired using a medical imaging device 104.

In one embodiment, this second medical image processing function is invoked and executed local to the medical imaging device 104 responsible for generating the original image. In other, less preferred embodiments, an event corresponding to the acquired medical image (using a medical imaging device 104) being uploaded by the caching and syncing device 108, to the at least one server 125, causes the second medical image processing function to be invoked. In other, less preferred embodiments, the invocation of the second medical image processing function is particularly advantageous when the caching and syncing device 108 uploads the acquired medical image in real-time—that is, automatically and instantaneously upon generation of the medical image by the medical imaging device 104.

In embodiments, the automatic motion-blur detection function prompts the technician or operator of the medical imaging device (such as, for example, a digital X-ray machine), being used to acquire and generate the medical image, in case the captured image is detected to be blurred thereby obviating a need for the technician to stop and perform a detailed visual inspection of each image acquired. Need for the automatic motion-blur detection is especially great for X-ray scan images taken in the field with a portable device which may not have a high resolution monitor and/or proper viewing conditions.

In some embodiments, the second image processing function is configured to generate a notification if the detected motion-blur indicates that the image is below a predefined quality level, and wherein the at least one server 125, or an application local to the imaging modality, is configured to cause the notification to be transmitted to the imaging modality responsible for generating the digital image to which the second image processing function was applied. In such a scenario, the technician does the imaging of a patient again (instead of releasing the patient only to determine later that the patient's scan image was of insufficient resolution or had motion-blur and therefore requiring the patient to revisit for another scan), else the patient is released.

In some embodiments, the quality level is indicative of whether the images appear sharp or blurred. In some embodiments, the quality level is indicative of whether the images have sufficient resolution. In some embodiments, the quality level is indicative of whether the images appear to have sufficient resolution and/or whether they appear sharp or blurred. In some embodiments, the quality level is indicative of whether the images have sufficient resolution of the finest details in the image.

Motion Blur Detection Method in Accordance with a First Embodiment

Figure 7:
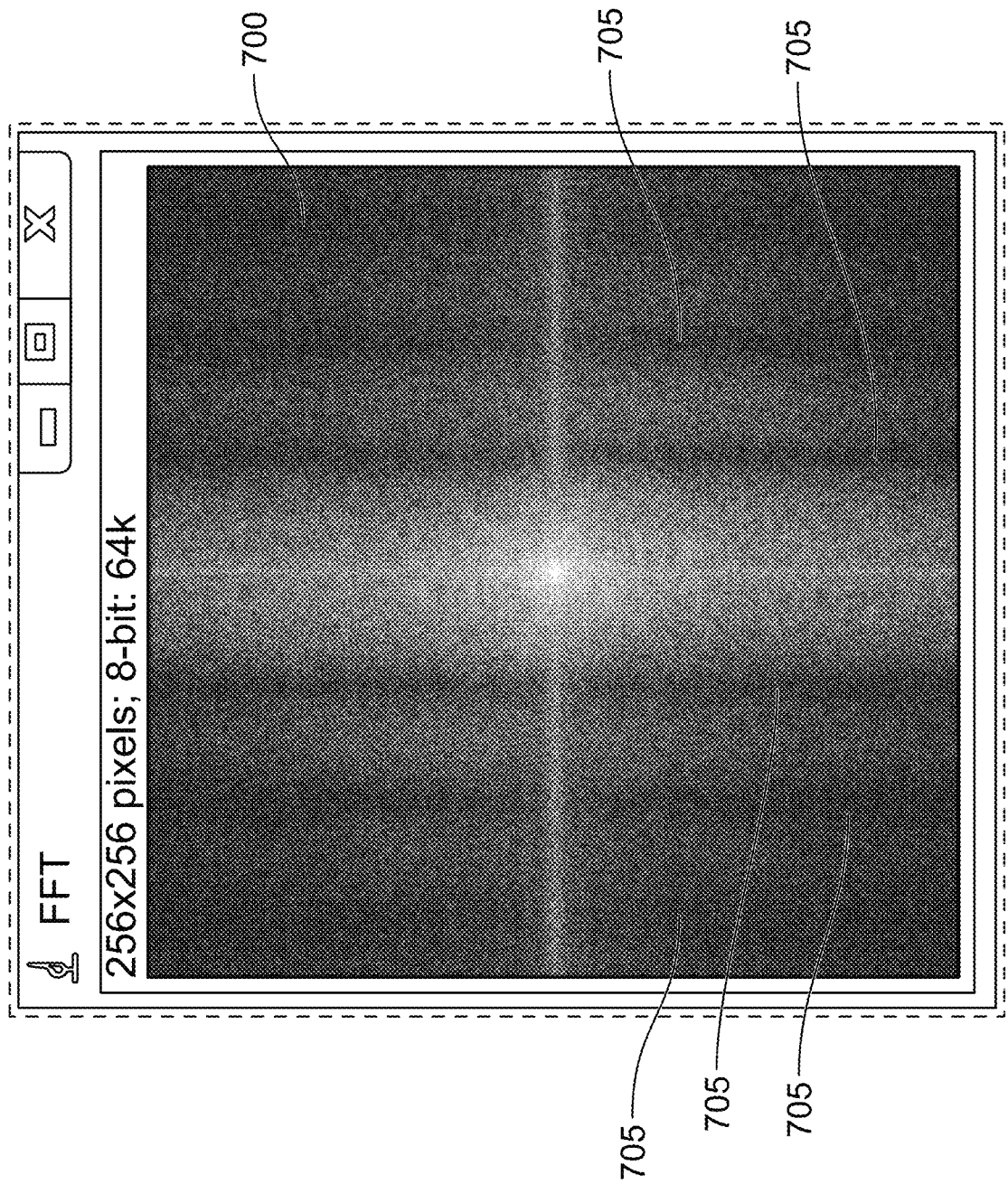
FIG. 7 shows a Fourier transform image, in accordance with some embodiments of the present specification.

In accordance with a first embodiment, the second medical image processing function implements a method for detecting motion-blur using a Fourier transform. It should be appreciated that when an object moves during an imaging process, using a medical imaging device, the resulting blurred image is essentially a convolution of the unblurred object with a kernel that smears it out over several pixels. The Fourier transform of such a convolution can be shown to have nodes—that is, zero lines. For example, FIG. 7 shows a Fourier transform image 700 wherein zero lines 705, e.g. the dark lines in the image, are clearly visible. The method of the first embodiment is directed towards detecting these zero lines in order to detect motion blur.

However, the method of the first embodiment is very sensitive to noise such that even a small amount of noise washes out the zero lines. In case of the medical images acquired, for example, using an X-ray machine, faint zero lines may be visible in only a few of the images thereby confounding the reliability of the method of the first embodiment.

Motion Blur Detection Method in Accordance with a Second Embodiment

For motion-blurred medical images, it is expected that the intensity gradient will be washed out in the blur direction but not in other directions. Consequently, a ratio of perpendicular gradients is likely to be much different from 1 for blurred images. For non-blurred images, the maximum gradient will be roughly the same in both directions and consequently the ratio of perpendicular gradients will be close to 1. Accordingly, in a second embodiment, the second medical image processing function implements the following method for each point in a given image:

At a first step, a square is placed around a point, of size N×N where N is an adjustable parameter. At a second step, at all $N^2$ points inside the square, the intensity gradients is calculated along a pair of perpendicular axes. Thereafter, a maximum ratio (R) of the two gradient magnitudes is determined along the pair of perpendicular axes. Subsequently, at a third step, the pair of perpendicular axes is rotated by 10 degrees and R is recomputed. The steps are repeated for rotation angles ranging from 20 degrees to 360 degrees in increments of 10 degrees and a maximum value for R is recorded.

Motion-Blur Detection Method in Accordance with a Third Embodiment

In accordance with a third embodiment, the second medical image processing function implements a method based on an observation that the power spectra along two perpendicular directions should be approximately the same in an unblurred or sharp medical image since there is no preferred direction. However, if the medical image is blurred along one of the directions then its power spectrum along that direction is smaller at high frequencies.

Motion Blur Detection Method in Accordance with a Fourth Embodiment

In accordance with a fourth embodiment, the second medical image processing function implements a method similar to the ones in the second and third embodiments except that the method of the fourth embodiment compares correlation values for each point in a given medical image, as follows:

At a first step, a square image first patch is considered centered on a point, wherein the patch is referred to as $P_1$. At a second step, a second patch of the same size (as that of the first patch of the first step) is considered, but shifted by a vector V. For example, the vector V=(5,0) corresponds to a horizontal shift of 5 pixels. The second patch is referred to as $P_2$.

At a third step, a correlation of $P_1$ and $P_2$ is computed. This computation is done by first subtracting a mean of each of the first and second patch from itself and dividing by its standard deviation and then computing $$corr = \sum_{x,y} P_1(x, y) \cdot P_2(x, y)$$

It should be appreciated that the correlation will be large if $P_1$ and $P_2$ are similar and small if they are very different. The conceptual idea is that if the image is blurry and V is parallel to the blur direction then the correlation will be large else it will be small.

Finally, at a fourth step, the correlation is calculated for a plurality of angle of V and the maximum value is taken. In some embodiments, the magnitude of V is 4 pixels, as determined by trial and error.

Motion-Blur Detection Method in Accordance with a Fifth Embodiment

In accordance with a fifth embodiment, the second medical image processing function invokes one of a plurality of trained machine learning models or artificial neural networks that receives the medical image data as input, processes the medical image data and outputs information corresponding to the detection of motion-blur in the medical image data.

In various embodiments, the plurality of trained machine learning models or artificial neural networks comprise at least one of a deep feed forward network, a perceptron network, a feed forward network, a radial basis network, a recurrent neural network, a long term memory network, a short term memory network, a gated recurrent unit network, an auto encoder network, a variational auto encoder network, a denoising auto encoder network, a sparse auto encoder network, a Markov chain network, a Hopfield network, a Boltzmann machine network, a restricted Boltzmann machine network, a deep belief network, a deep convolutional network, a deconvolutional network, a deep convolutional inverse graphics network, a generated adversarial network, a liquid state machine, an extreme learning machine, an echo state network, a deep residual network, a Kohonen network, a support vector machine network, a neural Turing machine network, or a convolutional neural network with transfer learning network.

In some embodiments, the machine learning model is a deep learning feed-forward network such as a multilayer convolutional neural network (CNN). Persons of ordinary skill in the art would understand that each layer of the multilayer CNN has a weight matrix associated therewith that is determined during learning, also referred to as a training stage. In accordance with some embodiments, the CNN is trained using supervised training methodology that involves use of human-labeled set of training data comprising a sufficiently large set of blurred and non-blurred or sharp medical images. In some embodiments, the training data comprises DICOM medical images of animals and/or humans. In some embodiments, human labeling of the training data is directed towards assigning a level of sharpness to each medical image. Thereafter, based on the images which have been labeled as blurred a threshold is determined which is used to label an entire image as blurred.

Figure 11:
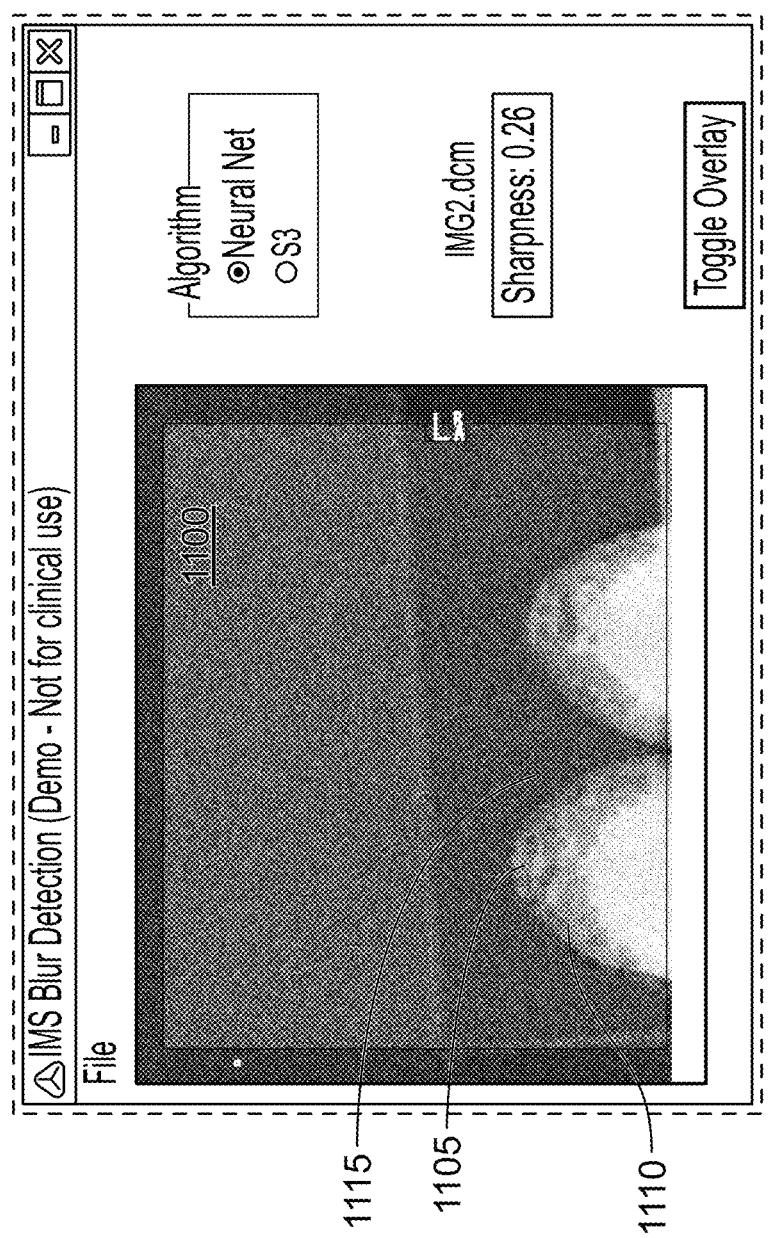
FIG. 11 shows an exemplary image processed using a CNN to detect motion blur, in accordance with some embodiments of the present specification.

In some embodiments, the trained CNN is applied to a task of detecting and classifying small image patches as either sharp, blurred or background. It was observed that the trained CNN can detect blur in small image patches with an accuracy of about 90%. However, this does not translate to accurate predictions of whether the image as a whole appear sharp or blurred to a human observer. In some embodiments, a success rate for the whole-image blur detection task was about 70%. FIG. 11 shows an exemplary image 1100 processed using a CNN to detect blur in images, in accordance with some embodiments. As shown, the green areas 1105 are detected as sharp, the red areas 1110 are detected as blurry and the yellow areas 1115 indicate background or soft tissue.

Motion Blur Detection Method in Accordance with a Sixth Embodiment

In accordance with a sixth embodiment, the second medical image processing function 310 implements a method based on a published algorithm—"S3: A Spectral and Spatial Measure of Local Perceived Sharpness in Natural Images", by Vu et al., IEEE Transactions on Image Processing, Vol. 21, Issue 3, 2012—hereinafter referred to as the S3 method.

The S3 method outputs blur detection results on 8-bit natural images. The S3 method of the sixth embodiment is adapted to 16-bit medical images. However, it was found that the S3 method of the sixth embodiment gave results very similar to the CNN of the fifth embodiment with a slightly worse overall error rate.

Motion Blur Detection Method in Accordance with a Seventh Embodiment

Artificial Intelligence (AI), and more specifically, a neural network, provides algorithms which are able to 'learn' the relationship between input and output. This approach is drastically different from the standard 'coding' approach in which a developer has to find a set of rules that are able to determine an output from a provided input. AI algorithms are more amenable for solving problems in situations for which these rules are not clear, or heuristic, for instance based on the human perception rather than physics or math. In this context, the detection of the blur images in X-Ray applications fits very well.

In accordance with the seventh embodiment, data related to blur and non-blurred images is collected and used to train the AI algorithm. Each time data is provided and validated by one or more users, it is used to further improve the AI and therefore the ability to detect the blur images more accurately.

Figure 12A:
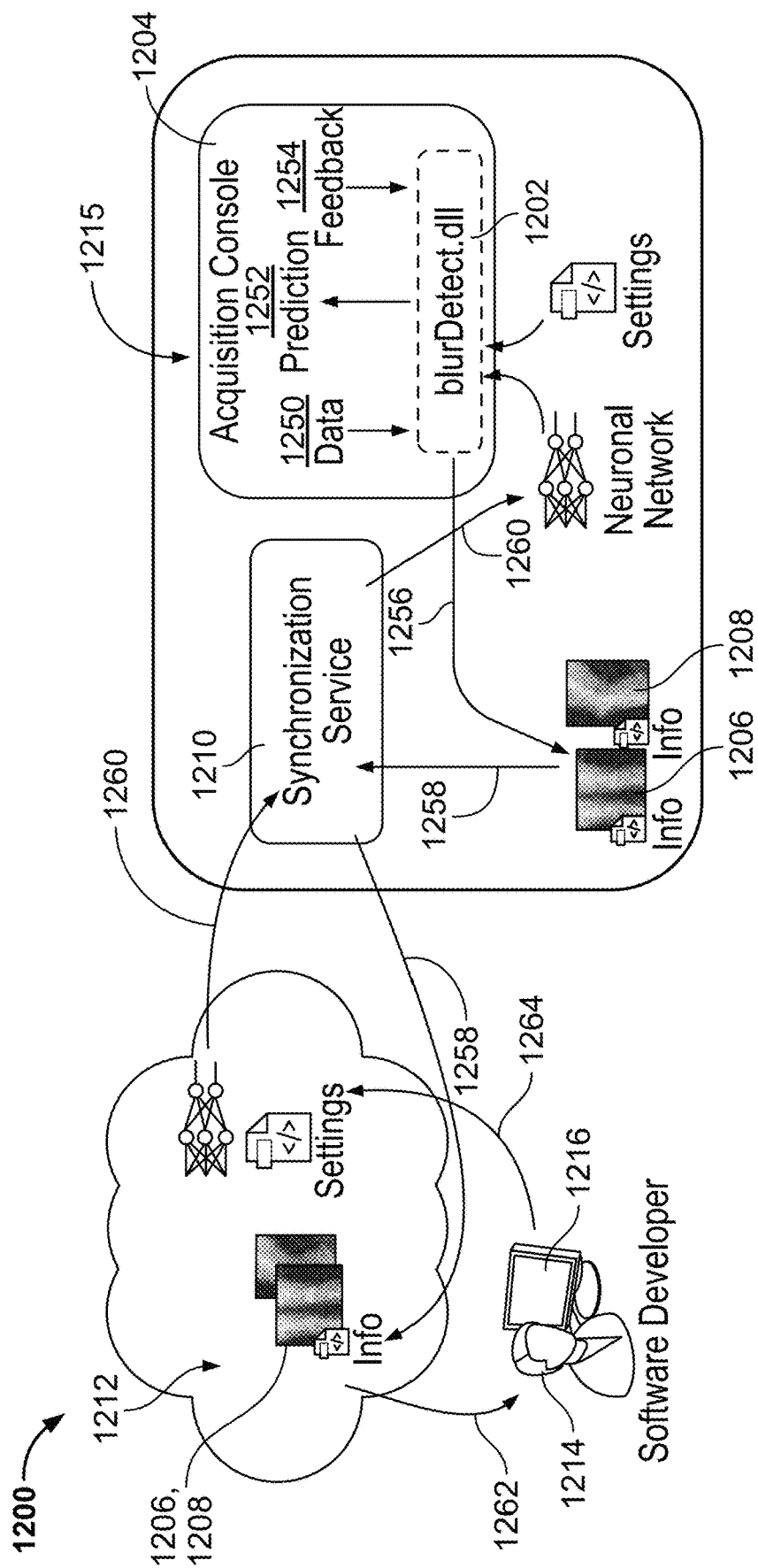
FIG. 12A illustrates an exemplary system that uses AI (Artificial Intelligence) algorithms to detect blur images, in accordance with some embodiments of the present specification.
Figure 12B:
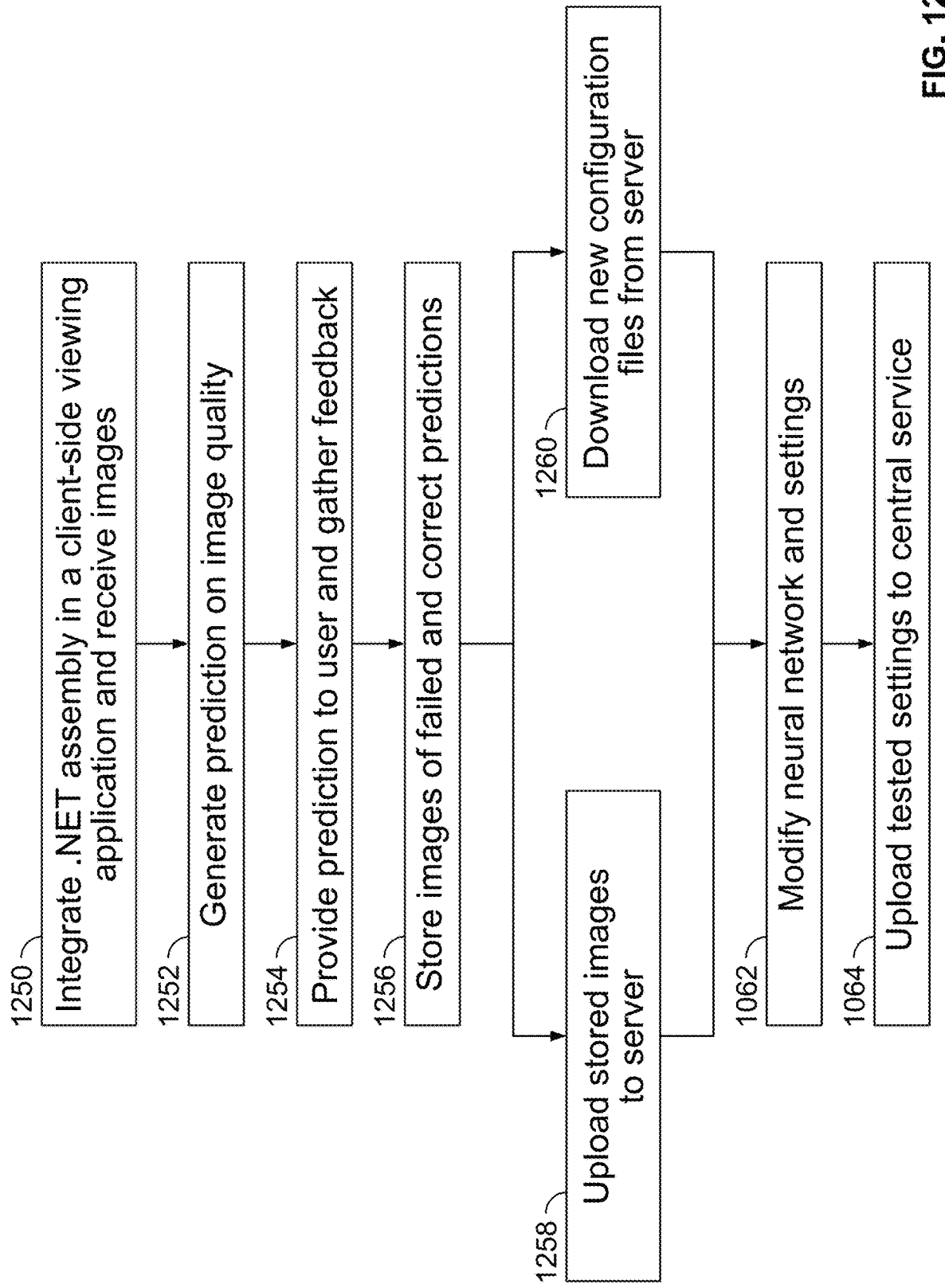
FIG. 12B is a flow chart illustrating an exemplary method of using AI algorithms to detect blur images, in accordance with some embodiments of the present specification.

FIG. 12A illustrates an exemplary system 1200 that uses AI algorithms to detect blur images, in accordance with some embodiments of the present specification. In embodiments, a neural network of FIG. 12A is transparently deployed for use by a user. FIG. 12B is a flow chart illustrating an exemplary method that uses AI algorithms to detect blur images, in accordance with some embodiments of the present specification. Referring to FIGS. 12A and 12B, in some embodiments, the second medical image processing function implements a .NET framework application that includes executable files and libraries for use by a client-side viewing application of a workstation 1204. The workstation 1204 is associated with at least one medical imaging modality or device (such as device 104 of FIG. 1). In some embodiments, at step 1250, a .NET assembly 1202 is integrated in the client-side viewing application, thereby providing it acquisition control functionality, such that the application provides the pixel data and key DICOM tags (step 1250) of an image generated by the at least one medical imaging device. In some embodiments, the images may be accessed from at least one image storage system (such as the system 122 of FIG. 1). In some embodiments, the .NET assembly 1202 may be installed within the workstation 1204. The client-side viewing application drives at least one user interface and provides data and feedback to the assembly 1202.

Referring again to FIGS. 12A and 12B, a workflow of a feedback loop for the neural network is illustrated. In embodiments, the .Net assembly 1202 loads, at runtime, the settings of a neural network and its configuration files, wherein the neural network is used for predicting quality of medical images. The assembly 1202 may be updated while updating the software configuration of the workstation or computing device 1204. At step 1252, the .NET assembly 1202 uses the configuration files available with the workstation 1204 to generate a prediction about a quality level of the images received at step 1250. In some embodiments, the quality level is indicative of whether the images appear sharp or blurred. In some embodiments, the quality level is indicative of whether the images have sufficiently detailed resolution. In some embodiments, the quality level is indicative of whether the images appear to have sufficient resolution and/or whether they appear sharp or blurred. The configuration files used by the .NET assembly 1202 comprise information about the neural network and its settings.

At step 1254, the client side viewing application in the workstation 1204 provides the generated feedback to a user of the workstation 1204 and gathers feedback from the user about an accuracy of the prediction. The feedback is provided to the assembly 1202.

At step 1256, the assembly 1202 stores, in a storage medium (such as the at least one image storage system 122 of FIG. 1, for example), a first plurality of images 1206 in which its prediction failed as well as a second plurality of images 1208 where its predictions were correct. In some embodiments, a caching and syncing application 1210 is installed in a caching and syncing device, such as the device 108 of FIG. 1 wherein the caching and syncing device is in data communication with the workstation 1204, the at least one image storage system and the at least one medical imaging modality over a local area network 1215 (similar to the network 120 of FIG. 1). In embodiments, the caching and syncing application 1210 is in data communication with at least one server 1212 (that may be similar to the server 125 of FIG. 1) through a network that is external to the local area network 1215. The at least one server 1212 may further be in data communication with at least one cloud platform, implemented within the at least one cloud platform or be a standalone server. In some embodiments, the caching and syncing application 1210 (installed on a caching and syncing device, such as the device 108 of FIG. 1) is installed and executed in the workstation 1204 itself.

At step 1258, the caching and syncing application 1210 uploads the first and second plurality of images 1206 and 1208 onto the at least one server 1212. Simultaneously, as shown in step 1260, new configuration files that may be available are downloaded from the at least one server 1212 by the caching and syncing application 1210. Further, at step 1260, the caching and syncing application 1210 transmits the downloaded new configuration files to the workstation 1204 to update the existing configuration files at the workstation 1204. In other words, the caching and syncing application 1210 synchronizes the first and second plurality of images 1206, 1208 and the configuration files (comprising information about the neural network and its settings) between the workstation 1204 and the at least one server 1212.

In embodiments, at step 1262, another user, such as a developer 1214, uses his computing device 1216 to access the images 1206, 1208 available on the at least one server 1212 and to optionally modify the neural network and settings so as to further improve predictions by, for example, correcting one or more tags associated with one or more images or adding additional data into one or more tags associated with one or more images. In some embodiments, the computing device 1216 is in data communication with the at least one server 1212 through a network that is external to the local area network 1215.

At step 1264, once the improved settings are tested, the entire improved neural network may be uploaded on the at least one server 1212 so that they may be distributed to one or more local area networks. In some embodiments, the settings are tested a number of times and each time a new version of settings are deployed for further testing, until final deployment. In some embodiments, the at least one server 1212 also collects a plurality of statistics on the usage of the configuration files for each instance, and the number of correct and incorrect predictions.

Exemplary Case Study for the Seventh Embodiment

In an exemplary case study, the AI algorithms of the present specification were employed for the detection of motion blur on X-ray images with data provided by a data provider.

For the purpose of the case study, a prototype neural network was developed using Google's Tensor Flow library. The neural network was created during a training phase in which the developer decided on a topology of the network and presented to it a number of examples to "learn" from. The prototype neural network was then deployed into a real application where the network is expected to predict an outcome from an unseen sample. Use of the Tensor Flow library decoupled the training phase from the deployment and allowed both training and deployment to occur on different platforms and systems. Once the network was trained, it was saved as a file which could be loaded by an application, such as the client viewing application and/or the at least one server 1215, at a later time. The training phase was an iterative process in which the developer used a set of samples to "train" the network, and a smaller set to "test" its detection quality. Based on the result and performance, the developer was able to change the network topology and/or the training sample to optimize detection. In this exemplary case, the test samples were defined at the beginning and not changed.

The provided sample consisted of 20 pairs of images, wherein within each pair a first image exhibited motion blur while a second image presented the same anatomy without motion blur. The 20 pairs of images, or total of 40 images, were divided into two sets: a training set and a testing set. The training set was used to define the system (and to train the neural network), while the test set was left untouched until the end, for the evaluation of accuracy. The test set was not used for the creation of the neural network nor the evaluation of the network detection until the system was completely built.

The neural network was applied to detect the blur on small patches of the image rather than the image as a whole. Therefore, the images were divided into a number of patches, which in turn were used to train and test the network. A second algorithm was then used to analyse the classification mask determined by the network, and to determine whether the image presented a blur artefact or not. The process involved two stages: in a first stage, an input image was divided into a number of patches, and the neural network was applied to each one of them to determine whether it was blurred or sharp, and in a second stage, the overall map produced by the network was reviewed to determine whether the image was considered blurred or sharp by the user.

Figure 12C:
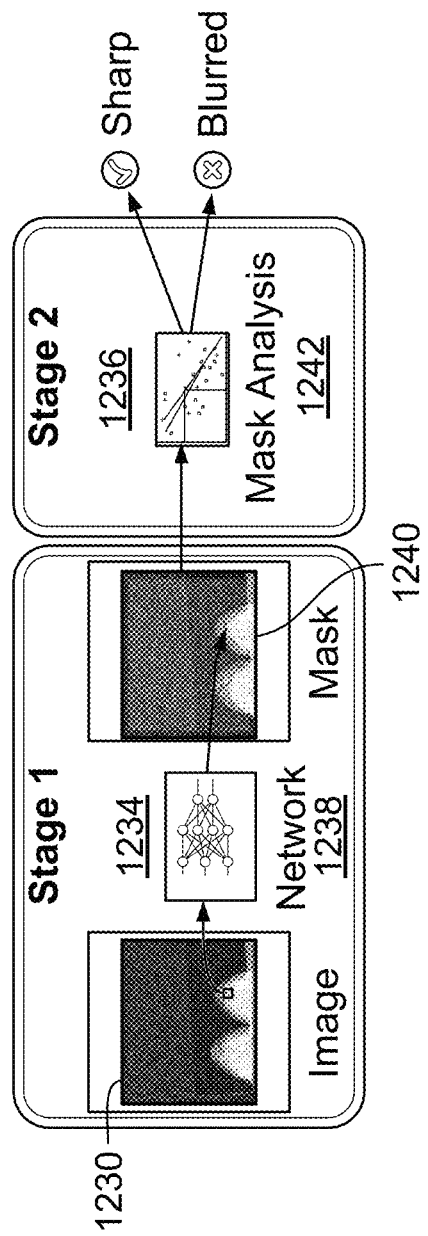
FIG. 12C illustrates an exemplary process for training a neural network to detect motion blur, in accordance with some embodiments of the present specification.

FIG. 12C illustrates an exemplary process of training the neural network with the two stages, in accordance with an embodiment of the present specification. At a first stage, 1234, several iterations on the topology of the neural network and output classes were performed in order to find the best trade-off between accuracy and performance. During the process of topology optimization, a convolutional neural network (CNN) was used and optimized. As a result, the images were classified with a success rate of more than 90%. For the purpose of class definition, the images were divided into patches and the content was classified into: background, tissue, blurred bone, sharp bone, and other (to classify the area of thick bone which otherwise would appear not blurred or sharp). However, when the neural network was trained, the patches classified as 'background', 'tissue', and 'other' were combined into a single category.

FIG. 12C illustrates image 1230 undergoing the process of the first stage 1234, through a CNN 1238, to generate a masked image 1240 that includes the patches. A total of 309 patches were extracted from the training set, where 284 were used to train the CNN 1238, and 25 were used to estimate the accuracy of the detection.

Figure 12D:
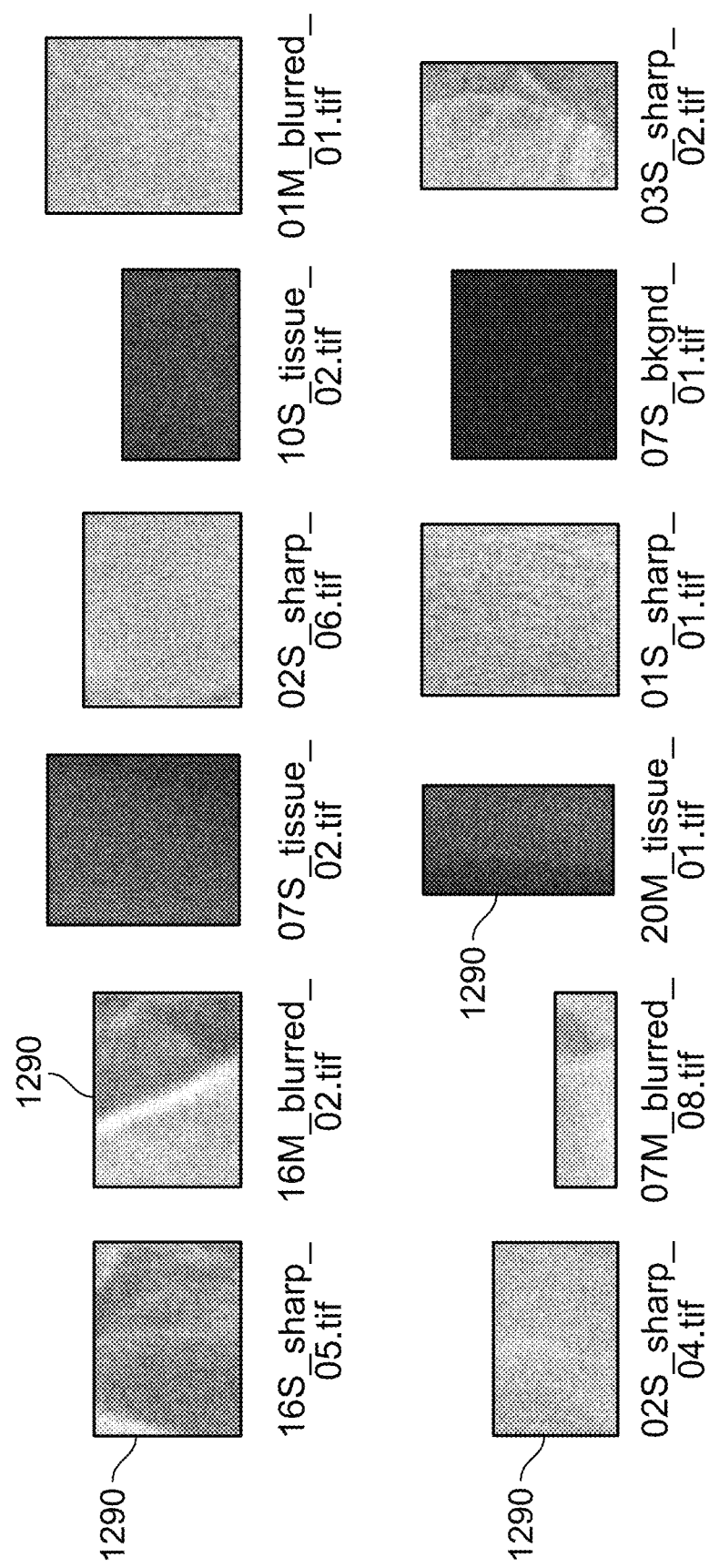
FIG. 12D illustrates a subset of patches used for classification of images using the neural network.

FIG. 12D illustrates a subset of the patches 1290 used for the classification. The CNN 1238 was able to classify the patches with 91% accuracy. At a second stage 1236, an overall map 1242 produced by the neural network 1238 was reviewed. During the review, it was noted that the location of the anatomy was typically in the centre of the image, although the location of the sharp area varied from image to image. The size and percentage of the patches of 'other' class varied significantly across the images. Images that were considered sharp also presented areas that were blurred, indicating that the presence of blurred patches cannot automatically tag an image as being blurred. The size and location of sharp areas in the sharp images varied considerably. Based on the conditions described, the sharpness of an image was defined as:

$$\text{Sharpness} = \frac{\text{'Sharp Bone' Area}}{\text{'Sharp Bone' Area} + \text{'Blur Bone' Area}}$$

An image was considered sharp when the value obtained using the above equation was above 0.38. Using the sharpness value as provided in the above equation, and a threshold of 0.38, 80% of the images in the test set were correctly detected.

Additionally, while reviewing the results, it was noted that the result of the first stage 1234 seemed qualitatively correct across all the images. Also, except for one image pair, the sharpness value for the blurred image was lower than the sharpness value of the sharp image. Therefore, for a pair of similar images, the process was able to determine the sharpest image with 90% accuracy. Further, the exemplary case was processed such that all computations were performed in two seconds with no hardware acceleration, while using an i7 machine with a quad core processor.

The prototype developed in the exemplary case study was found to determine which bone structures were sharp or blurred with an accuracy of 90% and was able to predict whether an image as a whole appears sharp or blurred with an accuracy of 80%. Furthermore, when an image was re-taken, the prototype was able to determine with 90% accuracy whether the new image is sharper than the previous one Therefore, the seventh embodiment can be used to help the user determine whether a new image has to be re-taken, highlight the area that seems blurred, or determine whether the new (re-taken) image is sharper than the previous one.

Segmentation Function

Referring back to FIG. 1, in some embodiments, a third medical image processing function when invoked and executed enables segmentation function and associated features. In some embodiments, when an event occurs, corresponding to a user interacting with or manipulating a medical image using a client-side viewing application on his computing device 102, 106, the third medical image processing function is invoked.

Decimation Feature

In some embodiments, a decimation feature of the segmentation function enables a user to generate and define two dimensional (2D) polylines on at least one GUI (Graphical User Interface) generated by a client-side viewing application in a computing device (such as device 102, 106) to represent outline of anatomical objects on a medical image rendered in the at least one GUI. As known to persons of ordinary skill in the art, a polyline is a continuous line of one or more line segments defined by specifying the endpoints of each segment. In embodiments of 'server-side' implementation of the third medical image processing function, first, second and third methods are directed towards reducing an amount of polyline data that needs to be stored and transmitted over a network to and from between the computing device 102, 106 and the at least one server 125 (FIG. 1). The first, second and third methods are directed towards maintaining the visual appearance of the polyline by limiting a maximum distance between the original and decimated, or reduced set of, polylines. It should be appreciated that the decimation feature disclosed herein is preferably executed by the client-side viewing application.

In accordance with some embodiments, the first method replaces the original polyline by one that has approximately constant spacing between its points to reduce or decimate the number of vertices of the polyline. However, this may not be satisfactory if, in order to significantly reduce the number of polyline points, the spacing becomes excessively large since a large spacing causes unacceptable loss of detail in polylines with sharp corners, which get removed.

Accordingly, in accordance with some embodiments, the second method discards points that are too close to their previous point. The second method, however, does not remove redundant points along long nearly straight portions of the polygon if those points are well-separated. In this embodiment, a minimum threshold distance is applied to determine if a vertex point should be discarded. If the distance is above the threshold, the vertex is maintained. If the distance is below the threshold, the vertex is discarded. In a third method, the client side viewing application recursively subdivides the polyline into smaller segments and replaces each segment with a straight line if and only if a distance between the line and the segment is below a certain threshold. The third method is preferred as it produces satisfactory results.

Point-Snap and Edge-Snap Feature

As discussed above, a snapping, edge snap, or point-snap feature of the segmentation function enables a user to interact with a medical image rendered on at least one GUI of the computing device. The feature enables the user to interact with a medical image by moving a point that the user clicks to the nearest anatomical edge in the image. This allows users to delineate anatomy without needing to be extremely precise when positioning a mouse cursor (which can cause user fatigue and frustration) and further insures consistency of visual markings across different users.

Faint edges present difficulties because a method that is very sensitive to faint edges will often find false edges that are due to image noise rather than true anatomical edges. However, decreasing the sensitivity may cause failure to detect faint edges altogether. Following exemplary method steps are directed towards overcoming the problem of faint edges:

First, image filters are used to reduce image noise. In some embodiments, a median filter is used and its strength is tuned by trial and error to get an acceptable trade-off between noise reduction and loss of faint edges on a set of test images. Though this improves the point-snap results on most images, the median filter can create false edges on some images due to "color banding". To reduce the banding a Gaussian filter is applied before the median filter, in some embodiments. After filtering, a threshold that separates edges from non-edges is chosen. It has been found through experimentation that no single threshold works well on all images. Therefore, in some embodiments, a retry loop is implemented which starts with a very high threshold and decreased until a nearby edge is found.

In some embodiments, an edge-snap feature of the segmentation function supports semi-manual segmentation by snapping a user-drawn contour to nearby anatomical edges. In some embodiments, a method to enable the edge-snap feature comprises computing a cost of all paths between initial and current mouse positions and then selecting the lowest-cost path. In embodiments, a cost of a path is defined such that paths lying along anatomical edges have lower costs than paths that do not.

However, the method was initially found to be too slow. A first improvement is made by changing the dynamic programming algorithm used to compute path costs. Specifically, the stack of as-yet-unexplored paths was kept sorted by cost. This provides a significant speed up.

In a second improvement the cost of all possible paths is not computed up front. Instead, only the low-cost paths leading from the original mouse position to the current mouse position are computed up front. When the mouse is moved to a more distant location, additional paths are computed. This approach provides sufficient performance for interactive segmentation.

Additionally, an acceptable trade-off is determined (based on experimentation) between the smoothness of the edge-snapped contours and their ability to follow sharp corners of anatomical objects. This determination involves trying out a range of parameters in a contour-smoothing routine.

Contour-Sculpting Feature

In some embodiments, a contour-sculpting feature of the segmentation function enables a user to interact with a medical image rendered on at least one GUI of the computing device in order to edit anatomy contours by moving a variable size circular cursor to push a portion of the contour to a new location.

In some embodiments, a method to implement the contour-sculpting feature is based on combining binary masks. A binary mask is essentially an image with only two allowed pixel values—zero and one. In some embodiments, a mask is created for an original contour by setting all pixels inside the contour to one and all other pixels to zero. Similarly, a mask representing the circular cursor is created. These two masks are combined using a logical OR operation and then a border of the combined mask is traced to obtain a modified contour.

However, the method has the following shortcomings: a) a resolution of the final contour is limited by the image resolution resulting in unacceptable "jagged" contours, b) points on the original contour are rounded to the nearest image pixel so that even parts of the contour that are not being edited can move from their original location.

In some embodiments, the aforementioned shortcomings are addressed by changing the method to use polygons rather than binary masks. The two polygons representing the original contour and the cursor are combined by mathematically determining their intersection points and forming a combined contour from the original points plus the intersection points, with interior points discarded.

Propagation Function

Referring again to FIG. 1, in some embodiments, a fourth medical image processing function when invoked and executed enables a propagation function. In some embodiments, when an event occurs, corresponding to a user interacting with or manipulating a medical image using a client-side viewing application on his computing device 102, 106, the fourth medical image processing function is invoked. In embodiments, the propagation function enables a feature wherein once a user identifies a volume of interest (VOI) in one medical image, that delineated VOI automatically propagates to other medical images in a three dimensional (3D) stack of images.

As previously described, in some embodiments, to enable speeding up of a manual process of outlining a 3D lesion in a stack of images, the VOI library implements a method for propagating a user-drawn outline on one image to the lesion boundary on a nearby image. The method is directed towards moving points on an initial contour radially inwards and outwards until they touch an anatomical edge in a new image. In embodiments, anatomical edges are identified with sudden intensity changes in an image—that is, with large intensity gradients. The repositioned points are then joined by line segments that follow the edges between them to produce a new lesion boundary.

Thus, the objective of the propagation function is a) to display 3D graphical objects embedded in rendered volumes. These objects may be used to indicate markers or reference points or to outline other regions such as, but not limited to, lesions. The propagation function may be implemented on any of the modalities described herein.

With the volume of interest appropriately identified, the client viewing application may apply a number of functions to improve the rendered image. In one embodiment, the client viewing application is configured to render VOIs with both occlusion and transparency. The method uses a pair of depth maps: a first depth map for solid VOIs and a second depth map for transparent VOIs. When performing ray tracing the method checks whether the ray has intersected a transparent VOI by checking the first depth map and if so, the method updates the rendered color. The ray is then allowed to proceed and a second depth buffer is checked to determine if there is a solid VOI behind the transparent one. FIG. 13B shows a semi-transparent VOI 1315 surrounding a solid VOI 1320, in accordance with some embodiments of the present specification.

In some embodiments, the VOIs are stored as binary volumes. These are essentially 3D arrays of voxels where every voxel has a value of either 0 or 1 (for points outside or inside the VOI, respectively). However, the arrays can be very large—that is, can use a lot of memory, and also the rendered appearance of the VOI is rough and unnatural, as can be observed from the VOI 1305 of FIG. 13A. In some embodiments, the roughness of the VOI surfaces is reduced by rendering with softer lighting but then the shape of the VOI becomes indistinct and difficult to interpret. Therefore, in a preferred embodiment, the surface of each VOI is approximated by a triangle mesh. These meshes use less memory compared to binary volumes, they can be rendered by standard methods supported in WebGL, and the visual appearance is much better—as can be observed from the VOI 1310 of FIG. 13A.

When multiple VOIs are present in a scene some of them may be partially or fully occluded by others that are closer to the viewer. WebGL has built-in support for rendering with occlusion using a depth map to keep track of which mesh triangles are closer to the viewer. However, depth maps are not compatible with partially transparent VOIs that need to be supported in order to display dilated margins around lesions for surgical planning, for example.

In some embodiments, the client viewing application further comprises shader methods for rendering volumes that contain VOIs. These shader methods are separate from existing non-VOI programs to prevent performance degradation. However, an increased number of shader methods cause an unacceptable application startup delay due to the time required to compile all shaders. Consequently, in some embodiments, each shader is compiled just before it is needed rather than at startup. This results in occasional small delays at run time that are almost imperceptible.

The additional depth maps (discussed with reference to VOI transparency) need to be stored in WebGL texture objects that are essentially memory locations on a graphics processing unit (GPU). Textures are a scarce resource in the sense that the maximum number of textures available on a given GPU is usually quite small often only 8 or 16. Each texture used for a depth map (or other purposes) takes away from the memory available for storing image volumes. Therefore, in some embodiments, the additional depth map textures are compensated by reducing the number of non-volume textures in the WebGL code. This is achieved by re-using the non-volume textures for multiple purposes. Specifically, down sampled images are not given their own texture objects but instead are stored in the same textures used for full resolution images after suitable on-the-fly resizing of the texture buffers.

In various embodiments, a plurality of threshold values is tried to determine whether a particular intensity gradient qualifies as an edge or not. A plurality of values is also tried for allowed range of movement for the points. In some embodiments, too small a range inhibits the contours for adjusting to the new lesion boundary whereas, in some embodiments, too large a range induces them to find spurious non-lesion edges. Accordingly, in some embodiments, outlier points are discarded in order to improve results, wherein the outlier points are those that move much further than their neighbors.

Rendering OCT data—It should be appreciated that OCT is a relatively new technique in medical imaging. Consequently, there are not yet any widely accepted standards for OCT data representation or display. In some embodiments, OCT image data comprises pixel data as a 3D array of floating point values. In embodiments, a method is implemented to support loading of OCT image data comprising floating point pixel values (as opposed to existing methods that can only support loading OCT image data comprising integer pixel values). The method also enables shaded volume rendering of the OCT image data for optimal overall appearance as compared to un-shaded volume rendering.

In some embodiments, the first medical image processing function to detect the orientation, body part and view position, the second medical image processing function to enable automatic motion-blur detection, the third medical image processing function to enable segmentation function and associated features and the fourth medical image processing function to enable a propagation function are deployed and executed on one or more serverless cloud computing systems, on at least one server in data communication with one or more serverless cloud computing systems or on at least one standalone server.

In some embodiments, the first medical image processing function to detect the orientation, body part and view position is deployed and executed on one or more serverless cloud computing systems, on at least one server in data communication with one or more serverless cloud computing systems or on at least one standalone server. However, the second medical image processing function to enable automatic motion-blur detection, the third medical image processing function to enable segmentation function and associated features and the fourth medical image processing function to enable a propagation function are deployed and executed on a user's computing device such as devices 102, 106 of FIG. 1 (that is, at the client-side). In such embodiments, the client-side viewing application supports client side rendering (since the second, third and fourth functions are deployed and executed on the user computing device) that enables the serverless cloud computing system to be stateless—that is, the cloud is not aware of the state of the client and is configured to only enforce security and provide access to medical image data.

In some embodiments, the first medical image processing function to detect the orientation, body part and view position, the second medical image processing function to enable automatic motion-blur detection, the third medical image processing function to enable segmentation function and associated features and the fourth medical image processing function to enable a propagation function are deployed and executed within a client-side viewing application installed on computing devices such as devices 102, 106 of FIG. 1.

Cut-Out Function

In some embodiments, a cut-out feature enables a user to interact with a medical image rendered on at least one GUI of the computing device in order to define a shape within the image and, in response to the defined shape, automatically redraw the defined shape into a separate canvas from the original canvas that contained the image. In some embodiments, the original image on the original canvas is darkened, or colored with black. The separate portion of the image may then be panned or moved around by user using its rotation point and rotation center, as enabled through the user's client-side viewing application. The user may also edit brightness and/or contrast of the image and may edit the color and visibility of the image. Thus, the user may manipulate the images in multiple ways.

Training and Applying Neural Networks

FIG. 14 is a flowchart of a plurality of exemplary steps of a method 1400 of training a plurality of neural networks and providing access to the trained plurality of neural networks for processing one or more digital images, in accordance with some embodiments of the present specification. The method 1400 is implemented in the system 100 of FIG. 1. In some embodiments, the plurality of neural networks are trained using a first set of one or more digital images wherein each of the first set of one or more digital images is associated with at least one of an imaging modality, an anatomy of a person, a diagnosis of the person, an age of the person, a gender of the person, data indicative of contouring, an aggregated score, or a property of the anatomy of the person. An aggregated score may be defined as a health care worker determined value that is a function of one or more metrics or datasets representative of different anatomical or physiological states. For example, the aggregated score may be a Bi-Rads score which is a value indicative of a breast cancer risk category level that is determined by a physician. The breast cancer risk category level can range from 0, which represents an incomplete test, to 1, which reflects a negative mammogram result, to 2 which indicates the mammogram was normal but with benign cysts or masses that should be monitored, to 3 which indicates the mammogram was normal but there's a small percentage chance of having cancer, to categories 4, 5, and 6 which indicate the mammogram indicates there is an abnormality, or actual cancer. Other such aggregated scores, reflective of a healthcare worker's judgment and/or combination of multiple other metrics, may be used.

It should be appreciated that, in some embodiments, the plurality of neural networks need to be trained on other aspects, besides diagnosis. As a non-limiting example, the plurality of neural networks may need to locate anatomy in digital images for which the neural networks need to be trained on contouring of the anatomy associated with the digital images, or properties of the anatomy such as, but not limited to, Bi-RADS (Breast Imaging Reporting and Data System) for mammography or ultrasound images or breast density. In embodiments, digital images have associated metadata that the neural networks are trained for. In some embodiments, this metadata is generated for training by a user using a web viewer (such as the web viewer 271 of FIG. 2B).

In some embodiments, a plurality of instructions or programmatic code associated with the plurality of neural networks is stored in one or more cloud platforms such as the cloud platforms 110, 112 of FIG. 1 such that the at least one server 125 (being separate from but in data communication with the cloud platforms 110, 112 or being implemented within the cloud platforms 110, 112) can make calls to one or more of the plurality of neural networks stored in one or more cloud platforms 110 and/or 112. In some embodiments, where the at least one server 125 is a stand-alone discrete server, the plurality of instructions or programmatic code associated with the plurality of neural networks is stored in at least one archive (implementing a database system) of the at least one server 125.

In various embodiments, the imaging modality is at least one of an X-ray scanning system, an ultrasound imaging system, a fluorescence-based imaging system, a mammography system, a positron emission tomography system, a molecular imaging system, a MM system, or a CT system.

In various embodiments, the plurality of network networks is at least one of a deep feed forward network, a perceptron network, a feed forward network, a radial basis network, a recurrent neural network, a long term memory network, a short term memory network, a gated recurrent unit network, an auto encoder network, a variational auto encoder network, a denoising auto encoder network, a sparse auto encoder network, a Markov chain network, a Hopfield network, a Boltzmann machine network, a restricted Boltzmann machine network, a deep belief network, a deep convolutional network, a deconvolutional network, a deep convolutional inverse graphics network, a generated adversarial network, a liquid state machine, an extreme learning machine, an echo state network, a deep residual network, a Kohonen network, a support vector machine network, a neural Turing machine network, or a convolutional neural network with transfer learning network.

In some embodiments, each of the first set of one or more digital images is in a DICOM format, wherein each of the first set of one or more digital images comprises one or more tags. In some embodiments, the one or more tags of each of the first set of one or more digital images comprises data indicative of the imaging modality, the anatomy of a person, the diagnosis of the person, the age of the person, the gender of the person, data indicative of contouring, the aggregated score, or the property of the anatomy of the person.

Referring now to FIGS. 1 and 14, at step 1402, the first set of one or more digital images is received in at least one client-side viewing application. In embodiments, the at least one client-side viewing application may be that of device 102 or 106. At step 1404, a modification of the first set of one or more digital images is received in the at least one client-side viewing application. In various embodiments, the modification of the first set of one or more digital images is at least one of an annotation of the first set of one or more digital images, a labeling of the first set of one or more digital images with the imaging modality, a labeling of the first set of one or more digital images with the anatomy of the person, a labeling of the first set of one or more digital images with the diagnosis of the person, a labeling of the first set of one or more digital images with the gender of the person, a labeling of the first set of one or more digital images with the age of the person, a labeling of the first set of one or more digital images with data indicative of contouring, a labeling of the first set of one or more digital images with the aggregated score, a labeling of the first set of one or more digital images with the property of the anatomy of the person, an association of one or more visible features in the first set of one or more digital images with a disease state of the person, a visible highlighting of one or more visible features of the first set of one or more digital images with the disease state of the person, a measurement of visible features in the first set of one or more digital images, or a change in an orientation, color, zoom, rotation, brightness, or saturation in the first set of one or more digital images.

At step 1406, the modified first set of one or more digital images is transmitted to the at least one server 125. At step 1408, one of the plurality of neural networks is selected to train based, at least in part, on the imaging modality, the anatomy of the person, the diagnosis of the person, the age of the person, the gender of the person, data indicative of contouring, the aggregated score, or the property of the anatomy of the person associated with the modified first set of one or more digital images. As an example, a first of the plurality of neural networks is selected to train based on a first imaging modality associated with the modified first set of one or more digital images and a second of the plurality of neural networks is selected to train based on a second imaging modality associated with the modified first set of one or more digital images. As another example, a first of the plurality of neural networks is selected to train based on a first imaging modality associated with a first of the modified first set of one or more digital images and a second of the plurality of neural networks is selected to train based on a second imaging modality associated with a second of the modified first set of one or more digital images. In the examples, the first imaging modality is different from the second imaging modality and the first of the plurality of neural networks is different from the second of the plurality of neural networks.

In some embodiments, the at least one server 125 selects one of the plurality of neural networks to train based, at least in part, on data in one or more DICOM tags associated with the modified first set of one or more digital images. In some embodiments, the at least one server 125 selects one of the plurality of neural networks to train automatically upon receiving the modified first set of one or more digital images and determining data in at least one DICOM tag associated with the modified first set of one or more digital images.

At step 1410, the selected neural network is trained based on the modified first set of one or more digital images using the at least one server 125. In some embodiments, after selecting one of the plurality of neural networks to train (at step 1408) and before training the selected neural network (at step 1410), the at least one server 125 applies a quality check function to the modified first set of one or more digital images.

In some embodiments, the training comprises modifying a topology of the selected neural network, a weight associated with one or more nodes of the selected neural network, and/or a number or ordering of one or more layers of the selected neural network.

At step 1412, a request is received, in the at least one client-side viewing application (as a result of a user's interaction with the at least one client-side viewing application), to apply one of the plurality of neural networks to a second set of one or more digital images. In some embodiments, each of the second set of one or more digital images is associated with at least one series, wherein each of the at least one series is associated with at least one study, and wherein the at least one study is associated with only one person and with only one imaging modality.

At step 1414, in response to the request, one of the plurality of neural networks is selected to apply based, at least in part, on an imaging modality, an anatomy of the person, a diagnosis of the person, an age of the person, a gender of the person, data indicative of contouring, an aggregated score, or a property of the anatomy of the person associated with the second set of the one or more digital images. In some embodiments, the selecting of one of the plurality neural networks to apply in response to the request is performed by the client-side viewing application.

At step 1416, the selected one of the plurality of neural networks is applied to the second set of one or more digital images to generate at least one of a graphical, audio, alphanumeric text, or video result. In some embodiments, the selection of one of the plurality of neural networks to apply to the second set of one or more digital images is based, at least in part, on data in one or more DICOM tags associated with the second set of one or more digital images.

At step 1418, the graphical, audio, alphanumeric text, or video result is displayed or played using the client-side viewing application. In some embodiments, the at least one client-side viewing application is configured to generate a graphical user interface comprising a listing of the at least one study (related to the second set of one or more digital images) and at least one of the graphical, audio, alphanumeric text, or video result. In some embodiments, the at least one client-side viewing application is configured to generate a graphical user interface comprising a listing of the at least one study and a link to the at least one of the graphical, audio, alphanumeric text, or video result.

In an exemplary embodiment, each of the second set of one or more digital images represents a portion of a multi-image data set of one person acquired at a same time and using a same imaging modality. In some embodiments, the at least one client-side viewing application, receives a modification of one portion of the multi-image data set and wherein the selected one of the plurality of neural networks applied to the second set of one or more digital images is configured to propagate the modification to other portions in the multi-image data set. In embodiments, the modification is a visual identification of an anatomical feature in said one portion and the propagation of the modification to other portions in the multi-image image data set causes the visual identification of the anatomical feature to be associated with said anatomical feature in the other portions of the multi-image data set.

In another exemplary embodiment, each of the second set of one or more digital images represents a slice of a three-dimensional image and is associated with a computed tomography imaging modality. In an embodiment, when the at least one client-side viewing application receives a modification of one slice of the three-dimensional image, the selected one of the plurality of neural networks applied to the second set of one or more digital images is configured to propagate the modification to other slices in the three-dimensional image. In embodiments, the modification is a visual highlight of an edge of an anatomical feature in the slice and the propagation of the modification to other slices in the three-dimensional image causes the visual highlight of the edge of the anatomical feature to appear in the other slices of the three-dimensional image without manual intervention.

With reference to step 1406, in some embodiments, the at least one server 125 is configured to receive the modified first set of one or more digital images from a first client-side viewing application controlled by a first user and is configured to receive a modified third set of one or more digital images from a second client-side viewing application controlled by a second user such that the first user is different from the second user. In some embodiments, the first client-side viewing application is configured to execute in a first local area network and the second client-side viewing application is configured to execute in a second local area network such that the first local area network is separated from the second local area network by at least one firewall.

Workflows of Various Use Case Scenarios

In embodiments, workflows 1500a, 1500b and 1500c, being described henceforth, are implemented in the system 100 of FIG. 1. In embodiments, the system 100 of FIG. 1 is configured for delivering one or more studies, wherein each of the one or more studies comprises a first series of digital images and wherein the first series of digital images are associated with only one person and generated by only one imaging modality of a plurality of imaging modalities 104. In some embodiments, the association is established using a tag in at least one of the first series of digital images. In some embodiments, each of the one or more studies comprises a second series of digital images, wherein the digital images of the second series is only associated with the one person and generated by a second imaging modality of the plurality of imaging modalities 104, and wherein the second imaging modality is different than the one imaging modality. It should be appreciated that the system 100 is configured to deliver one or more studies wherein each of the one or more studies may further comprises a plurality of series of digital images. However, for purposes of illustration first and second series of digital images have been considered here.

In some embodiments, each of the digital images in each of the first series and/or the second series is formatted in a DICOM format.

In some embodiments, a first of the one or more studies specific to the person is stored in a first cloud-based platform (or a first network of distributed servers) such as the cloud platform 110, wherein a second of the one or more studies specific to the person is stored in a second cloud-based platform (or a second network of distributed servers) such as the cloud platform 112, wherein the first cloud-based platform 110 (or the first network of distributed servers) is programmatically separate and distinct from the second cloud-based platform 112 (or the second network of distributed servers). In some embodiments, the first cloud-based platform 110 (or the first network of distributed servers) is configured to be accessed by a first application program interface and the second cloud-based platform 112 (or the second network of distributed servers) is configured to be accessed by a second application program interface that is different from the first application program interface.

Workflow of a First Use Case Scenario

Figure 15A:
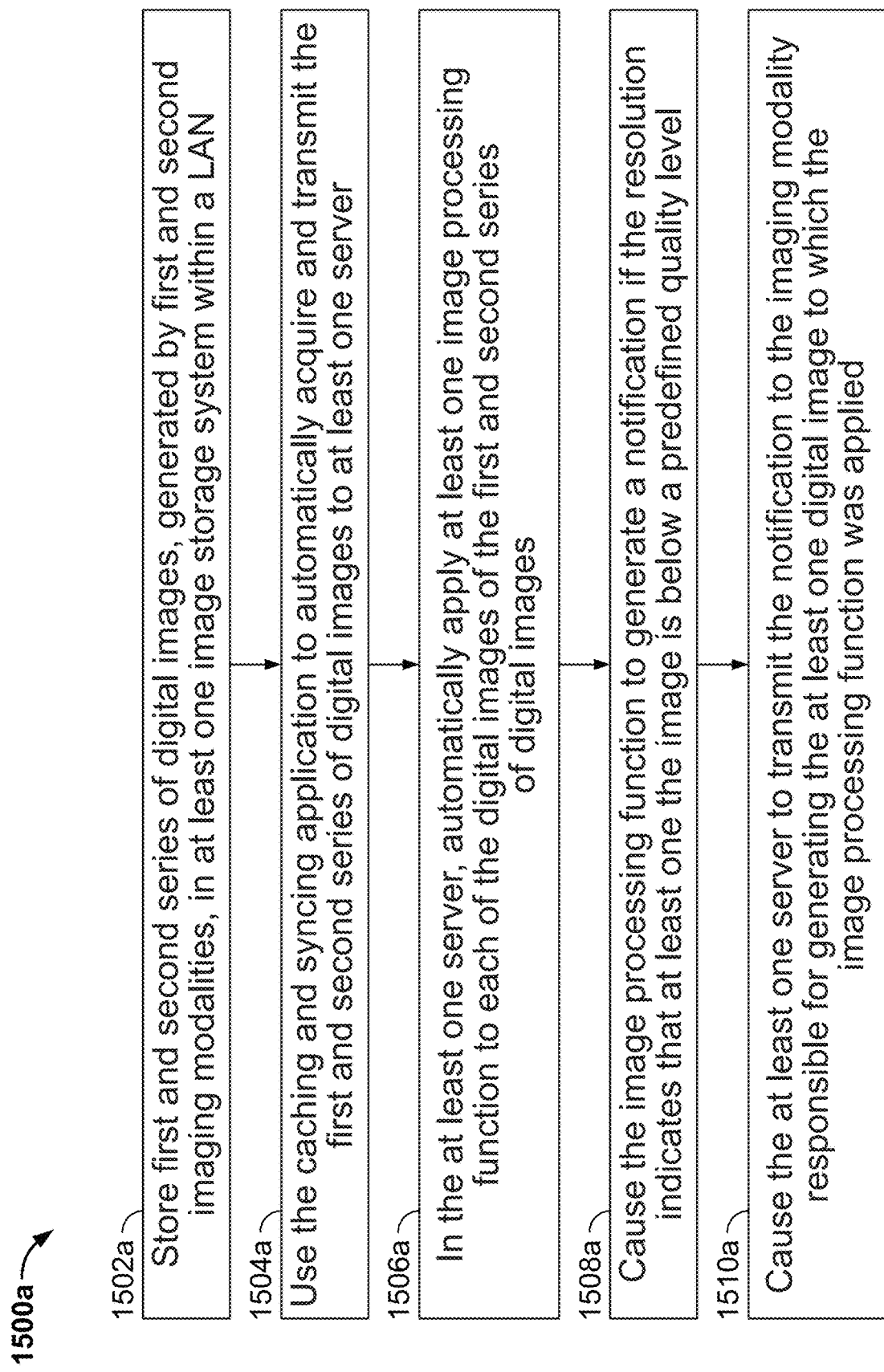
FIG. 15A is a flowchart of a plurality of exemplary steps of a first workflow implemented in the system of FIG. 1, in accordance with some embodiments of the present specification.

FIG. 15A is a flowchart of a plurality of exemplary steps of a first workflow 1500a implemented in the system 100 of FIG. 1, in accordance with some embodiments of the present specification.

Referring now to FIGS. 1 and 15A, at step 1502a, the first and second series of digital images, generated by the one imaging modality and the second imaging modality, are stored in the at least one image storage system 122 within the LAN 120.

At step 1504a, the first and second series of digital images are automatically acquired and transmitted, by the caching and syncing application 109, to the at least one server 125 upon each of the digital images being stored in the at least one imaging system 122.

At step 1506a, the at least one server 125 automatically applies at least one image processing function to each of the digital images of the first and second series of digital images upon receiving each of the digital images. In one embodiment, the image processing function is configured to determine a resolution of each of the digital images. In other embodiments, the image processing function is at least one of an orientation detection, a body part detection, a segmentation function, a decimation function, a point-snap function, an edge-snap function, a contour-sculpting function, a blur detection function, or a propagation function. For example, to apply the image processing function, the at least one server 125 is configured to access, through an application program interface having a predefined format, the image processing function executed by a one or more separate servers and cause the one or more separate servers to apply the image processing function to each of the digital images.

It should be appreciated that the one or more separate servers may be standalone servers, be in data communication with one or more cloud platforms in order to make calls to the cloud platforms for processing functions or be implemented within one or more cloud platforms. In some embodiments, the predefined format of the application program interface is specific to a cloud platform such as, but not limited to, Amazon AWS, Google cloud-based network.

At step 1508a, the image processing function generates a notification if the resolution indicates that at least one the image is below a predefined quality level. In some embodiments, the quality level is defined by a resolution greater than a predefined threshold value.

At step 1510a, the at least one server 125 causes the notification to be transmitted to the one imaging modality 104 responsible for generating the at least one digital image to which the image processing function was applied.

Workflow of a Second Use Case Scenario

Figure 15B:
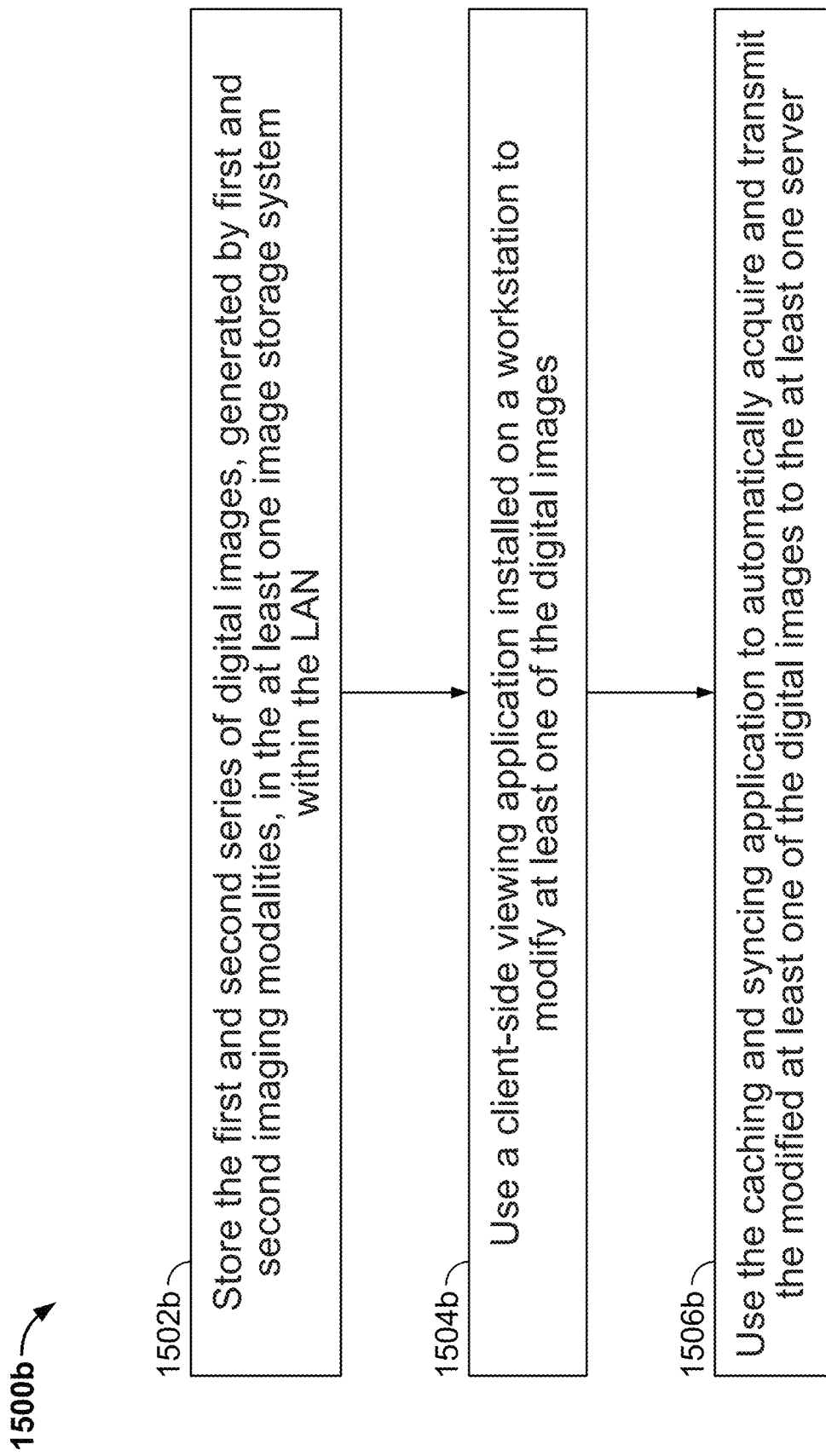
FIG. 15B is a flowchart of a plurality of exemplary steps of a second workflow implemented in the system of FIG. 1, in accordance with some embodiments of the present specification.

FIG. 15B is a flowchart of a plurality of exemplary steps of a second workflow 1500b implemented in the system 100 of FIG. 1, in accordance with some embodiments of the present specification.

Referring now to FIGS. 1 and 15A, at step 1502b, the first and second series of digital images, generated by the one imaging modality and the second imaging modality, are stored in the at least one image storage system 122 within the LAN 120.

At step 1504b, a client-side viewing application installed on the workstation 102 is used to modify at least one of the digital images.

At step 1506b, the modified at least one of the digital images is automatically acquired and transmitted, by the caching and syncing application 109, to the at least one server 125.

Workflow of a Third Use Case Scenario

Figure 15C:
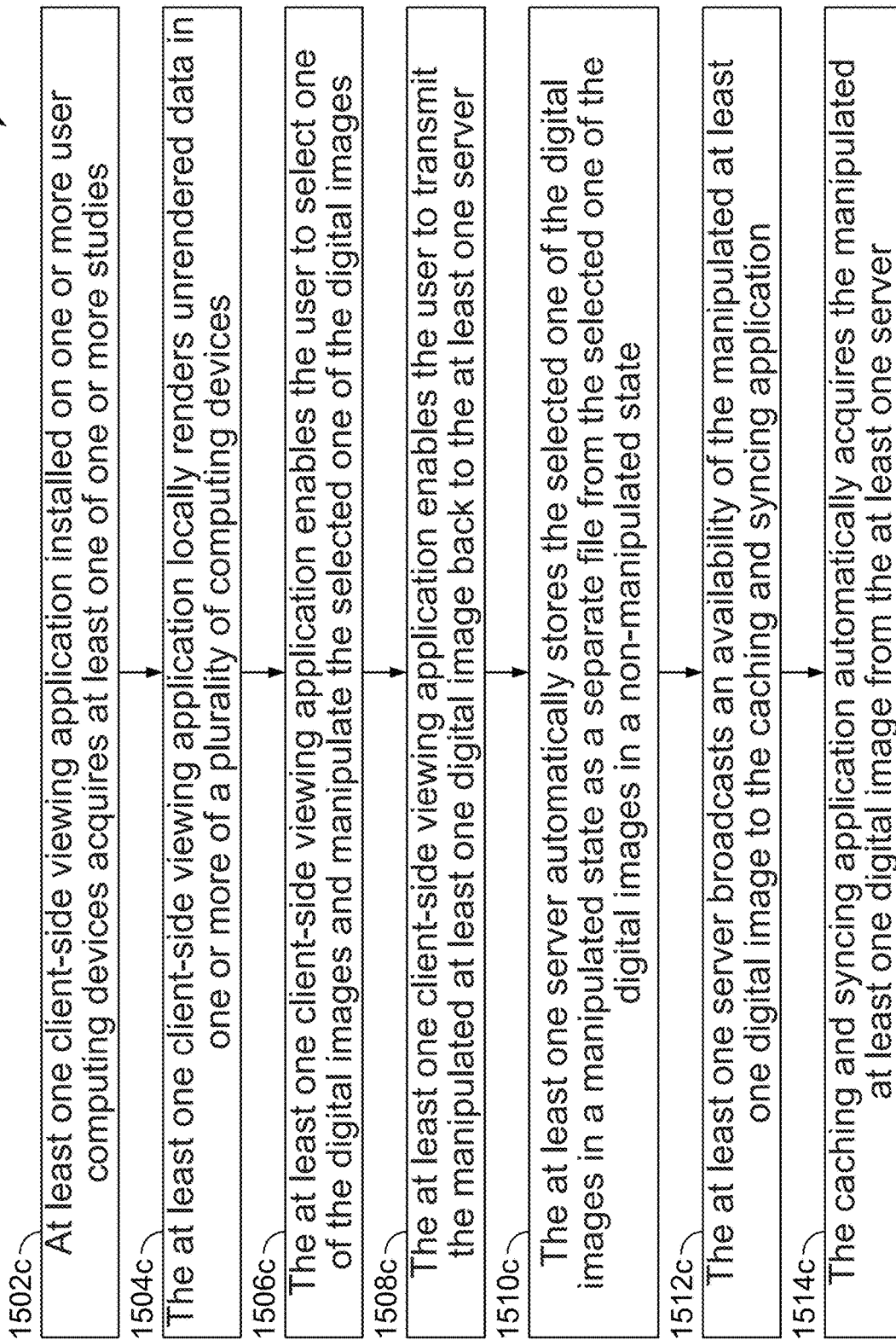
FIG. 15C is a flowchart of a plurality of exemplary steps of a third workflow implemented in the system of FIG. 1, in accordance with some embodiments of the present specification

FIG. 15C is a flowchart of a plurality of exemplary steps of a third workflow 1500c implemented in the system 100 of FIG. 1, in accordance with some embodiments of the present specification.

Referring now to FIGS. 1 and 15C, at step 1502c, at least one client-side viewing application installed on one or more user computing devices 106 acquires at least one of the one or more studies (as a result of a user requesting to access the at least one of the one or more studies), including therein unrendered data representative of the digital images of the first series, from at least one server 125.

At step 1504c, the at least one client-side viewing application locally renders the unrendered data in the one or more of the plurality of computing devices 106. In some embodiments, the at least one client-side viewing application renders the unrendered data by generating a graphical interface comprising a plurality of tabs and, when selected, a first of the plurality of tabs is configured to display a profile of the person, a second of the plurality of tabs is configured to display a list of the one or more studies specific to the person and a third of the plurality of tabs is configured to display analyses of the first series of the one or more studies.

In some embodiments, the analyses are generated by application of a neural network process or machine learning process to the digital images of the first series. In some embodiments, the at least one server 125 is configured to apply the neural network or machine learning process to the digital images by accessing, through an application program interface having a predefined format, a neural network or machine learning function executed by one or more separate servers and causing said one or more separate servers to apply the neural network or machine learning function to the digital images.

In some embodiments, the predefined format of the application program interface is specific to a cloud platform such as, but not limited to, Amazon AWS, Google cloud-based network.

At step 1506c, the at least one client-side viewing application enables the user to select one of the digital images and manipulate the selected one of the digital images. In some embodiments, the first series is a computed tomography series comprising the digital images and wherein the client-side viewing application enables the user to manipulate one of the digital images by selecting one of the digital images and applying a degree of zoom to the selected one of the digital images and/or associating an annotation to the selected one of the digital images.

At step 1508c, the at least one client-side viewing application enables the user to transmit the manipulated at least one digital image back to the at least one server 125. At step 1510c, the at least one server 125 automatically stores the selected one of the digital images in a manipulated state as a separate file from the selected one of the digital images in a non-manipulated state.

At step 1512c, the at least one server 125 broadcasts an availability of the manipulated at least one digital image to the caching and syncing application 109. In some embodiments, the at least one server 125 broadcasts a virtual address, link or URL of the stored one of the digital images in the manipulated state.

At step 1514c, the caching and syncing application 109 automatically acquires the manipulated at least one digital image from the at least one server 125. Further, in some embodiments, the caching and syncing application 109 automatically propagates the manipulated at least one digital image to the at least one image storage system 122 for storage so that the manipulated at least one digital image is readily accessible to one or more workstations 102 either from the caching and syncing device 108 and/or the at least one image storage system 122. In some embodiments, the caching and syncing application 109 automatically propagates the manipulated at least one digital image to the at least one image storage system 122 and to the one or more workstations 102.

In various embodiments, the caching and syncing application 109 queries the at least one server 125 for an existence of new digital images and, in response, the at least one server 125 transmits the virtual address of the stored one of the digital images in the manipulated state. In various embodiments, the caching and syncing application 109 is configured to be a sole gateway to accessing the digital images, stored in the at least one image storage system 122, outside of the local area network 120 and through a firewall configured to protect the local area network 120.

Figure 8:
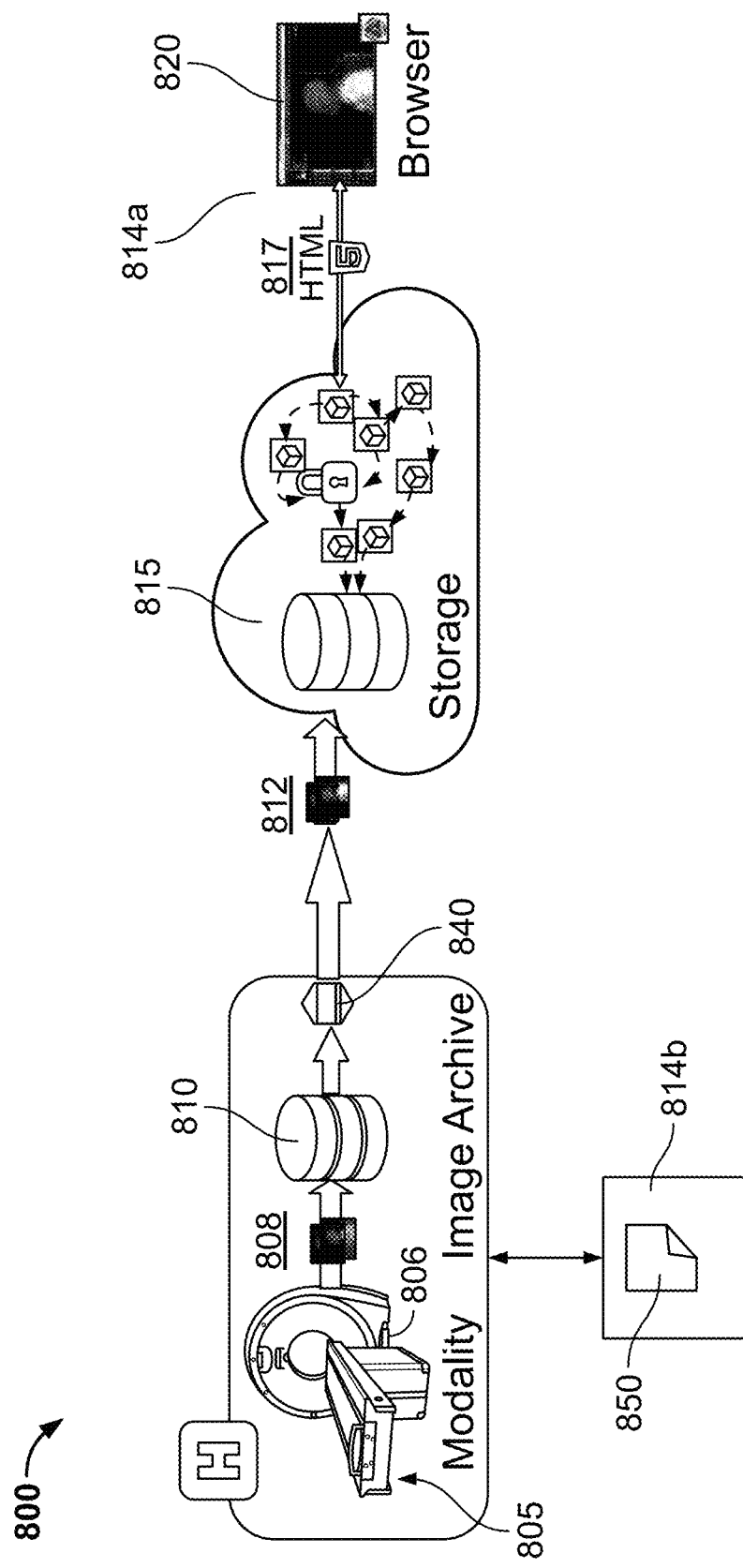
FIG. 8 illustrates a medical image acquisition and viewing workflow implemented using a serverless cloud computing system, in accordance with some embodiments of the present specification.

FIG. 8 illustrates a medical image acquisition and viewing workflow 800 implemented using a serverless cloud computing system (such as system 200 of FIG. 2A), in accordance with some embodiments of the present specification. Referring to FIG. 8, a plurality of medical imaging modalities or devices 805 are configured to perform medical imaging scans, at step 806, and generate a plurality of medical images. In various embodiments, the plurality of medical imaging devices 805 may include imaging modalities such as, but not limited to, an X-ray scanning system, an ultrasound imaging system, a fluorescence-based imaging system, a mammography system, a positron emission tomography system, a molecular imaging system, a MRI system, or a CT system, or any suitable medical imaging system known to persons of ordinary skill in the art.

In some embodiments, the plurality of medical imaging devices 805 may comprise a geographically distributed network of such devices. In some embodiments, the plurality of medical imaging devices 805 may comprise a co-located network of such devices.

The generated medical images are stored, at step 808, in at least one image storage system 810. In some embodiments, the at least one image storage system may comprise a local or geographically distributed SAN (storage area network). In some embodiments, at least one computing device 814b is in data communication with the plurality of medical imaging devices 805 to control medical imaging scanning operations and, in some embodiments, perform one or more (client-side) processing functions and/or manipulations on the acquired one or more medical images. In some embodiments, the computing device 814b is a technician workstation that an operator of a medical imaging device uses to capture relevant medical images and implements a client-side viewing application 850.

The plurality of medical imaging devices 805, the at least one image storage system 810, the at least one computing device 814b and a caching and syncing device 840 are in data communication with each other over a local area network. In some embodiments, the local area network is protected, by a firewall, from external networks. The caching and syncing device 840 implements a caching and syncing application and is in data communication with a serverless cloud computing system 815 through a network (such as, for example, the Internet) that is external to the local area network.

At step 812, the medical images stored in the one or more storage devices 810 are transmitted or communicated (via a wired and/or wireless network) by the caching and syncing device 840 to the serverless cloud computing system 815 for storage and for performing one or more processing functions on the stored images. In some embodiments, the serverless cloud computing system 815 is similar to the system 200 of FIG. 2A. Non-limiting examples of serverless cloud computing systems comprise Amazon Web Services (AWS) Lambda, Azure by Microsoft, Google Cloud and IBM SmartCloud.

In some embodiments, the computing device 814b is configured to receive a notification from the serverless cloud computing system 815 if one or more of the transmitted medical images are determined to have a quality below a predefined level. In other embodiments, the imaging modality 806 is configured to receive a notification if one or more medical images are determined to have a quality level below a predefined level by an application executing local to the imaging modality 806. In some embodiments, the quality is indicative of blur/sharpness and/or resolution of the one or more images.

At step 817, at least one user computing device 814a running a client-side viewing application 820 may request one or more medical images stored in the system 815. In some embodiments, the computing device 814a is a diagnostic workstation that a physician, radiologist or a caregiver may use to view and interact with the one or more medical images, series or studies. In some embodiments, the computing device 814a may execute one or more (client-side) processing functions on the one or more images rendered on the computing device 814a.

As a result of the request, in some embodiments, the system 815 may execute one or more processing functions on the requested one or more medical images a) before transferring the images to the computing device 814a for rendering on the client-side viewing application 820 (as a non-limiting example, an orientation, body part and view position function may be executed before transferring the images to the computing device 814a) and/or b) as a consequence of a user interacting with and/or manipulating (for example, panning, zooming, adjusting the contrast, annotating, or any other type of image manipulation) the images rendered on the client-side viewing application 820. In embodiments, the one or more processing functions are executed, on the system 815, in one or more execution environments such as, for example, containers or virtual machines in the system 815.

It should be appreciated that in some embodiments, the plurality of medical images generated by the plurality of medical imaging devices 805 are MPG4 files which cine through all the images of a stack so that the user can review them quickly.

Dynamic Advertising

Embodiments of the present specification also provide methods and systems to promote services and advertisements based on dynamic real-time data presented to a user through a 'patient jacket' generated by a client-side viewing application of a device such as the device 102 or 106 of FIG. 1, through a separate window generated by the client-side viewing application or through a separate, standalone viewer. In embodiments, metadata from DICOM data of medical images, series and studies is used to determine content to provide to the user. In some embodiments, the images and associated metadata are stored on a web server, also termed as Web Viewer Cache, and is described in detail in U.S. Pat. No. 9,659,030, titled "Web server for storing large files" and U.S. Pat. No. 9,298,730, titled "System and method for viewing medical images", and incorporated herein by reference in their entirety.

Referring back to FIG. 1, in some embodiments, the Web Viewer Cache is managed by services 115 and 117. In some embodiments, Web Viewer Cache is located in cloud platform 110 or 112. In some embodiments, the Web Viewer Cache is absent, and the user at device 106 accesses the images and associated metadata using DICOM Web directly from cloud archives 114.

The client-side viewing applications, through their services 115 or 117, are used by users to dynamically direct, distribute and manage image retrieval and processing. In embodiments, the client-side viewing application is used as a visual conduit through which advertising content may be delivered to users. Users may include clinicians who are reviewing images loaded in the client-side viewing application at devices 102, 106. The user's interaction with the client-side viewing application is analyzed to determine content to provide to the user. Analysis of the user's interaction may include a) the types of tools used by the user, b) the types of images corresponding to types of devices used to originally source the images such as X-ray machines, MRIs, or any other types of devices, c) the number of images viewed, d) neural network based analyses of the images and any other information that may aid in analyzing the user's interaction with the client-side viewing application. In alternative embodiments, cloud-platform services are queried at the time of loading images on the client-side viewing application by the user in order to determine what content to provide to the user.

In one embodiment, the client-side viewing application extracts content of the images loaded by the user. Medical images stored in DICOM format contain, in addition to the image of a patient, additional data such as metadata including information about the medical study conducted on the patient, the modality of the study or examination, date of acquisition, protocol used for acquisition, body part(s) studied, descriptions, among other medical information associated with the patient and/or the images. The metadata is integrated in DICOM tags that is a value representation describing a data type and format of the attribute value. Embodiments of the client-side viewing application, in accordance with the present specification, uses these DICOM tags to extract information about the medical study and the image loaded by the user for viewing. Tags, including and not limited to, those comprising a description of the study, for example, 0008,1030, and tags comprising body part and modality, for example, 0018,0015 and 0008,0060, may be used specifically to extract information that is used to determine content to be displayed to the user in real time, with the loaded image. Further, the loaded images themselves may be used to determine the content to be provided to the user. In some embodiments, a common image artifact, or an analysis of the anatomy, or an identification of a pathology, is used to determine the content to be provided to the user. In embodiments, during the process of extracting information along with a loaded image or images, any personal information such as name, patient identity, or any other personal data is discarded to ensure patient privacy.

In some embodiments, a user's interaction with the client-side viewing application is monitored to determine the user's objectives. The determined objectives are used to identify and display suitable content to the user in real time. Monitoring user's interaction may include, for instance, monitoring the types of tools used. The types of tools could be an indication of a type of clinical procedure. For example, an orthopedic surgeon would use calibration tools and leg-length tools. The types of devices used to view the images could also be an indication of the user's objective. For example, a radiologist is more likely to view images on a laptop as opposed to a phone or a tablet. Further, the numbers of images viewed could be an indication of the user's objective. For example, a radiologist is more likely to view all the images in a study in case of CR, DX, MG, and US studies, and review all the axial images in a CT study.

In some embodiments, the client-side viewing application queries a cloud platform at run time to determine the services that may be relevant to user's objectives. Alternatively, the query may be executed in a client-side viewing application in the background when an image or images are requested and/or loaded by the user using the client-side viewing application, to determine the services that may be applicable to the study being viewed by the user. For instance, a breast density AI module provides only mammography images. If one or more applicable services are found, it could prompt the user to try them out. In an embodiment, an AI service to interpret the images is promoted to the user. Afterwards, if the user is satisfied with the services, the client-side viewing application could systematically use the services for the images of that specific user. In various embodiments a variety of services and products are advertised to the user. In embodiments, based on the use profile and the data loaded, the client-side viewing application queries a service, such as for example Google's AdSense, which in turn services the query or presents products to the user.

The information extracted by using one or more of the above described methods may be used to deliver advertisements or any other content to a user. In embodiments, DICOM tags, and other information extracted as above, are used by the client-side viewing application to identify key words and images, to search advertisement content. In some embodiments, a type of tool used by the user may be tracked and tags relevant to the tool may be added to the plurality of information used to search for advertising content, thereby enriching the relevance and depth of the search. Advertisement content may be collected and stored by specialized providers, such as but not limited to, Google.

In an exemplary embodiment, the client-side viewing application uses identified advertisement-related information to find a relevant scientific paper that could interest the user. The paper may be searched in the background while the user views the study. The paper could be identified using the Google's engine, or any other paper publishing service, in order to list papers that are relevant to the user's study.

In another exemplary embodiment, the client-side viewing application uses above advertisement-related information to generate an image, video, or other visual or auditory display comprising a product advertisement, e.g. a surgical implant, a medical device, or any other medical equipment. For this purpose, the client-side viewing application enables the user who may be a surgeon or a physician, to display drawing of a surgical implant or medical equipment overlaid on the patient's images and also calibrated, thereby providing an opportunity to the surgeon/physician to purchase the surgical implant/medical equipment or order to purchase it from a manufacturer.

In another exemplary embodiment, the client-side viewing application uses above information to promote accredited medical courses, for which a doctor needs to spend a fix amount of time in attending these courses to keep the accreditation.

The above examples are merely illustrative of the many applications of the system and method of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:

1. A method of training a plurality of neural networks using a first set of one or more digital images and providing access to the trained plurality of neural networks, wherein each of the first set of one or more digital images is associated with at least one of an imaging modality, an anatomy of a person, a diagnosis of the person, an age of the person, a gender of the person, data indicative of contouring, an aggregated score, or a property of the anatomy of the person, comprising:

receiving, in at least one client-side viewing application, the first set of one or more digital images;

receiving, in the at least one client-side viewing application, a modification of the first set of one or more digital images;

transmitting the modified first set of one or more digital images to at least one server;

selecting one of the plurality of neural networks to train based, at least in part, on the imaging modality, the anatomy of the person, the diagnosis of the person, the age of the person, the gender of the person, data indicative of contouring, the aggregated score, or the property of the anatomy of the person associated with the modified first set of one or more digital images;

training the selected neural network based on the modified first set of one or more digital images using the at least one server;

receiving, in the at least one client-side viewing application, a request to apply one of the plurality of neural networks to a second set of one or more digital images;

in response to the request, selecting one of the plurality of neural networks to apply based, at least in part, on an imaging modality, an anatomy of a person, a diagnosis of the person, an age of the person, a gender of the person, data indicative of contouring, an aggregated score, or a property of the anatomy of the person associated with the second set of the one or more digital images;

applying the selected one of the plurality of neural networks to the second set of one or more digital images to generate at least one of a graphical, audio, alphanumeric text, or video result; and displaying or playing the graphical, audio, alphanumeric text, or video result using the client-side viewing application.

2. The method of claim 1, wherein the imaging modality is at least one of an X-ray scanning system, an ultrasound imaging system, a fluorescence-based imaging system, a mammography system, a positron emission tomography system, a molecular imaging system, a MRI system, or a CT system.

3. The method of claim 1, further comprising selecting a first of the plurality of neural networks to train based on a first imaging modality associated with the modified first set of one or more digital images and selecting a second of the plurality of neural networks to train based on a second imaging modality associated with the modified first set of one or more digital images, wherein the first imaging modality is different from the second imaging modality and wherein the first of the plurality of neural networks is different from the second of the plurality of neural networks.

4. The method of claim 3, wherein the first imaging modality and the second imaging modality is at least one of an X-ray scanning system, an ultrasound imaging system, a fluorescence-based imaging system, a mammography system, a positron emission tomography system, a molecular imaging system, a MRI system, or a CT system.

5. The method of claim 1, wherein the modification of the first set of one or more digital images is at least one of an annotation of the first set of one or more digital images, a labeling of the first set of one or more digital images with the imaging modality, a labeling of the first set of one or more digital images with the anatomy of the person, a labeling of the first set of one or more digital images with the diagnosis of the person, a labeling of the first set of one or more digital images with the gender of the person, a labeling of the first set of one or more digital images with the age of the person, a labeling of the first set of one or more digital images with data indicative of contouring, a labeling of the first set of one or more digital images with the aggregated score, a labeling of the first set of one or more digital images with the property of the anatomy of the person, an association of one or more visible features in the first set of one or more digital images with a disease state of the person, a visible highlighting of one or more visible features of the first set of one or more digital images with the disease state of the person, a measurement of visible features in the first set of one or more digital images, or a change in an orientation, color, zoom, rotation, brightness, or saturation in the first set of one or more digital images.

6. The method of claim 1, wherein the plurality of network networks is at least one of a deep feed forward network, a perceptron network, a feed forward network, a radial basis network, a recurrent neural network, a long term memory network, a short term memory network, a gated recurrent unit network, an auto encoder network, a variational auto encoder network, a denoising auto encoder network, a sparse auto encoder network, a Markov chain network, a Hopfield network, a Boltzmann machine network, a restricted Boltzmann machine network, a deep belief network, a deep convolutional network, a deconvolutional network, a deep convolutional inverse graphics network, a generated adversarial network, a liquid state machine, an extreme learning machine, an echo state network, a deep residual network, a Kohonen network, a support vector machine network, a neural Turing machine network, or a convolutional neural network with transfer learning network.

7. The method of claim 1, wherein each of the first set of one or more digital images is in a DICOM format, wherein each of the first set of one or more digital images comprises one or more tags, and wherein the one or more tags of each of the first set of one or more digital images comprises data indicative of the imaging modality, the anatomy of a person, the diagnosis of the person, the age of the person, the gender of the person, data indicative of contouring, the aggregated score, or the property of the anatomy of the person.

8. The method of claim 1, wherein the selecting of one of the plurality neural networks to apply in response to the request is performed by the client-side viewing application and is based, at least in part, on the imaging modality associated with the second set of one or more digital images.

9. The method of claim 1, wherein the selecting of one of the plurality neural networks to apply in response to the request is performed by the at least one server and is based, at least in part, on the diagnosis of the person associated with the second set of one or more digital images.

10. The method of claim 1, wherein the selecting of one of the plurality neural networks to apply in response to the request is performed by the client-side viewing application and is based, at least in part, on the anatomy of the person associated with the second set of one or more digital images.

11. The method of claim 1, wherein the selecting of one of the plurality neural networks to apply in response to the request is performed by the at least one server and is based, at least in part, on data indicative of contouring associated with the second set of one or more digital images.

12. The method of claim 1, wherein, after selecting one of the plurality of neural networks to train and before training the selected neural network, the at least one server applies a quality check function to the modified first set of one or more digital images.

13. The method of claim 1, wherein the at least one server selects one of the plurality of neural networks to train based, at least in part, on data in one or more DICOM tags associated with the modified first set of one or more digital images.

14. The method of claim 1, wherein the selection of the plurality of neural networks to apply to the second set of one or more digital images is based, at least in part, on data in one or more DICOM tags associated with the second set of one or more digital images.

15. The method of claim 1, wherein the training comprises modifying a topology of the selected neural network.

16. The method of claim 1, wherein the training comprises modifying a weight associated with one or more nodes of the selected neural network.

17. The method of claim 1, wherein the training comprises modifying a number or ordering of one or more layers of the selected neural network.

18. The method of claim 1, further comprising selecting a first of the plurality of neural networks to train based on a first imaging modality associated with a first of the modified first set of one or more digital images and selecting a second of the plurality of neural networks to train based on a second imaging modality associated with a second of the modified first set of one or more digital images, wherein the first imaging modality and the second imaging modality are different from each other and are at least one of an X-ray scanning system, an ultrasound imaging system, a fluorescence-based imaging system, a mammography system, a positron emission tomography system, a molecular imaging system, a MRI system, or a CT system, and wherein a topology of the first of the plurality of neural networks is different from a topology of the second of the plurality of neural networks.

19. The method of claim 1, wherein each of the second set of one or more digital images represents a slice of a three-dimensional image and is associated with a computed tomography imaging modality.

20. The method of claim 19, wherein the at least one client-side viewing application, receives a modification of one slice of the three-dimensional image and wherein the selected one of the plurality of neural networks applied to the second set of one or more digital images is configured to propagate the modification to other slices in the three-dimensional image.

21. The method of claim 20, wherein the modification is a visual highlight of an edge of an anatomical feature in said slice and wherein the propagation of the modification to other slices in the three-dimensional image causes said visual highlight of the edge of the anatomical feature to appear in the other slices of the three-dimensional image without manual intervention.

22. The method of claim 1, wherein each of the second set of one or more digital images is associated with at least one series, wherein each of the at least one series is associated with at least one study, and wherein the at least one study is associated with only one person and with only one imaging modality.

23. The method of claim 22, wherein the at least one client-side viewing application is configured to generate a graphical user interface comprising a listing of the at least one study and at least one of the graphical, audio, alphanumeric text, or video result.

24. The method of claim 22, wherein the at least one client-side viewing application is configured to generate a graphical user interface comprising a listing of the at least one study and a link to the at least one of the graphical, audio, alphanumeric text, or video result.

25. The method of claim 1, wherein the at least one server selects one of the plurality of neural networks to train automatically upon receiving the modified first set of one or more digital images and determining data in at least one DICOM tag associated with the modified first set of one or more digital images.

26. The method of claim 1, wherein the at least one server is configured to receive the modified first set of one or more digital images from a first client-side viewing application controlled by a first user and is configured to receive a modified third set of one or more digital images from a second client-side viewing application controlled by a second user and wherein the first user is different from the second user.

27. The method of claim 26, wherein the first client-side viewing application is configured to execute in a first local area network and wherein the second client-side viewing application is configured to execute in a second local area network and wherein the first local area network is separated from the second local area network by at least one firewall.

28. The method of claim 1, wherein each of the second set of one or more digital images represent a portion of a multi-image data set of one person acquired at a same time and using a same imaging modality.

29. The method of claim 28, wherein the at least one client-side viewing application, receives a modification of one portion of the multi-image data set and wherein the selected one of the plurality of neural networks applied to the second set of one or more digital images is configured to propagate the modification to other portions in the multi-image data set.

30. The method of claim 29, wherein the modification is a visual identification of an anatomical feature in said one portion and wherein the propagation of the modification to other portions in the multi-image image data set causes said visual identification of the anatomical feature to be associated with said anatomical feature in the other portions of the multi-image data set.

\* \* \* \* \*